(12) United States Patent
Wells et al.

(10) Patent No.: US 11,066,650 B2
(45) Date of Patent: Jul. 20, 2021

(54) METHODS FOR THE IN VITRO MANUFACTURE OF GASTRIC FUNDUS TISSUE AND COMPOSITIONS RELATED TO SAME

(71) Applicant: Children's Hospital Medical Center, Cincinnati, OH (US)

(72) Inventors: James Wells, Cincinnati, OH (US); Kyle McCracken, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 16/084,599

(22) PCT Filed: May 5, 2017

(86) PCT No.: PCT/US2017/031309
§ 371 (c)(1),
(2) Date: Sep. 13, 2018

(87) PCT Pub. No.: WO2017/192997
PCT Pub. Date: Nov. 9, 2017

(65) Prior Publication Data
US 2019/0078055 A1 Mar. 14, 2019

Related U.S. Application Data

(60) Provisional application No. 62/332,194, filed on May 5, 2016.

(51) Int. Cl.
*C12N 5/071* (2010.01)
*C12N 5/0735* (2010.01)
*C12N 5/074* (2010.01)
*C12N 5/075* (2010.01)

(52) U.S. Cl.
CPC .......... *C12N 5/0679* (2013.01); *C12N 5/0606* (2013.01); *C12N 5/0607* (2013.01); *C12N 5/0609* (2013.01); *C12N 2501/11* (2013.01); *C12N 2501/115* (2013.01); *C12N 2501/155* (2013.01); *C12N 2501/385* (2013.01); *C12N 2501/415* (2013.01); *C12N 2506/025* (2013.01); *C12N 2506/03* (2013.01); *C12N 2506/45* (2013.01); *C12N 2513/00* (2013.01)

(58) Field of Classification Search
CPC .................................................. C12N 5/0679
See application file for complete search history.

(56) References Cited

U.S. PATENT DOCUMENTS

| | | | |
|---|---|---|---|
| 5,912,227 A | 6/1999 | Croom, Jr. et al. | |
| 5,942,435 A | 8/1999 | Wheeler | |
| 6,607,501 B2 | 8/2003 | Gorsuch | |
| 7,160,719 B2 | 1/2007 | Nyberg | |
| 7,291,626 B1 | 11/2007 | Beachy et al. | |
| 7,326,572 B2 | 2/2008 | Fisk et al. | |
| 7,510,876 B2 | 3/2009 | D'Amour et al. | |
| 7,514,185 B2 | 4/2009 | Fukushima et al. | |
| 7,541,185 B2 | 6/2009 | D'Amour et al. | |
| 7,625,753 B2 | 12/2009 | Kelly et al. | |
| 7,695,958 B2 | 4/2010 | Funatsu et al. | |
| 7,704,738 B2 | 4/2010 | D'Amour et al. | |
| 7,727,998 B2 | 6/2010 | Moriya et al. | |
| 7,776,592 B2 | 8/2010 | Wandinger-Ness et al. | |
| 7,927,869 B2 | 4/2011 | Rosero | |
| 7,985,585 B2 | 7/2011 | D'Amour et al. | |
| 7,993,916 B2 | 8/2011 | Agulnick et al. | |
| 8,187,878 B2 | 5/2012 | Dalton et al. | |
| 8,216,826 B2 | 7/2012 | Lee et al. | |
| 8,216,836 B2 | 7/2012 | D'Amour et al. | |
| 8,298,822 B2 | 10/2012 | Kruse et al. | |
| 8,318,492 B2 | 11/2012 | Choo et al. | |
| 8,501,476 B2 | 8/2013 | Morgan et al. | |
| 8,586,357 B2 | 11/2013 | D'Amour et al. | |
| 8,603,809 B2 | 12/2013 | Kruse | |
| 8,609,406 B2 | 12/2013 | Subramanian et al. | |
| 8,609,413 B2 | 12/2013 | Suter et al. | |
| 8,623,645 B2 | 1/2014 | D'Amour et al. | |
| 8,632,645 B2 | 1/2014 | Daitou et al. | |
| 8,633,024 B2 | 1/2014 | D'Amour et al. | |
| 8,642,339 B2 | 2/2014 | Sato et al. | |

(Continued)

FOREIGN PATENT DOCUMENTS

| CN | 103154237 A | 6/2013 |
|---|---|---|
| CN | 103561751 A | 2/2014 |

(Continued)

OTHER PUBLICATIONS

Ahnfelt-Ronne, J., et al., "An improved method for three-dimensional reconstruction of protein expression patterns in intact mouse and chicken embryos and organs," J. Histochem. Cytochem., 2007, 55:925-930, 6 pgs.
Aronson, B.E., et al., "GATA4 represses an ileal program of gene expression in the proximal small intestine by inhibiting the acetylation of histone H3, lysine 27," Biochim, Biophys. Acta, 2014, 1839(11):1273-1282, 31 pgs.
Bartfeld, S., et al., "In Vitro Expansion of Human Gastric Epithelial Stem Cells and Their Responses to Bacterial Infection," Gastroenterology, Jan. 2015, 148(1):126-136, 22 pgs.
Battle, M.A., et al., "GATA4 is essential for jejunal function in mice," Gastroenterology, 2008, 135:1676-7686, 17 pgs.

(Continued)

*Primary Examiner* — Thaian N. Ton
*Assistant Examiner* — David A. Montanari
(74) *Attorney, Agent, or Firm* — Knobbe, Martens, Olson & Bear, LLP

(57) ABSTRACT

The instant disclosure relates to methods for converting mammalian definitive endoderm (DE) cells into specific tissue(s) or organ(s) through directed differentiation. In particular, the disclosure relates to formation of gastric fundus tissue and/or organoids formed from differentiated definitive endoderm.

16 Claims, 15 Drawing Sheets

Specification includes a Sequence Listing.

(56) References Cited

U.S. PATENT DOCUMENTS

| | | |
|---|---|---|
| 8,647,873 B2 | 2/2014 | D'Amour et al. |
| 8,658,151 B2 | 2/2014 | Kelly et al. |
| 8,685,386 B2 | 4/2014 | West et al. |
| 8,685,730 B2 | 4/2014 | Odorico et al. |
| 8,758,323 B2 | 6/2014 | Michaud et al. |
| 9,127,254 B2 | 9/2015 | Cohen et al. |
| 9,133,439 B2 | 9/2015 | Davis et al. |
| 9,181,301 B2 | 11/2015 | Carlson et al. |
| 9,200,258 B2 | 12/2015 | Mezghanni et al. |
| 9,206,393 B2 | 12/2015 | Kruse |
| 9,234,170 B2 | 1/2016 | Snoeck et al. |
| 9,334,479 B2 | 5/2016 | Herrera Sanchez et al. |
| 9,375,514 B2 | 6/2016 | Kruse et al. |
| 9,381,181 B2 | 7/2016 | Roberts et al. |
| 9,394,522 B2 | 7/2016 | Brolen et al. |
| 9,446,076 B2 | 9/2016 | Gaussin et al. |
| 9,447,380 B2 | 9/2016 | Subramanian et al. |
| 9,476,030 B2 | 10/2016 | Gadue et al. |
| 9,499,795 B2 | 11/2016 | D'Amour et al. |
| 9,605,243 B2 | 3/2017 | D'Amour et al. |
| 9,616,039 B2 | 4/2017 | Roberts et al. |
| 9,618,500 B2 | 4/2017 | Giselbrecht et al. |
| 9,650,609 B2 | 5/2017 | Nyberg |
| 9,675,646 B2 | 6/2017 | Bitar |
| 9,677,085 B2 | 6/2017 | Guye et al. |
| 9,719,067 B2 | 8/2017 | Snoeck et al. |
| 9,719,068 B2 | 8/2017 | Wells et al. |
| 9,732,116 B2 | 8/2017 | Steiner et al. |
| 9,752,124 B2 | 9/2017 | Sato et al. |
| 9,763,964 B2 | 9/2017 | Pellicciari et al. |
| 9,765,301 B2 | 9/2017 | Huch Ortega et al. |
| 9,771,562 B2 | 9/2017 | Shen et al. |
| 9,790,470 B2 | 10/2017 | Vallier et al. |
| 9,828,583 B2 | 11/2017 | Rajagopal et al. |
| 9,849,104 B2 | 12/2017 | Bisgaier et al. |
| 9,850,461 B2 | 12/2017 | Rizzi et al. |
| 9,856,458 B2 | 1/2018 | Rosowski et al. |
| 9,878,005 B2 | 1/2018 | Johns et al. |
| 9,914,920 B2 | 3/2018 | Goodwin et al. |
| 9,926,532 B2 | 3/2018 | Esteban et al. |
| 9,938,499 B2 | 4/2018 | Slukvin et al. |
| 10,023,922 B2 | 7/2018 | Stelzer et al. |
| 10,045,977 B2 | 8/2018 | Wu et al. |
| 10,047,341 B2 | 8/2018 | Yu et al. |
| 10,052,337 B2 | 8/2018 | Lancaster et al. |
| 10,000,740 B2 | 9/2018 | Vallier et al. |
| 10,087,416 B2 | 10/2018 | Chan et al. |
| 10,087,417 B2 | 10/2018 | Freed et al. |
| 10,100,279 B2 | 10/2018 | Nicholas et al. |
| 10,130,748 B2 | 11/2018 | Nyberg et al. |
| 10,172,889 B2 | 1/2019 | Sokal et al. |
| 10,174,289 B2 | 1/2019 | Wells et al. |
| 10,179,176 B2 | 1/2019 | Kay et al. |
| 10,220,386 B2 | 3/2019 | Williamson et al. |
| 10,222,370 B2 | 3/2019 | Keshavarzian et al. |
| 10,260,039 B2 | 4/2019 | Bhatia et al. |
| 10,265,153 B2 | 4/2019 | La Francesca et al. |
| 10,265,453 B2 | 4/2019 | Flieg et al. |
| 10,301,303 B2 | 5/2019 | Liu |
| 10,350,147 B2 | 7/2019 | Kyrkanides et al. |
| 10,369,254 B2 | 8/2019 | Yanagawa et al. |
| 10,407,664 B2 | 9/2019 | Knoblich et al. |
| 10,426,757 B2 | 10/2019 | Sabatini et al. |
| 10,449,221 B2 | 10/2019 | Kotton et al. |
| 10,472,612 B2 | 11/2019 | Ingber et al. |
| 10,479,977 B2 | 11/2019 | Wang et al. |
| 10,487,314 B2 | 11/2019 | Accili et al. |
| 10,532,111 B2 | 1/2020 | Kay et al. |
| 10,538,741 B2 | 1/2020 | Sokal et al. |
| 10,545,133 B2 | 1/2020 | Ewald et al. |
| 10,555,929 B2 | 2/2020 | Mantzoros |
| 2003/0129751 A1 | 7/2003 | Grikscheit et al. |
| 2005/0266554 A1 | 12/2005 | D'Amour et al. |
| 2006/0110369 A1 | 5/2006 | Funatsu et al. |
| 2006/0236415 A1 | 10/2006 | Silversides et al. |
| 2007/0238169 A1 | 10/2007 | Abilez et al. |
| 2007/0239083 A1 | 10/2007 | Voss |
| 2008/0193421 A1 | 8/2008 | Kruse et al. |
| 2009/0011502 A1 | 1/2009 | D'Amour et al. |
| 2009/0042287 A1 | 2/2009 | D'Amour et al. |
| 2009/0220959 A1 | 9/2009 | D'Amour et al. |
| 2009/0253202 A1 | 10/2009 | D'Amour et al. |
| 2009/0263357 A1 | 10/2009 | Sayre et al. |
| 2010/0016410 A1 | 1/2010 | Wagner et al. |
| 2010/0041150 A1 | 2/2010 | Kelly et al. |
| 2010/0048871 A1 | 2/2010 | Cho et al. |
| 2010/0075295 A1 | 3/2010 | Dryden et al. |
| 2010/0151568 A1 | 6/2010 | D'Amour et al. |
| 2011/0151564 A1 | 6/2011 | Menu et al. |
| 2011/0218512 A1 | 9/2011 | Tullis et al. |
| 2011/0294735 A1 | 12/2011 | Marsh et al. |
| 2012/0071451 A1 | 3/2012 | Spenard et al. |
| 2012/0135519 A1 | 5/2012 | Ameri et al. |
| 2012/0149630 A1 | 6/2012 | Zugates et al. |
| 2012/0196275 A1 | 8/2012 | Mezghanni et al. |
| 2012/0196312 A1 | 8/2012 | Sato et al. |
| 2012/0264209 A1 | 10/2012 | Odorico et al. |
| 2013/0031645 A1 | 1/2013 | Touboul et al. |
| 2013/0095567 A1 | 4/2013 | Brolen et al. |
| 2013/0115673 A1 | 5/2013 | West et al. |
| 2013/0137130 A1 | 5/2013 | Wells et al. |
| 2013/0189327 A1 | 7/2013 | Ortega et al. |
| 2013/0217005 A1 | 8/2013 | Snoeck et al. |
| 2013/0281374 A1 | 10/2013 | Levy et al. |
| 2013/0316442 A1 | 11/2013 | Meurville et al. |
| 2014/0038279 A1 | 2/2014 | Ingber et al. |
| 2014/0044713 A1 | 2/2014 | De Lau et al. |
| 2014/0141509 A1* | 5/2014 | Gadue ............... C12N 5/0672 435/357 |
| 2014/0193905 A1 | 7/2014 | Kelly et al. |
| 2014/0212910 A1 | 7/2014 | Bhatia et al. |
| 2014/0234953 A1 | 8/2014 | Vacanti et al. |
| 2014/0243227 A1 | 8/2014 | Clevers et al. |
| 2014/0273210 A1 | 9/2014 | Baker et al. |
| 2014/0302491 A1* | 10/2014 | Nadauld ............ G01N 33/5017 435/5 |
| 2014/0308695 A1 | 10/2014 | Bruce et al. |
| 2014/0336282 A1 | 11/2014 | Ewald et al. |
| 2015/0017140 A1 | 1/2015 | Bhatia et al. |
| 2015/0151297 A1 | 6/2015 | Williamson et al. |
| 2015/0153326 A1 | 6/2015 | Kogel et al. |
| 2015/0197802 A1 | 7/2015 | Zink et al. |
| 2015/0201588 A1 | 7/2015 | Kamb et al. |
| 2015/0238656 A1 | 8/2015 | Orlando et al. |
| 2015/0273071 A1 | 10/2015 | Green et al. |
| 2015/0290154 A1 | 10/2015 | Roberts et al. |
| 2015/0330970 A1 | 11/2015 | Knoblich et al. |
| 2015/0343018 A1 | 12/2015 | Sansonetti et al. |
| 2015/0359849 A1 | 12/2015 | Greenberg et al. |
| 2015/0361393 A1 | 12/2015 | Nicholas et al. |
| 2016/0002602 A1 | 1/2016 | Almeida-Porada et al. |
| 2016/0022873 A1 | 1/2016 | Besner et al. |
| 2016/0060707 A1 | 3/2016 | Goldenberg et al. |
| 2016/0068805 A1 | 3/2016 | Martin et al. |
| 2016/0101133 A1 | 4/2016 | Basu et al. |
| 2016/0102289 A1 | 4/2016 | Yu et al. |
| 2016/0121023 A1 | 5/2016 | Edelman et al. |
| 2016/0122722 A1 | 5/2016 | Ejiri et al. |
| 2016/0143949 A1 | 5/2016 | Ingber et al. |
| 2016/0177270 A1 | 6/2016 | Takebe et al. |
| 2016/0184387 A1 | 6/2016 | Charmot et al. |
| 2016/0206664 A1 | 7/2016 | Sokal et al. |
| 2016/0237400 A1 | 8/2016 | Xian |
| 2016/0237401 A1 | 8/2016 | Vallier et al. |
| 2016/0237409 A1 | 8/2016 | Little et al. |
| 2016/0245653 A1 | 8/2016 | Park et al. |
| 2016/0256672 A1 | 9/2016 | Arumugaswami et al. |
| 2016/0257937 A1 | 9/2016 | Wauthier et al. |
| 2016/0263098 A1 | 9/2016 | Mantzoros |
| 2016/0289635 A1 | 10/2016 | Sasai et al. |
| 2016/0296599 A1 | 10/2016 | Dinh et al. |
| 2016/0312181 A1 | 10/2016 | Freed et al. |
| 2016/0312190 A1 | 10/2016 | Ghaedi et al. |
| 2016/0312191 A1 | 10/2016 | Spence et al. |

(56) References Cited

U.S. PATENT DOCUMENTS

| | | |
|---|---|---|
| 2016/0319240 A1 | 11/2016 | Chan et al. |
| 2016/0340645 A1 | 11/2016 | D'Amour et al. |
| 2016/0340749 A1 | 11/2016 | Stelzer et al. |
| 2016/0354408 A1 | 12/2016 | Hariri et al. |
| 2016/0361466 A1 | 12/2016 | Yanagawa et al. |
| 2016/0376557 A1 | 12/2016 | Dubart Kupperschmitt et al. |
| 2017/0002330 A1 | 1/2017 | Vunjak-Novakovic et al. |
| 2017/0027994 A1 | 2/2017 | Kotton et al. |
| 2017/0035661 A1 | 2/2017 | Kyrkanides et al. |
| 2017/0035784 A1 | 2/2017 | Lancaster et al. |
| 2017/0037043 A1 | 2/2017 | Liu |
| 2017/0067014 A1 | 3/2017 | Takebe et al. |
| 2017/0292116 A1 | 3/2017 | Wells et al. |
| 2017/0101628 A1 | 4/2017 | Ingber et al. |
| 2017/0107469 A1 | 4/2017 | Costa et al. |
| 2017/0107483 A1 | 4/2017 | Pendergraft et al. |
| 2017/0107498 A1 | 4/2017 | Sareen et al. |
| 2017/0128625 A1 | 5/2017 | Bhatia et al. |
| 2017/0151049 A1 | 6/2017 | La Francesca et al. |
| 2017/0152486 A1 | 6/2017 | Shen et al. |
| 2017/0152528 A1 | 6/2017 | Zhang |
| 2017/0184569 A1 | 6/2017 | Keshavarzian et al. |
| 2017/0191030 A1 | 7/2017 | Huch Ortega et al. |
| 2017/0198261 A1 | 7/2017 | Sabaawy et al. |
| 2017/0204375 A1 | 7/2017 | Accili et al. |
| 2017/0205396 A1 | 7/2017 | Izpisua Belmonte et al. |
| 2017/0205398 A1 | 7/2017 | Bruce et al. |
| 2017/0239262 A1 | 8/2017 | Lefebvre |
| 2017/0240863 A1 | 8/2017 | Sokal et al. |
| 2017/0240866 A1 | 8/2017 | Wells et al. |
| 2017/0240964 A1 | 8/2017 | Leung et al. |
| 2017/0258772 A1 | 9/2017 | Sabatini et al. |
| 2017/0260501 A1 | 9/2017 | Semechkin et al. |
| 2017/0266145 A1 | 9/2017 | Nahmias et al. |
| 2017/0267970 A1 | 9/2017 | Gupta et al. |
| 2017/0267977 A1 | 9/2017 | Huang et al. |
| 2017/0275592 A1 | 9/2017 | Sachs et al. |
| 2017/0285002 A1 | 10/2017 | Taniguchi et al. |
| 2017/0296621 A1 | 10/2017 | Sansonetti et al. |
| 2017/0304294 A1 | 10/2017 | Wu et al. |
| 2017/0304369 A1 | 10/2017 | Ang et al. |
| 2017/0319548 A1 | 11/2017 | Lefebvre |
| 2017/0321188 A1 | 11/2017 | Viczian et al. |
| 2017/0321191 A1 | 11/2017 | Kojima |
| 2017/0335283 A1 | 11/2017 | Wang et al. |
| 2017/0342385 A1 | 11/2017 | Sachs et al. |
| 2017/0348433 A1 | 12/2017 | Kay et al. |
| 2017/0349659 A1 | 12/2017 | Garcia et al. |
| 2017/0349884 A1 | 12/2017 | Karp et al. |
| 2017/0360962 A1 | 12/2017 | Kay et al. |
| 2017/0362573 A1 | 12/2017 | Wells et al. |
| 2018/0021341 A1 | 1/2018 | Harriman et al. |
| 2018/0030409 A1 | 2/2018 | Lewis et al. |
| 2018/0042970 A1 | 2/2018 | Rossen et al. |
| 2018/0059119 A1 | 3/2018 | Takats et al. |
| 2018/0112187 A1 | 4/2018 | Smith et al. |
| 2018/0250410 A1 | 9/2018 | Borros Gomez et al. |
| 2019/0031992 A1 | 1/2019 | Kerns et al. |
| 2019/0153395 A1 | 5/2019 | Barrett et al. |
| 2019/0153397 A1 | 5/2019 | Wells et al. |
| 2019/0298775 A1 | 10/2019 | Takebe et al. |
| 2019/0314387 A1 | 10/2019 | Takebe et al. |
| 2019/0367882 A1 | 12/2019 | Wells et al. |
| 2020/0040309 A1 | 2/2020 | Takebe et al. |

FOREIGN PATENT DOCUMENTS

| | | | |
|---|---|---|---|
| CN | 105985395 A | 10/2016 | |
| EP | 2393917 A2 | 12/2011 | |
| EP | 2393917 B1 | 4/2016 | |
| EP | 3228306 A1 | 10/2017 | |
| JP | 2003-521673 A | 7/2003 | |
| JP | 2008-503203 A | 2/2008 | |
| JP | 2008-505638 A | 2/2008 | |
| JP | 2013-066414 A | 4/2013 | |
| KR | 10-2006-0114355 A | 11/2006 | |
| WO | WO 92/07615 | 5/1992 | |
| WO | WO 98/21312 | 5/1998 | |
| WO | WO 2003/082201 A2 | 10/2003 | |
| WO | WO 2005/001072 A1 | 1/2005 | |
| WO | WO 2005/081970 A2 | 9/2005 | |
| WO | WO 2005/097974 A2 | 10/2005 | |
| WO | WO 2005/113747 A2 | 12/2005 | |
| WO | WO 2006/126236 A1 | 11/2006 | |
| WO | WO 2008/075339 A2 | 6/2008 | |
| WO | WO 2009/022907 A2 | 2/2009 | |
| WO | WO-2009086596 A1 | 7/2009 | |
| WO | WO 2009/146911 A2 | 12/2009 | |
| WO | WO 2010/008905 A2 | 1/2010 | |
| WO | WO 2010/090513 A2 | 8/2010 | |
| WO | WO 2010/094694 A1 | 8/2010 | |
| WO | WO 2010/127399 A1 | 11/2010 | |
| WO | WO 2010/143747 A1 | 12/2010 | |
| WO | WO-2011116930 A1 | 9/2011 | |
| WO | WO 2011/139628 A1 | 11/2011 | |
| WO | WO 2011/140441 A2 | 11/2011 | |
| WO | WO 2012/014076 A2 | 2/2012 | |
| WO | WO 2012/027474 A1 | 3/2012 | |
| WO | WO 2012/089669 A1 | 7/2012 | |
| WO | WO 2012/118799 A2 | 9/2012 | |
| WO | WO 2012/154834 A1 | 11/2012 | |
| WO | WO 2012/155110 A1 | 11/2012 | |
| WO | WO 2012/166903 A1 | 12/2012 | |
| WO | WO 2012/168930 A2 | 12/2012 | |
| WO | WO 2012/178215 A1 | 12/2012 | |
| WO | WO 2013/040087 A2 | 3/2013 | |
| WO | WO 2013/067498 A1 | 5/2013 | |
| WO | WO 2013/086486 A1 | 6/2013 | |
| WO | WO 2013/086502 A1 | 6/2013 | |
| WO | WO 2013/093812 A2 | 6/2013 | |
| WO | WO 2013/096741 A2 | 6/2013 | |
| WO | WO 2013/127921 A1 | 9/2013 | |
| WO | WO 2013/155060 A1 | 10/2013 | |
| WO | WO 2013/174794 A1 | 11/2013 | |
| WO | WO 2013/192290 A1 | 12/2013 | |
| WO | WO 2014/013334 A2 | 1/2014 | |
| WO | WO 2014/048637 A1 | 4/2014 | |
| WO | WO 2014/053596 A1 | 4/2014 | |
| WO | WO 2014/082096 A1 | 5/2014 | |
| WO | WO 2014/090993 A1 | 6/2014 | |
| WO | WO 2014/127170 A1 | 8/2014 | |
| WO | WO 2014/151921 A1 | 9/2014 | |
| WO | WO 2014/153230 A1 | 9/2014 | |
| WO | WO 2014/153294 A1 | 9/2014 | |
| WO | WO 2014/159356 A1 | 10/2014 | |
| WO | WO 2014/173907 A1 | 10/2014 | |
| WO | WO-2014159356 A1 * | 10/2014 | ........... C12N 5/0679 |
| WO | WO 2014/182885 A2 | 11/2014 | |
| WO | WO 2014/197934 A1 | 12/2014 | |
| WO | WO 2014/199622 A1 | 12/2014 | |
| WO | WO 2015/021358 A2 | 2/2015 | |
| WO | WO 2015/060790 A1 | 4/2015 | |
| WO | WO 2015/075175 A1 | 5/2015 | |
| WO | WO 2015/076388 A1 | 5/2015 | |
| WO | WO 2015/108893 A1 | 7/2015 | |
| WO | WO 2015/123183 A1 | 8/2015 | |
| WO | WO 2015/129822 A1 | 9/2015 | |
| WO | WO 2015/130919 A1 | 9/2015 | |
| WO | WO 2015/135893 A1 | 9/2015 | |
| WO | WO 2015/138032 A2 | 9/2015 | |
| WO | WO 2015/152954 A1 | 10/2015 | |
| WO | WO 2015/156929 A1 | 10/2015 | |
| WO | WO 2015/157163 A1 | 10/2015 | |
| WO | WO 2015/168022 A1 | 11/2015 | |
| WO | WO 2015/0173425 A1 | 11/2015 | |
| WO | WO 2015/184273 A1 | 12/2015 | |
| WO | WO 2015/184375 A1 | 12/2015 | |
| WO | WO 2015/185714 A1 | 12/2015 | |
| WO | WO 2015/189320 A2 | 12/2015 | |
| WO | WO 2015/196012 A1 | 12/2015 | |
| WO | WO 2015/200901 A1 | 12/2015 | |
| WO | WO-2015183920 A2 * | 12/2015 | ........... C12N 5/0697 |
| WO | WO 2016/011377 A1 | 1/2016 | |
| WO | WO 2016/015158 A1 | 2/2016 | |

(56) References Cited

FOREIGN PATENT DOCUMENTS

| | | |
|---|---|---|
| WO | WO 2016/030525 A1 | 3/2016 |
| WO | WO 2016/033163 A1 | 3/2016 |
| WO | WO 2016/057571 A1 | 4/2016 |
| WO | WO 2016/061464 A1 | 4/2016 |
| WO | WO-2016056999 A1 | 4/2016 |
| WO | WO 2016/073989 A2 | 5/2016 |
| WO | WO 2016/083612 A1 | 6/2016 |
| WO | WO 2016/083613 A2 | 6/2016 |
| WO | WO 2016/085765 A1 | 6/2016 |
| WO | WO 2016/094948 A1 | 6/2016 |
| WO | WO 2016/103002 A1 | 6/2016 |
| WO | WO 2016/103269 A1 | 6/2016 |
| WO | WO 2016/121512 A1 | 8/2016 |
| WO | WO 2016/140716 A1 | 9/2016 |
| WO | WO 2016/141137 A1 | 9/2016 |
| WO | WO 2016/144769 A1 | 9/2016 |
| WO | WO 2016/164413 A1 | 10/2016 |
| WO | WO 2016/168950 A1 | 10/2016 |
| WO | WO 2016/174604 A1 | 11/2016 |
| WO | WO 2016/176208 A1 | 11/2016 |
| WO | WO 2016/183143 A1 | 11/2016 |
| WO | WO 2016/193441 A2 | 12/2016 |
| WO | WO 2016/207621 A1 | 12/2016 |
| WO | WO 2016/210313 A1 | 12/2016 |
| WO | WO 2016/210416 A2 | 12/2016 |
| WO | WO 2017/009263 A1 | 1/2017 |
| WO | WO 2017/036533 A1 | 3/2017 |
| WO | WO 2017/037295 A1 | 3/2017 |
| WO | WO 2017/041041 A1 | 3/2017 |
| WO | WO 2017/048193 A1 | 3/2017 |
| WO | WO 2017/048322 A1 | 3/2017 |
| WO | WO 2017/049243 A1 | 3/2017 |
| WO | WO 2017/059171 A1 | 4/2017 |
| WO | WO 2017/060884 A1 | 4/2017 |
| WO | WO 2017/066507 A1 | 4/2017 |
| WO | WO 2017/066659 A1 | 4/2017 |
| WO | WO 2017/070007 A2 | 4/2017 |
| WO | WO 2017/070224 A1 | 4/2017 |
| WO | WO 2017/070471 A1 | 4/2017 |
| WO | WO 2017/070506 A1 | 4/2017 |
| WO | WO-2017070337 A1 | 4/2017 |
| WO | WO 2017/075389 A1 | 5/2017 |
| WO | WO 2017/077535 A1 | 5/2017 |
| WO | WO 2017/079632 A1 | 5/2017 |
| WO | WO 2017/083705 A1 | 5/2017 |
| WO | WO 2017/096192 A1 | 6/2017 |
| WO | WO 2017/096282 A1 | 6/2017 |
| WO | WO 2017/112901 A1 | 6/2017 |
| WO | WO 2017/115982 A1 | 7/2017 |
| WO | WO 2017/117333 A1 | 7/2017 |
| WO | WO 2017/117547 A1 | 7/2017 |
| WO | WO 2017/117571 A1 | 7/2017 |
| WO | WO 2017/120543 A1 | 7/2017 |
| WO | WO 2017/121754 A1 | 7/2017 |
| WO | WO 2017/123791 A1 | 7/2017 |
| WO | WO 2017/136462 A2 | 8/2017 |
| WO | WO 2017/136479 A1 | 8/2017 |
| WO | WO 2017/139455 A1 | 8/2017 |
| WO | WO 2017/139638 A1 | 8/2017 |
| WO | WO 2017/142069 A1 | 8/2017 |
| WO | WO 2017/143100 A1 | 8/2017 |
| WO | WO 2017/149025 A1 | 9/2017 |
| WO | WO 2017/153992 A1 | 9/2017 |
| WO | WO 2017/160234 A1 | 9/2017 |
| WO | WO 2017/160671 A1 | 9/2017 |
| WO | WO 2017/172638 A1 | 10/2017 |
| WO | WO 2017/174609 A1 | 10/2017 |
| WO | WO 2017/176810 A1 | 10/2017 |
| WO | WO 2017/184586 A1 | 10/2017 |
| WO | WO-2017175876 A1 | 10/2017 |
| WO | WO 2017/192997 A1 | 11/2017 |
| WO | WO 2017/205511 A1 | 11/2017 |
| WO | WO 2017/218287 A1 | 12/2017 |
| WO | WO 2017/220586 A1 | 12/2017 |
| WO | WO 2018/011558 A1 | 1/2018 |
| WO | WO 2018/019704 A1 | 2/2018 |
| WO | WO 2018/026947 A1 | 2/2018 |
| WO | WO 2018/027023 A1 | 2/2018 |
| WO | WO 2018/027112 A1 | 2/2018 |
| WO | WO 2018/035574 A1 | 3/2018 |
| WO | WO 2018/038042 A1 | 3/2018 |
| WO | WO 2018/044685 A1 | 3/2018 |
| WO | WO 2018/044885 A1 | 3/2018 |
| WO | WO 2018/044937 A2 | 3/2018 |
| WO | WO 2018/044940 A1 | 3/2018 |
| WO | WO 2018/085615 A1 | 5/2018 |
| WO | WO 2018/094522 A1 | 5/2018 |
| WO | WO 2018/106628 A1 | 6/2018 |
| WO | WO-2018115852 A1 | 6/2018 |
| WO | WO 2018/197544 A1 | 11/2018 |
| WO | WO 2019/074793 A1 | 4/2019 |

OTHER PUBLICATIONS

Bernstein, B.E., et al., "The NIH Roadmap Epigenomics Mapping Consortium," Nat Biotechnol. 2010; 28(10):1045-1048, 9 pgs.

Beuling, E., et al., "Co-Localization of Gata4 and Hnf1α in the Gastrointestinal Tract is Restricted to the Distal Stomach and Proximal Small Intestine," Gastroenterology, AGA Abstracts, Abstract T1933, 2007a, 132:A586, 1 pg.

Beuling, E., et al., "Conditional Gata4 deletion in mice induces bile acid absorption in the proximal small intestine," Gut, 2010, 59(7):888-895, 19 pgs.

Beuling, E., et al., "Fog Cofactors Partially Mediate Gata4 Function in the Adult Mouse Small Intestine," Gastroenterology, AGA Abstacts, Abstact W1467, 2007b, 132:A692-A693, 2 pgs.

Beuling, E., et al., "GATA4 mediates gene repression in the mature mouse small intestine through interactions with Friend of GATA (FOG) cofactors," Dev Biol, 2008a, 322(1):179-189, 23 pgs.

Beuling, E., et al., "The Absence of GATA4 in the Distal Small Intestine Defines the Ileal Phenotype," Gastroenterology, ABA Abstact, Abstract 602, 2008b, 134:A83-A84, 2 pgs.

Bonilla-Claudio, M., et al., "Bmp signaling regulates a dose-dependent transcriptional program to control facial skeletal development," Development, 2012, 139:709-719, 11 pgs.

Bosse, T., et al., "Gata4 and Hnf1α are partially required for the expression of specific intestinal genes during development," Am J Physiol Gastrointest Liver Physiol, 2007, 292:G1302-G1314, 13 pgs.

Bouchi, R., et al., "FOXO1 Inhibition Yields Functional Insulin-Producing Cells In Human Gut Organoid Cultures," Nat Commun, 2014, 5:4242, 24 pgs.

Burnicka-Turek, O., et al., "INSL5-Deficient Mice Display an Alteration in Glucose Homeostasis and an Impaired Fertility," Endocrinology, Oct. 2012, 153(10):4655-4665, 11 pgs.

Choi, E., et al., "Cell lineage distribution atlas of the human stomach reveals heterogeneous gland populations in the gastric antrum," Gut, 2014, 63(11):1711-1720, 20 pgs.

Choi, E., et al., "Expression of Activated Ras in Gastric Chief Cells of Mice Leads to the Full Spectrum of Metaplastic Lineage Transitions," Gastroenterology, Apr. 2016, 150(4):918-930, 23 pgs.

De Santa Barbara, P., et al., "Bone Morphogenetic Protein Signaling Pathway Plays Multiple Roles During Gastrointestinal Tract Development," Developmental Dynamics, 2005, 234:312-322, 11 pgs.

Dobreva, G., et al., "SATB2 Is a Multifunctional Determinant of Craniofacial Patterning and Osteoblast Differentiation," Cell, 2006, 125:971-986, 16 pgs.

Driver, I., et al., "Specification of regional intestinal stem cell identity during *Drosophila metamorphosis*," Development, 2014, 141:1848-1856, 9 pgs.

Duluc, I., et al., "Fetal Endoderm Primarily Holds the Temporal and Positional Information Required for Mammalian Intestinal Development," The Journal of Cell Biology, 1994, 126(1):211-221, 11 pgs.

Fagerberg, L., et al., "Analysis of the Human Tissue-specific Expression by Genome-wide Integration of Transcriptomics and Antibody-based Proteomics," Mol Cell Proteomics, 2014, 13:397-406, 10 pgs.

(56) References Cited

OTHER PUBLICATIONS

Finkbeiner, S.R., et al., "Transcriptome-wide Analysis Reveals Hallmarks of Human Intestine Development and Maturation In Vitro and In Vivo," Stem Cell Reports, 2015, 4:1140-1155, 16 pgs.

Fitzpatrick, D.R., et al., "Identification SATB2 as the cleft palate gene on 2q32-q33," Human Molecular Genetics, 2003, 12(19):2491-2501, 11 pgs.

Genthe, J.R., et al., "Ventromorphins: A new class of small molecule activators of the canonical BMP signaling pathway," ACS Chem Biol, 2017, 12(9):2436-2447, 21 pgs.

Georgas, K.M., et al., "An illustrated anatomical ontology of the developing mouse lower urogenital tract," Development 2015, 142:1893-1908, 16 pgs.

Ginestet, C., Book Review in the Journal of the Royal Statistical Society. Series A (Statistics in Society) (2011), of ggplot2: Elegant of the Gastric for Data Analysis, by H. Wickham, 2009; 174(1):245, 2 pgs.

Goldenring, J.R., et al., "Differentiation of the Gastric Mucosa: III. Animal models of oxyntic atrophy and metaplasia," Am J Physiol Gastrointestinal and Liver Physiol, 2006, 291:G999-G1004, 6 pgs.

Goldenring, J.R., et al., "Overexpression of Transforming Growth Factor-α Alters Differentiation of Gastric Cell Lineages," Dig. Dis. Sci., 1996, 41(4):773-784, 12 pgs.

Guo, Z., et al., "Injury-induced BMP signaling negatively regulated *Drosophila midgut* homeostasis," J Cell Biol., 2013, 201(6):945-961, 17 pgs.

Gyorgy, A.B., et al., "SATB2 interacts with chromatin-remodeling molecules in differentiating cortical neurons," European Journal of Neuroscience, 2008, 27:865-873, 9 pgs.

Haramis, A-P.G., et al., "De Novo Crypt Formation and Juvenile Polyposis on BMP Inhibition in Mouse Intestine," Science, 2004, 303:1684-1686, 4 pgs.

Hardwick, J.C.H., et al., "Bone Morphogenetic Protein 2 Is Expressed by, and Acts Upon, Mature Epithelial Cells in the Colon," Gastroenterology, 2004, 126:111-121, 11 pgs.

He, X.C., et al., "BMP signaling inhibits intestinal stem cell self-renewal through suppression of Wnt-β-catenin signaling," Nature Genetics, 2004, 36(10):1117-1121, 5 pgs.

Higuchi, Y., et al., "Gastrointestinal Fibroblasts Have Specialized, Diverse Transcriptional Phenotypes: A Comprehensive Gene Expression Analysis of Human Fibroblasts," PloS One, Jun. 2015, 10(6):e0129241, 19 pgs.

Hoffmann, W., "Current Status on Stem Cells and Cancers of the Gastric Epithelium," Int. J. Mol. Sci., 2015, 16:19153-19169, 17 pgs.

Holland, P.W.H., et al., "Classification and nomenclature of all human homebox genes," BMC Biology, 2007, 5:47, 29 pgs.

Huh, W.J., et al., "Ménétrier's Disease: Its Mimickers and Pathogenesis," Journal of Pathology and Translational Medicine, 2016; 50:10-16, 7 pgs.

Jeejeebhoy, K.N., "Short bowel syndrome: a nutritional and medical approach," CMAJ, 2002, 166(10):1297-1302, 6 pgs.

Johnston, T.B., et al., "Extroversion of the Bladder, Complicated by the Presence of Intestinal Openings on the Surface of Intestinal Openings on the Surface of the Extroverted Area," J Anat Physiol, 1913, 48(Pt 1):89-106, 18 pgs.

Keeley, T.M., et al., "Cytodifferentiation of the postnatal mouse stomach in normal and Huntingtin-interacting protein 1-related-deficient mice," Am. J. Physiol. Gastrointest. Liver Physiol., 2010, 299:G1241-G1251, 11 pgs.

Kim, B-M., et al., "Regulation of mouse stomach development and Barx1 expression by specific microRNAs," Development, 2011, 138:1081-1086, 6 pgs.

Kim, B-M., et al., "The Stomach Mesenchymal Transcription Factor Barx1 Specifies Gastric Epithelial Identity through Inhibition of Transient Wnt Signaling," Developmental Cell, 2005, 8:611-622, 12 pgs.

Kohlnhofer, B.M., et al., "GATA4 Regulates Epithelial Cell Proliferation to Contron Intestinal Growth and Development in Mice," Cellular and Molecular Gastroenterology and Hepatology, 2016, 2(2):189-209, 21 pgs.

Kraus, M.R.C., et al., "Patterning and shapiing the endoderm in vivo and in culture," Current Opinion Genetics & Development., 2012, 22:347-353, 7 pgs.

Lambrecht, N.W.G., et al., "Identification of the K efflux channel coupled to the gastric H—K-ATPase during acid secretion," Physiological Genomics, 2005, 21:81-91, 11 pgs.

Lameris, A.L., et al., "Expression profiling of claudins in the human gastrointestinal tract in health and during inflammatory bowel disease," Scandinavian Journal of Gastroenterology, 2013, 48:58-69, 12 pgs.

Langmead, G., et al., "Ultrafast and memory-efficient alignment of short DNA sequences to the human genome," Genome Biology, 2009, 10:R25, 10 pgs.

Lennerz, J.K.M., et al., "The Transcription Factor MIST1 Is a Novel Human Gastric Chief Cell Marker Whose Expression Is Lost in Metaplasia, Dyslasia, and Carcinoma," The American Journal of Pathology, 2010, 177(3):1514-1533, 20 pgs.

Li, H., et al., "TreeFam: a curated database of phylogenetic trees of animal gene families," Nucleic Acids Research, 2006, 34:D572-D580, 9 pgs.

Li, L., "BMP Signaling Inhibits Intestinal Stem Cell Self-Renewal Through Antagonizing Wnt Signaling," Gastroenterology, AASLD Abstacts, Abstract S1223, 2005, 128:A702, 1 pg.

McGovern, D.P.B., et al., "Genome-wide association identifies multiple ulcerative colitis susceptibility loci," Nature Genetics, 2010, 42(4):332-337, 8 pgs.

Molodecky, N.A., et al., "Increasing Incidence and Prevalence of the Inflammatory Bowel Diseases With Time, Based on Systematic Review," Gastroenterology, 2012, 142:46-54, 51 pgs.

Moser, A.R., et al., "A dominant mutation that predisposes to multiple intestinal neoplasia in the mouse," Science, 1990, 247(4940):322-324, 3 pgs.

Nielsen, C., et al., "Gizzard Formation and the Role of Bapx1," Development Biology, 2001, 231:164-174, 11 pgs.

Nomura, S., et al., "Evidence for Repatterning ot the Gastric Fundic Epithelium Associated With Ménétrier's Disease and TGFα Overexpression," Gastroenterology, 2005, 128:1292-1305, 14 pgs.

Park, Y.H., et al., "Review of Atrophic Gastritis and Intestinal Metaplasia as a Premalignant Lesion of Gastric Cancer," Journal of Cancer Prevention, 2015, 20(1):25-40, 16 pgs.

Patankar, J.V., et al., "Intestinal Deficiency of Gata4 Protects from Diet-Induced Hepatic Steatosis by Suppressing De Novo Lipogenesis and Gluconeogenesis in Mice," Journal of Hepatology, Posters, Abstract 1253, 2012, 56:S496, 1 pg.

Patankar, J.V., et al., "Intestinal GATA4 deficiency protects from diet-induced hepatic steatosis," Journal of Hepatology, 2012, 57:1061-1068, 8 pgs.

Ramalingam, S., et al., "Distinct levels of Sox9 expression mark colon epithelial stem cells that form colonoids in culture," Am J Physiol Gastrointest Liver Physiol,, 2012, 302:G10-G20, 11 pgs.

Ramsey, V.G., et al., "The maturation of mucus-secreting gastric epithelial progenitors into digestive-enzyme secreting zymogenic cells requires Mist1," Development, 2007, 134:211-222, 12 pgs.

Rankin, S.A., et al., "A Molecular Atlas of Xenopus Respiratory System Development," Developmental Dynamics, 2015, 244:69-85, 17 pgs.

Rankin, S.A., et al., "Suppression of Bmp4 signaling by the zinc-finger repressors Osr1 and Osr2 is required for Wnt/β-catenin-mediated lung specification in Xenopus," Development, 2012, 139:3010-3020, 11 pgs.

Ratineau, C., et al., "Endoderm- and mesenchyme-dependant commitment of the differentiated epithlial cell types in the developing intestine of rat," Differentiation, 2003, 71:163-169, 7 pgs.

Roberts, D.J., et al., "Sonic hedgehog is an endodermal signal inducing Bmp-4 and Hox genes during induction and regionalization of the chick hindgut," Development, 1995, 121:3163-3174, 12 pgs.

Rodríguez-Piñeiro, A.M., et al., "Studies of mucus in mouse stomach, small intestine, and colon. II. Gastrointestinal mucus proteome

(56) References Cited

OTHER PUBLICATIONS reveals Muc2 and Muc5ac accompanied by a set of core proteins," Am J Physiol Gastrointest Liver Physiol, 2013, 305:G348-G356, 9 pgs.
Rodriquez, P., et al., "BMP signaling in the development of the mouse esophagus and forestomach," Development, 2010, 137:4171-4176, 6 pgs.
Roth, R.B., et al., "Gene expression analyses reveal molecular relationships among 20 regions of the human CNS," Neurogenetics, 2006, 7:67-80, 14 pgs.
Savidge, T.C., et al., "Human intestinal development in a severe-combined immunodeficient xenograft model," Differentiation, 1995, 58:361-371, 11 pgs.
Savin, T., et al., "On the growth and form of the gut," Nature, 2011, 476:57-62, 7 pgs.
Schumacher, M.A., et al., "The use of murine-derived fundic organoids in studies of gastric physiology," J. Physiol., 2015, 593(8):1809-1827, 19 pgs.
Sheehan-Rooney, K., et al., "Bmp and Shh Signaling Mediate the Expression of satb2 in the Pharyngeal Arches," PLoS One, Mar. 2013, 8(3):e59533, 10 pgs.
Sherwood, R.I., et al., "Transcriptional dynamics of endodermal organ formation," Dev Dyn, 2009, 238(1):29-42, 23 pgs.
Sherwood, R.I., et al., "Wnt signaling specifies and patterns intestinal endoderm," Mechanisms of Development, 2011, 128:387-400, 14 pgs.
Shyer, A.E., et al., "Bending Gradients: How the Intestinal Stem Cell Gets Its Home," Cell, 2015, 161:569-580, 13 pgs.
Siegel, R., et al., "Colorectal Cancer Statistics, 2014," CA Cancer J Clin, 2014. 64:104-117, 14 pgs.
Sigalet, D.L., "The Role of the Enteric Neuronal System In Controlling Intestinal Function," Clinical Surgery Society Magazine, 2003, 64:214. (Reference unavailable).
Speer, A.L., et al., "Fibroblast Growth Factor 10-Fibroblast Growth Factor Receptor 2b Mediated Signaling Is Not Required for Adult Glandular Stomach Homeostasis," PLoS ONE, 2012, 7(11):e49127, 12 pgs.
Stange, D.E., et al., "Differentiated Troy+ chief cells act as 'reserve' stem cell to generate all lineages of the stomach epithelium," Cell, 2013, 155(2):357-368, 26 pgs.
Thanasupawat, T., et al., "INSL5 is a novel marker for human enteroendocrine cells of the large intestine and neuroendocrine tumours," Oncology Reports, 2013, 29:149-157, 6 pgs.
Trapnell, C., et al., "Differential gene and transcript expression analysis of RNA-seq experiments with TopHat and Cufflinks," Nat Protoc, 2013, 7(3):562-578, 39 pgs.
Uppal, K., et al., "Meckel's Diverticulum: A Review," Clinical Anatomy, 2011, 24: 416-422, 7 pgs.
Van Dop, W.A., et al., "Depletion of the Colonic Epithelial Precursor Cell Compartment Upon Conditional Activation of the Hedgehog Pathway," Gastroenterology, 2009, 136:2195-2203, 16 pgs.
Van Klinken, B.J-W., et al., "MUC5B is the prominent mucin in human gallbladder and is also expressed in a subset of colonic goblet cells," The American Journal of Physiology, 1998, 274:G871-G878, 8 pgs.
Walker, E.M., et al., "GATA4 and GATA6 regulate intestinal epithelial cytodifferentiation during development," Development Biology, 2014, 392:283-294, 12 pgs.
Walton, K.D., et al., "Epithelial Hedgehog signals direct mesenchymal villus patterning through BMP," Abstacts / Development Biology, Program/Abstact # 354, 2009, 331:489, 1 pg.
Walton, K.D., et al., "Hedgehog-responsive mesenchymal clusters direct patterning emergence of intestinal villi," PNAS, 2012, 109(39):15817-15822, 6 pgs.
Walton, K.D., et al., "Vilification in the mouse: Bmp signals control intestinal villus patterning," Development, 2016, 143:427-436, 10 pgs.
Wang, X., et al., "Cloning and variation of ground state intestinal stem cells," Nature, 2015, 522:173-178, 18 pgs.
Wehkamp, J., et al., "Paneth cell antimicrobial peptides: Topographical distribution and quantification in human gastrointestinal tissues," FEBS Letters, 2006, 580:5344-5350, 7 pgs.
Weis, V.G., et al., "Current understanding of SPEM and its standing in the preneoplastic process," Gastric Cancer, 2009, 12:189-197, 9 pgs.
Whissell, G., et al., "The transcription factor GATA6 enables self-renewal of colon adenoma stem cells by repressing BMP gene expression," Nature Cell Biology, 2014, 16(7):695-707, 24 pgs.
Wills, A., et al., "Bmp signaling is necessary and sufficient for ventrolateral endoderm specification in Xenopus," Dev Dyn., 2008, 237:2177-2186, 18 pgs.
Xue, X., et al., "Endothelial PAS Domain Protein 1 Activates the Inflammatory Response in the Intestinal Epithelium to Promote Colitis in Mice," Gastroenterology, 2013, 145:831-841, 11 pgs.
Yahagi, N., et al., "Position-specific expression of Hox genes along the gastrointestinal tract," Congenital Anomalies, 2004, 44:18-26, 9 pgs.
Zbuk, K.M., et al., "Hamartomatous polyposis syndroms," Gastroenterology & Hepatology, 2007, 4(9):492-502, 12 pgs.
Japanese Office Action, Notification of Reasons for Refusal, and First Search Report by Registered Search Organization, dated May 14, 2019 for Application JP 2017-520900, 65 pgs.
Japanese Office Action, Notice of Reasons for Refusal, and Search Report by Registered Search Organization, dated Apr. 2, 2019 for Application No. JP 2016-569618, 42 pgs.
Singaporean Office Action, Third Written Opinion, dated May 3, 2019 for Application No. SG 11201609953X, 5 pgs.
Buta, C., et al., "Reconsidering pluripotency tests: Do we still need teratoma assays?" Stem Cell Research, 2013, 11:552-562, 11 pgs.
Fon Tacer, K., et al., "Research Resource: Comprehensive Expression Atlas of the Fibroblast Growth Factor System in Adult Mouse," Mol Endocrinol, Oct. 2010, 24(10):2050-2064, 15 pgs.
Gomez, M.C., et al., "Derivation of cat embryonic stem-like cells from in vitro-produced blastocysts on homologous and heterologous feeder cells," Theriogenology, 2010, 74:498-515, 18 pgs.
Jean, C., et al., "Pluripotent genes in avian stem cells," Develop Growth Differ, 2013, 55:41-51, 11 pgs.
Ornitz, D.M., et al., "The Fibroblast Growth Factor signaling pathway," WIREs Dev Biol, 2015, 4:215-266, 52 pgs.
Prakash, R., "Regulation of WNT Genes in Stem Cells Development and Organogenesis," IJP, Jun. 2014, 1(6):366-372, 7 pgs.
International Search Report and Written Opinion dated Sep. 28, 2018 for Application No. PCT/US2018/029083, 14 pgs.
U.S. Appl. No. 62/730,061, filed Sep. 12, 2018.
Ajmera, V., et al., "Novel Plasma Biomarkers Associated with Liver Disease Severity in Adults with Nonalcoholic Fatty Liver Disease," Hepatology, 2017, 65(1):65-77, 21 pgs.
Aleo, M.D., et al., "Human Drug-Induced Liver Injury Severity is Highly Associated with Dual Inhibition of Liver Mitochondrial Function and Bile Salt Export Pump," Hepatology, 2014, 60:1015-1022, 8 pgs.
Allard, J., et al., "Immunohistochemical toolkit for tracking and quantifying xenotransplanted human stem cells," Regenerative Medicine, 2014, 9(4):437-452, 11 pgs.
Arroyo, J.D., et al., "Argonaute2 complexes carry a population of circulating microRNAs independent of vescicles in human plasma," PNAS, 2011, 108(12):5003-5008, 6 pgs.
Bahar Halpern, K., et al. "Single-cell spatial reconstruction reveals global division of labour in the mammalian liver," Nature, 2017, 542:352-356, 18 pgs.
Bar-Ephraim, Y.E., et al., "Modelling cancer immunomodulation using epithelial organoid cultures," bioRxiv, 2018, accessed from Http://dx.doi.org/10.1101/377655v1.full, 13 pgs.
Barth, C.A., et al., "Transcellular transport of fluorescein in hepatocyte monolayers: Evidence for functional polarity of cells in culture," Proc Natl Sci USA, 1982, 79:4985-4987, 3 pgs.
Begriche, K., et al., "Drug-induced toxicity on mitochondria and lipid metabolism: Mechanistic diversity and deleterious consequences for the liver," J Hepatol, 2011, 54:773-794, 22 pgs.
Bell, L.N., et al., "Epidemiology of Idiosyncratic Drug-Induced Liver Injury," Semin Liver Dis, 2009, 29(4):337-347, 11 pgs.

(56) References Cited

OTHER PUBLICATIONS

Bergeles, C., et al., "From Passive Tool Holders to Microsurgeons: Safer, Smaller, Smarter Surgical Robots," IEEE Trans Biomed Eng, 2014, 61(5):1565-1576, 12 pgs.

Bernardi, P., "The permeability transition pore. Control points of a cyclosporin A-sensitive mitochondrial channel involved in cell death," Biochim Biophys Acta, 1996, 1275:5-9, 5 pgs.

Bharadwaj, S., et al., "Current status of intestinal and multivisceral transplantation," Gastroentrerol Rep (Oxf)., 2017, 5(1):20-28, 9 pgs.

Bhutani, N., et al., Reprogramming towards pluripotency requires AID-dependent DNA demethylation, Nature, 2010, 463(7284):1042-1047, 17 pgs.

Bohan, T.P., et al., "Effect of L-carnitine treatment for valproate-induced hepatotoxicity," Neurology, 2001, 56:1405-1409, 5 pgs.

Boroviak, T., et al., "Single cell transcriptome analysis of human, marmoset and mouse embryos reveals common and divergent features of preimplantation development," Development, 2018, 145(21):dev167833, 35 pgs.

Bort, R., et al., "Diclofenac Toxicity to Hepatocytes: A Role for Drug Metabolism in Cell Toxicity," J Pharmacol Exp Ther, 1998, 288(1):65-72, 8 pgs.

Boullata, J.I., et al. "A.S.P.E.N. Clinical Guidelines: Parenteral Nutrition Ordering, Order Review, Compounding, Labeling, and Dispensing," J Parenter Enteral Nutr, 2014, 38(3):334-377, 44 pgs.

Bragdon, B., et al., "Bone Morphogenetic Proteins: A critical review," Cellular Signalling, 2011, 23:609-620, 12 pgs.

Bravo, P., et al., "Efficient In Vitro Vectorial Transport of a Fluorescent Conjugated Bile Acid Analogue by Polarized Hepatic Hybrid WIF-B and WIF-B9 Cells," Hepatology, 1998, 27:576-583, 8 pgs.

Broda, T.R., et al., "Generation of human antral and fundic gastric organoids from pluripotent stem cells," Nature Protocols, Nov. 2018, 14(1):28-50, 23 pgs., XP036660403.

Browning, J.D., et al., "Molecular mediators of hepatic steatosis and liver injury," J Clin Invest, 2004, 114(2):147-152, 6 pgs.

Burke, P., et al., "Towards a single-chip, implantable RFID system: is a single-cell radio possible?" Biomed Microdevices, 2010, 12:589-596, 8 pgs.

Burn, S.F., et al., "Left-right asymmetry in gut development: what happens next?" BioEssays, 2009, 31:1026-1037, 12 pgs.

Caneparo, L., et al., "Intercellular Bridges in Vertebrate Gastrulation," PloS ONE, 2011, 6(5):e20230, 6 pgs.

Capeling, M.M., et al., "Nonadhesive Alignate Hydrogels Support Growth of Pluripotent Stem Cell-Derived Intestinal Organoids," Stem Cell Reports, Feb. 2019, 12(2):381-394, 14 pgs.

Chai, P.R., et al., "Utilizing an Ingestible Biosensor to Assess Real-Time Medication Adherence," J Med Toxicol, 2015, 11:439-444, 6 pgs.

Chai, P.R., et al., "Ingestible Biosensors for Real-Time Medical Adherence Monitoring: MyTMed," Proc Annu Hawaii Int Conf Syst Sci, Jan. 2016, 2016:3416-3423, 12 pgs.

Chang, J.H., et al., "Evaluating the In Vitro Inhibition of UGT1A1, OATP1B1, OATP1B3, MRP2, and BSEP in Predicting Drug-Induced Hyperbilirubinemia," Mol Pharm, 2013, 10:3067-3075, 9 pgs.

Chatterjee, S., et al., "Hepatocyte-based in vitro model for assemssment of drug-induced cholestasis," Toxicol Appl Pharmacol, 2014, 274:124-136, 13 pgs.

Chen, B., et al., "Dynamic Imaging of Genomic Loci in Living Human Cells by an Optimized CRISPR/Cas System," Cell, 2013, 155(7):1479-1491, 23 pgs.

Chen, L.Y., et al., "Mass fabrication and delivery of 3D multilayer μ Tags into living cells," Sci Rep, 2013, 3:2295, 6 pgs.

Chen, Y., et al., "Retinoic acid signaling is essential for pancreas development and promotes endocrine at the expense of exocrine cell differentiation in *Xenopus*," Dev Biol, 2004, 271:144-160, 17 pgs.

Christofflrsson, J., et al., "Developing organ-on-a-chip concepts using bio-mechatronic design methodology," Biofabrication, 2017, 9:025023, 14 pgs.

Chughlay, M.F., et al., "N-acetylcysteine for non-paracetamol drug-induced liver injury: a systematic review," Br J Clin Pharmacol, 2016, 81:1021-1029, 9 pgs.

Cincinnati Children'S Hospital Medical Center, "Scientists grow human esophagus in lab: Tiny organoids enable personalized disease diagnosis, regenerative therapies," CCHMC Public Press Release, Sep. 20, 2018, 2 pgs.

Clarke, L.L., "A guide to Ussing chamber studies of mouse intestine," Am J Physiol Gastrointest Liver Physiol, 2009, 296:G1151-G1166, 16 pgs.

Collier, A.J., et al., "Comprehensive Cell Surface Protein Profiling Identifies Specific Markers of Human Naïve and Primed Pluripotent States," Cell Stem Cell, 2017, 20:874-890, 25 pgs.

Cortez, et al., "Transplantation of human intestinal organoids into the mouse mesentery: A more physiological and anatomic engratment site," Surgery, 2018, 164:643-650, 8 pgs.

Crespo, M., et al., "Colonic organoids derived from human induced pluripotent stem cells for modeling colorectal cancer and drug testing," Natrue Medicine, 2017, 23(7):878-884, 11 pgs.

Crocenzi, F.A., et al., "$Ca^{2+}$-Dependent Protein Kinase C Isoforms are Critical to Estradiol 17β-D-Glucuronide-Induced Chloestasis in the Rat," Hepatology, 2008, 48:1885-1895, 12 pgs.

Cutrin, J.C., et al., "Reperfusion Damage to the Bile Canaliculi in Transplanted Human Liver," Hepatology, 1996, 24:1053-1057, 5 pgs.

Das, R., "RFID Forecasts, Players and Opportunities 2017-2027," IDTechEx, 2017, downloaded from https://www.idtechex.com/en/research-report/rfid-forecasts-players-and-opportunities-2017-2027/546, 8 pgs. Summary only.

Dash, A., et al., "Pharmacotoxicology of clinically-relevant concentrations of obeticholic acid in an organotypic human hepatocyte system," Toxicology In Vitro, 2017, 39:93-103, 11 pgs.

Davidson, M.D., et al., "Long-term exposure to abnormal glucose levels alters drug metabolism pathways and insulin sensitivity in primary human hepatocytes," Sci Rep, 2016, 6:28178, 11 pgs.

Dekkers, J.F., et al., "A functional CFTR assay using primary cystic fibrosis intestinal organoids," Nat Med, 2013, 19(7):939-945, 9 pgs.

Demehri, F.R., et al., "Development of endoluminal intestinal attachment for clinically applicable distraction enterogenesis device," Journal of Pediatric Surgery, 2016, 51:101-106, 6 pgs.

Demehri, F.R., et al., "Development of an endoluminal intestinal lengthening device using a geometric intestinal attachment approach," Surgery, 2015, 158(3):802-811, 10 pgs.

Dumortier, G., et al., "Tolérance hépatique des antipsychotiques atypiques, [Hepatic tolerance of atypical antipsychotic drugs]," L'Encéphale, 2002, 28(1):542-551, 10 pgs.

Dvir-Ginzberg, M., et al., "Liver Tissue Engineering Within alginate Scaffolds: Effects of Cell-Seeding Density on Hepatocyte Viability, Morphology, and Function," Tissue Eng, 2003, 9(4):757-766, 10 pgs.

Edling, Y., et al., "Increased sensitivity for troglitazone-induced cytotoxicity using a human in vitro co-culture model," Toxicol In vitro, 2009, 23:1387-1395, 9 pgs.

Ekser, B., et al., "Comparable outcomes in intestinal retransplantation: Single-center cohort study," The Journal of Clinical and Translational Research, 2018, 32(7):e13290, 10 pgs.

El Kasmi, K.C., et al., "Phytosterols Promote Liver Injury and Kupffer Cell Activation in Parenteral Nutrition-Associated Liver Disease," Sci Transl Med, 2013, 5(206):206ra137, 10 pgs.

El Taghdouini, A., et al., "In vitro reversion of activated primary human hepatic stellate cells," Fibrogenesis & Tissue Repair, 2015, 8:14, 15 pgs.

The Encode Project Consortium, "An integrated encyclopedia of DNA elements in the human genome," Nature, 2012, 489:57-74, 18 pgs.

Engmann, J., et al., "Fluid mechanics of eating, swallowing and digestion—overview and perspectives," Food & Function, 2013, 4:443-447, 5 pgs.

Fahrmayr, C., et al., "Phase I and II metabolism and MRP2-mediated export of bosentan in MDCKII-OATP1B1-CYP3A-UGT1A1-MRP2 quadruple-transfected cell line," Br J Pharmacol, 2013, 169:21-33, 13 pgs.

(56) References Cited

OTHER PUBLICATIONS

Falasca, L., et al., "The effect of retinoic acid on the re-establishment of differentiated hepatocyte phenotype in primary culture," Cell Tissue Res, 1998, 293:337-347, 11 pgs.
Finkenzeller, K., *RFID Handbook: Fundamentals and Applications in Contactless Smart Cards, Radio Frequency Identification and Near-Field Communication, Third Edition*. John Wiley & Son, Ltd., Chichester, West Sussex, 2010, 8 pgs. (Table of Contents Only).
Fisher, A., et al., "Entacapone-Induced Hepatotoxicity and Hepatic Dysfunction," Mov Disord, 2002, 17:1362-1365, 4 pgs.
Fromenty, B., "Drug-induced liver injury in obesity," J Hepatol, 2013, 58:824-826, 3pgs.
Gafni, O., et al., "Derivation of novel human ground state naïve pluripotent stem cells," Nature, 2013, 504:282-286, 20 pgs.
Geerts, A., et al., "Formation of Normal Desmin Intermediate Filaments in Mouse Hepatic Stellate Cells Requires Vimentin," Hepatology, 2001, 33:177-188 12 pgs.
Gerdes, H-H., et al., "Tunneling nanotubes, an emerging intercellular communication route in development," 2013, 130:381-387, 7 pgs.
Giles, D.A., et al., "Thermoneutral housing exacerbates nonalcoholic fatty liver disease in mice and allows for sex-independent disease modeling," Nature Medicine, 2017, 23(7):829-838, 13 pgs.
Glorioso, J.M., et al., "Pivotal Preclinical Trial of the Spheroid Reservoir Bioartificial Liver," J Hepatol, 2015, 63(2):388-398, 27 pgs.
Gomez-Pinilla, P.J., et al., "Ano1 is a selective marker of interstitial cells of Cajal in the human and mouse gastrointestinal tract," Am J Physiol Gastrointest Liver Physiol, 2009, 296:G1370-G1381, 12 pgs.
Grapin-Botton, A., "Three-dimensional pancreas organogenesis models," Diabetes Obes Metab, 2016, 18(Suppl 1):33-40, 8 pgs.
Gregersen, H., et al., "The Zero-Stress State of the Gastrointestinal Tract: Biomechanical and Functional Implications," Digestive Diseases and Sciences, 2000, 45(12):2271-2281, 11 pgs.
Guo, G., et al., "Epigenetic resetting of human pluripotency," Development, 2017, 144:2748-2763, 17 pgs.
Gurdon, J.B., "Adult Frogs Derived from the Nuclei of Single Somatic Cells," Dev Biol, 1962, 4:256-273, 18 pgs.
Gurken, A., "Advances in small bowel transplantation," Turk J Surg., 2017, 33(3):135-141, 7 pgs.
Haimovich, G., et al., "Intercellular mRNA trafficking via membrane nanotube-like extensions in mammalian cells," 2017, PNAS, pp. E9873-E9882, 10 pgs.
Han, B., et al., "Microbiological safety of a novel bio-artificial liver support system based on porcine hepatocytes: a experimental study," European Journal of Medical Research, 2012, 17:13, 8 pgs.
Hassan, W., et al., "Reduced Oxidative Stress Contributes to the Lipid Lowering Effect of Isoquercitrin in Free Fatty Acids Induced Hepatocytes," Oxid Med Cell Longev, 2014, 313602, 18 pgs.
Heidari, R., et al., "Factors affecting drug-induced liver injury: antithyroid drugs as instances," Clin Mol Hepatol, 2014, 20:237-248, 12 pgs.
Hernandez, F., et al., "Refining Indications for Intestinal Retransplantation," International Small Bowel Symposium 2013; Abstract 12.241 (online: https://www.tts.org/component/%20tts/?view=presentation&id=13241) Accessed Jun. 12, 2017, 3 pgs.
Hooton, D., et al., "The Secretion and Action of Brush Border Enzymes in the Mammalian Small Intestine," Rev Physiol Biochem Pharmacol, 2015, 168:59-118, 60 pgs.
Hou, P., et al., "Pluripotent Stem Cells Induced from Mouse Somatic Cells by Small-Molecule Compounds," Science, 2013, 341:651-654, 4 pgs.
Hsu, F., et al., "The UCSC Known Gene," Bioinformatics, 2006, 22(9):1036-1046, 11 pgs.
Hu, H., et al., "Long-Term Expansion of Functional Mouse and Human Hepatocytes as 3D Organoids," Cell, 2018, 175:1591-1606, 36 pgs.
Hu, X., et al., "Micrometer-Scale Magnetic-Resonance-Coupled Radio-Frequency Identification and Transceivers for Wireless Sensors in Cells," Physical Review Applied, 2017, 8:014031, 13 pgs.
Huch, M., et al., "Long-Term Culture of Genome-Stable Bipotent Stem Cells from Adult Human Liver," Cell, 2015, 160:299-312, 14 pgs.
Hynds, R.E., et al., "The relevance of human stem cell-derived organoid models for epithelial translational medicine," Stem Cells, 2013, 31(3):417-422, 11 pgs.
Ijpenberg, A., et al., "Wt1 and retinoic acid signaling are essential for stellate cell development and liver morphogenesis," Dev Biol, 2007, 312:157-170, 14 pgs.
Inoue, H., et al., "iPS cells: a game changer for future medicine," EMBO J, 2014, 33(5):409-417, 9 pgs.
Ito, K., et al., "Temporal Transition of Mechanical Characteristics of HUVEC/MSC Spheroids Using a Microfluidic Chip with Force Sensor Probes," Micromachines, 2016, 7:221, 14 pgs.
Jalan-Sakrikar, N., et al., "Hedgehog Signaling Overomes an EZH2-Dependent Epigenetic Barrier to Promote Cholangiocyte Expansion," PLoS One, 2016, 11(12):e0168266, 19 pgs.
Kanuri, G., et al., "In Vitro an in Vivo Models of Non-Alcoholic Fatty Liver Disease (NAFLD)," Int J Mol Sci, 2013, 14:11963-11980, 18 pgs.
Karlikow, M., et al., "*Drosophila* cells use nanotube-like structures to transfer dsRNA and RNAi machinery between cells," Scientific Reports, 2016, 6:27085, 9 pgs.
Keitel, V., et al., "De Novo Bile Salt Transporter Antibodies as a Possible Cause of Recurrent Graft Failure After Liver Transplantation: A Novel Mechanism of Cholestasis," Hepatology, 2009, 50:510-517, 8 pgs.
Kelly, G.M., et al., "Retinoic Acid and the Development of the Endoderm," J Dev Biol, 2015, 3:25-56, 32 pgs.
Khan, F.A., et al., "Overview of intestinal and multivisceral transplantation," UpToDate, Sep. 2018 [online: https://www.uptodate.com/contents/overview-of-intestinal-and-multivisceral-transplantation/print], 32 pgs.
Kilens, S., et al., "Parallel derivation of isogenic human primed and naïve induced pluripotent stem cells," Nat Commun, 2018, 9:360, 13 pgs.
Kilpinen, H., et al., "Common genetic variation drives molecular heterogeneity in human iPSCs," Nature, 2017, 546(7658):370-375, 51 pgs.
Kim, D., et al., "HISAT: a fast spliced aligner with low memory requirements," Nature Methods, 2015, 12(4):357-360, 6 pgs.
Kock, K., et al., "A Perspective on Efflux Transport Proteins in the Liver," Clin Pharmacol Ther, 2012, 92(5):599-612, 29 pgs.
Koehler, E.M., et al., "Presence of Diabetes Mellitus and Steatosis Is Associated With Liver Stiffness in a General Population: The Rotterdam Study," Hepatology, 2016, 63:138-147, 10 pgs.
Kolodny, G.M., "Evidence for Transfer of Macromolecular RNA Between Mammalian Cells in Culture," Exp Cell Res, 1971, 65:313-324, 12 pgs.
Kordes, C., et al., "Hepatic stellate cells contribute to progenitor cells and liver regeneration," J Clin Invest, 2014, 124(12):5503-5515, 13 pgs.
Krähenbühl, S., et al., "Toxicity of Bile Acids on the Electron Transport Chain of Isolated Rat Liver Mitochondria," Hepatology, 1994, 169:471-479, 9 pgs.
Kubal, C.A., et al., "Challenges with Intestine and Multiviseral Re-Transplantation: Importance of Timing of Re-Transplantation and Optimal Immunosuppression, " Ann Transplant, 2018, 23:98-104, 7 pgs.
Kullak-Ublick, G.A., et al., "Drug induced liver injury: recent advantages in diagnosis and risk assessment," Gut, 2017, 66:1154-1164, 11 pgs.
Kumar, J.A., et al., "Controversies in the Mechanism of Total Parenteral Nutrition Induced Pathology," Children, 2015, 2:358-370, 13 pgs.
Kurpios, N.A., et al., "The direction of gut looping is estalished by changes in the extracellular matrix and in cell:cell adhesion," PNAS, 2008, 105(25):8499-8506, 8 pgs.
Lê, S., et al., "FactoMineR: An R Package for Multivariate Analysis," Journal of Statistical Software, 2008, 25(1):1-18, 18 pgs.

(56) References Cited

OTHER PUBLICATIONS

Le Vee, M., et al., "Polarized expression of drug transporters in differentiated human HepaRG cells," Toxicol In Vitro, 2013, 27:1979-1986, 8 pgs.

Lechner, C., et al., "Development of a fluorescence-based assay for drug interactions with human Multidrug Resistance Related Protein (MRP2; ABCC2) in MDCKII-MRP2 membrane vesicles," Eur J Pharm Biopharm, 2010, 75:284-290, 7 pgs.

Lee, W.M., et al., "Intravenous N-Acetylcysteine Improves Transplant-Free Survival In Early Stage Non-Acetaminophen Acute Liver Failure," Gastroenterology, 2009, 137(3):856-864, 18 pgs.

Leslie, E.M., et al., "Differential Inhibition of Rat and Human $Na^+$-Dependent Taurocholate Cotransporting Polypeptide (NTCP/SLC10A1) by Bosentan: A Mechanism for Species Differences in Hepatotoxicity," J Pharmacol Exp Ther, 2007, 321(3):1170-1178, 9 pgs.

Leung, A.A., et al., "Tolerance testing of passive radio frequency identification tags for solvent, temperature, and pressure conditions encountered in an anatomic pathology or biorepository setting," J Pathol Inform, 2010, 1:21, 6 pgs.

Li, N., et al., "A Systematic Assessment of Mitochondrial Function Identified Novel Signatures for Drug-Induced Mitochondrial Disruption in Cells," Toxicol Sci, 2014, 142(1):261-273, 13 pgs.

Lin, Y., et al., "Differentiation, Evaluation, and Application of Human Induced Pluripotent Stem Cell-Derived Endothelial Cells," Arterioscler Thromb Vasc Biol, 2017, 37:2014-2025, 12 pgs.

Liu, L., et al., "A Review of Locomotion Systems for Capsule Endoscopy," IEEE Rev Biomed Eng, 2015, 8:138-151, 14 pgs.

Loike, J.D., et al., "Opinion: Develop Organoids, Not Chimeras, for Transplantation," The Scientist Magazine, Aug. 2019, (online: https://www.the-scientist.com/news-opinion/opinion--develop-organoids--not-chimeras--for-transplantation-66339), 3 pgs.

Love, M.I., et al., "Moderated estimation of fold change and dispersion for RNA-seq data with DESeq2," Genome Biol, 2014, 15:550, 21 pgs.

Low, L.A., et al., "Organs-on-chips: Progress, challenges, and future directions," Experimental Biology and Medicine, 2017, 242:1573-1578, 6 pgs.

Luntz, J., et al., "Mechanical Extension Implants for Short-Bowel Syndrome," Smart Structures and Materials 2006: Smart Structures and Integrated Systems, Proc of SPIE, 2006, 6173:617309-1-617309-11, 11 pgs.

MacParland, S.A., et al., "Single cell RNA sequencing of human liver reveals distinct intrahepatic macrophage populations," Nat Commun, 2018, 9:4383, 21 pgs.

Mahe, M.M., et al., "In Vivo Model of Small Intestine," Methods Mol Biol, 2017, 1597:229-245, 17 pgs.

Makin, A.J., et al., "A 7-Year Experience of Severe Acetaminophen-Induced Hepatotoxicity (1987-1993)," Gastroenterology, 1995, 109:1907-1916, 10 pgs.

Malinen, M.M., et al., "Differentiation of liver progenitor cell line to functional organotypic cultures in 3D nanofibrillar cellulose and hyaluronan-gelatin hydrogels," Biomaterials, 2014, 35:5110-5121, 12 pgs.

Mammoto, A., et al., "Mechanosensitive mechanisms in transcriptional regulation," Journal of Cell Science, 2012, 125:3061-3073, 13 pgs.

Marcum, Z.A., et al., "Medication Adherence to Multi-Drug Regimens," Clin Geriatr Med, 2012, 28(2):287-300, 15 pgs.

Marini, F., et al., "pcaExplorer: an R/Bioconductor package for interacting with RNA-seq principal components," BMC Bioinformatics, 2019, 20:331, 8 pgs.

Marini, F., "pcaExplorer: Interactive Visualization of RNA-seq Data Using a Principal Components Approach," bioconductor.org, R package version 2.3.0, 2017, 7 pgs.

Markova, S.M., et al., "Association of *CYP2C9*2* With Bosentan-Induced Liver Injury," Clin Pharmacol Ther., Dec. 2013, 94(6):678-86, 9 pgs.

Marsh, M.N., et al., "A study of the small intestinal mucosa using the scanning electron microscope," Gut, 1969, 10:940-949, 10 pgs.

McCracken, K.W., et al., "Erratum: Wnt/β-catenin promotes gastric fundus specification in mice and humans," Nature, 2017, 543:136, 1 pg.

McKenzie, T.J., et al., "Artificial and Bioartificial Liver Support," Seminars in Liver Disease, 2008, 28(2):210-217, 8 pgs.

Mercaldi, C.J., et al., "Methods to Identify and Compare Parenteral Nutrition Administered From Hospital-Compounded and Premixed Mulitchamber Bags in a Retrospective Hospital Claims Database," J Parenter Enteral Nutr, 2012, 36(3):330-336, 7 pgs.

Michaut, A., et al., "A cellular model to study drug-induced liver injury in nonalcoholic fatty liver disease: application to acetaminophen," Toxicol Appl Pharmacol, 2016, 292:40-55, 35 pgs.

Miki, T., et al., "Hepatic Differentiation of Human Embryonic Stem Cells Is Promoted by Three-Dimensional Dynamic Perfusion Culture Conditions," Tissue Eng: Part C Methods, 2011, 17(5):557-568, 12 pgs.

Mörk, L.M., et a., "Comparison of Culture Media for Bile Acid Transport Studies in Primary Human Hepatocytes," J Clin Exp Hepatol, 2012, 2:315-322, 8 pgs.

Nakamura, T., et al., "Advancing Intestinal Organoid Technology Toward Regenerative Medicine," Cell Mol Gastroenterol Hepatol, 2018, 5:51-60, 10 pgs.

Navarro, V.J., et al., "Drug-Related Hepatotoxicity," N Engl J Med, 2006, 354:731-739, 9 pgs.

Negishi, T., et al., "Retinoic Acid Signaling Positiviely Regulates Liver Specification by Inducing *wnt2bb* Gene Expression in Medaka," Hepatology, 2010, 51:1037-1045, 9 pgs.

Nelson, B.J., et al., "Microrobots for Minimally Invasive Medicine," Annual Review of Biomedical Engineering, 2010, 12(12):55-85, 33 pgs.

Nelson, C.M., "On Buckling Morphogenesis," J Biomech Eng, 2016, 138:021005-1-021005-6, 6 pgs.

Ni, X., et al., "Functional human induced hepatocytes (hiHeps) with bile acid synthesis and transport capacities: A novel in vitro cholestatic model," Sci Rep, 2016, 6:38694, 16 pgs.

Nishida, T., et al., "Rat liver canalicular membrane vesicles contain ATP-dependent bile acid transport system," Proc Natl Acad Sci USA, 1991, 88:6590-6594, 5 pgs.

Oorts, M., et al., "Drug-induced cholestasis risk assessment in sandwich-cultured human hepatocytes," Toxicol In Vitro, 2016, 34:179-186, 8 pgs.

Orso, G., et al., "Pediatric parenteral nutrition-associated liver disease and cholestasis: Novel advances in pathomechanisms-based prevention and treatment," Dig Liver Dis, 2016, 48:215-222, 8 pgs.

Ouchi, R., et al., "Modeling Steatohepatitis in Humans with Pluripotent Stem Cell-Derived Organoids," Cell Metabolism, Aug. 2019, 30:1-11, 17 pgs.

Pardal, M.L., et al., "Towards the Internet of Things: An Introduction to RFID technology," RFID Technology—Concepts, Applications, Challenges, Proceedings of the 4th International Workshop, IWRT 2010, In conjunction with ICEIS 2010, Funchal, Madeira, Portugal, Jun. 2010, pp. 69-78, 10 pgs.

Pastor, W.A., et al., "TFAP2C regulates transcription in human naïve pluripotency by opening enhancers," Nature Cell Biology, 2018, 20:553-564, 18 pgs.

Pereira, C.F., et al., "Heterokaryon-Based Reprogramming of Human B Lymphocytes for Pluripotency Requires Oct4 but Not Sox2," PLoS Genet, 2008, 4(9):e1000170, 14 pgs.

Pessayre, D., et al., "Central role of mitochondria in drug-induced liver injury," Drug Metab Rev, 2012, 44(1):34-87, 54 pgs.

Pessayre, D., et al., "Mitochondrial involvement in drug-induced liver injury," in *Adverse Drug Reaction*, J. Uetrecht (ed.), Handb Exp Pharmacol 196, Springer-Verlag, Berlin, Germany, 2010, pp. 311-365, 55 pgs.

Poling, H.M., et al., "Mechanically induced development and maturation of human intestinal organoids in vivo," Nat Biomed Eng, 2018, 2(6):429-442, 31 pgs.

Polson, J., et al., "AASLD Position Paper: The Management of Acute Liver Failure," Hepatology, 2005, 41(5):1179-1197, 19 pgs.

Purton, L.E., et al., "All-trans retinoic acid enhances the long-term repopulating activity of cultured hematopoietic stem cells," Blood, 2000, 95:470-477, 8 pgs.

(56) References Cited

OTHER PUBLICATIONS

Rachek, L.I., et al., "Troglitazone, but not rosiglitazone, damages mitochondrial DNA and induces mitochondrial dysfunction and cell death in human hepatocytes," Toxicol Appl Pharmacol, 2009, 240(3):348-354, 17 pgs.
Ramirez-Weber, F-A., et al., "Cytonemes: Cellular Processes that Project to the Principal Signaling Center in *Drosophila* Imaginal Discs," Cell, 1999, 97:599-607, 9 pgs.
Rane, A., et al., "Drug Metabolism in the Human Fetus and Newborn Infant," Pediatr Clin North Am, 1972, 19(1):37-49, 11 pgs.
Rao, R.R., et al., "Gene Expression Profiling of Embryonic Stem Cells Leads to Greater Understanding of Pluripotency and Early Development Events," Biol Reprod, 2004, 71:1772-1778, 7 pgs.
Rector, R.S., et al., "Mitochondrial dysfunction prededes insulin resistance and hepatic steatosis and contributes to the natural history of non-alcoholic fatty liver disease in an obese rodent model," J Hepatol, 2010, 52(5):727-736, 20 pgs.
Reuben, A., et al. "Drug-Induced Acute Liver Failure: Results of U.S. Multicenter, Prospective Study," Hepatology, 2010, 52:2065-2076, 12 pgs.
Riedinger, H-J, et al., "Reversible shutdown of replicon inititaion by transient hypoxia in Ehrlich ascites cells: Dependence of initiation on short-lived protein," Eur J. Biochem, 1992, 210:389-398, 10 pgs.
Roberts, A., et al., "Identification of novel transcripts in annotated genomes using RNA-Seq," Bioinformatics, 2011, 27(17):2325-2329, 5 pgs.
Roberts, A., et al., "Improving RNA-Seq expression estimated by correcting for fragment bias," Genome Biol, 2011, 12:R22, 14 pgs.
Ronn, R.E., et al., "Retinoic Acid Regulates Hematopoietic Development from Human Pluripotent Stem Cells," Stem Cell Reports, 2015, 4:269-281, 13 pgs.
Rouch, J.D., et al., "Scalability of an endoluminal spring for distraction enterogenesis," Journal of Pediatric Surgery, 2016, 51:1988-1992, 5 pgs.
Roy, S., et al., "Cytoneme-Mediated Contact-Dependent Transport of the *Drosophila* Decapentaplegic Signaling Protein," Science, 2014, 343:1244624-1, 11 pgs.
Russo, M.W., et al., "Liver Transplantation for Acute Live Failure From Drug Induced Liver Injury in the United States," Liver Transpl, 2004, 10:1018-1023 6 pgs.
Sachs, N., et al., "A Living Biobank of Breast Cancer Organoids Captures Disease Heterogeneity," Cell, 2018, 172:373-386, 25 pgs.
Saini, A., "Cystic Fibrosis Patients Benefit from Mini Guts," Cell Stem Cell, 2016, 19:425-427, 3 pgs.
Salas-Vidal, E., et al., "Imaging filopodia dynamics in the mouse blastocyst," Developmental Biology, 2004, 265:75-89, 15 pgs.
Sartori-Rupp, A., et al., "Correlative cryo-electron microscopy reveals the structure of TNTs in neuronal cells," Nature Communications, 2019, 10:342, 16 pgs.
Sasai, Y., "Cytosystems dynamics in self-organization of tissue architecture," Nature, 2013, 493:318-326, 9 pgs.
Sato, T., et al., "Snapshot: Growing Organoids from Stem Cells," Cell, 2015, 161:1700-1700e1, 2 pgs.
Serviddio, G., et al., "Ursodeoxycholic Acid Protects Against Secondary Biliary Cirrhosis in Rats by Preventing Mitochondrial Oxidative Stress," Hepatology, 2004, 39:711-720, 10 pgs.
Shahbazi, M.N., et al., "Self-organization of human embryo in the absence of maternal tissues," Nature Cell Biology, 2016, 18(6):700-708, 20 pgs.
Shekherdimian, S., et al., "The feasibility of using an endoluminal device for intestinal lengthening," Journal of Pediatric Surgery, 2010, 45:1575-1580, 6 pgs.
Shi, X-L., et al., "Effects of Membrane Molecular Weight Cutoff on Performance of a Novel Bioartificial Liver," Artificial Organs, 2011, 35(3):E40-E46, 7 pgs.
Shi, X-L., et al., "Evaluation of a novel hybrid bioartificial liver based on a multi-layer flat-plate bioreactor," World J Gastroenterol, 2012, 18(28):3752-3760, 9 pgs.

Shyer, A.E., et al., "Villification: How the Gut Gets its Villi," Science, 2013, 342:212-218, 7 pgs.
Sim, Y-J., et al., "2i Maintains a Naïve Ground State in ESCs through Two Distinct Epigenetic Mechanisms," Stem Cell Reports, 2017, 8:1312-1328, 17 pgs.
Sitti, M., et al., "Biomedical Applications of Untethered Mobile Milli/Microrobots," Proc IEEE Inst Electr Electron Eng, 2015, 103(2):205-224, 20 pgs.
Slaymaker, I.M., et al., "Rationally engineered Cas9 nuclease with improved specificity," Science, 2016, 351(6268):84-88, 10 pgs.
Sloan, C.A., et al., "ENCODE data at the ENCODE portal," Nucleic Acids Res, 2016, 44:D726-D732, 7 pgs.
Sneddon, I.N., "The Relation Between Load and Penetration in the Axisymmetric Boussinesq Problem for a Punch of Arbitrary Profile," Int. J. Engng. Sci., 1965, 3:47-57, 11 pgs.
Soffers, J.H.M., et al., "The growth pattern of the human intestine and its mesentery," BMC Dev Biol, 2015, 15:31, 16 pgs.
Song, W., et al., "Engraftment of human induced pluripotent stem cell-derived hepatocytes in immunocompetent mice via 3D co-aggregation and encapsulation," Sci Rep, 2015, 5:16884, 13 pgs.
Song, Z., et al., "Efficient generation of hepatocyte-like cells from human induced pluripotent stem cells," Cell Res, 2009, 19:1233-1242, 10 pgs.
Spence, J.R., et al., "Vertebrate Intestinal Endoderm Development," Developmental Dynamics, 2011, 240:501-520, 20 pgs.
Stafford, D., et al., "A conserved role for retinoid signaling in vertebrate pancreas development," Dev Genes Evol, 2004, 214:432-441, 10 pgs.
Stender, S., et al., "Adiposity Amplifies the Genetic Risk of Fatty Liver Disease Conferred by Multiple Loci," Nat Genet, 2017, 49(6):842-847, 18 pgs.
Stevens, J.L., et al., "The future of drugs safety testing: expanding the view and narrowing the focus," Drug Discov Today, 2009, 14(3/4):162-167, 6 pgs.
Stuart, T., et al., "Comprehensive Integration of Single-Cell Data," Cell, 2019, 177:1888-1902, 37 pgs.
Sugimoto, S., et al., "Reconstruction of the Human Colon Epithelium In Vivo," Cell Stem Cell, 2018, 22:171-176, 16 pgs.
Suzuki, A., et al., "Clonal identification and characterization of self-renewing pluripotent stem cells in the developing liver" The Journal of Cell Biology, 2002, 156(1):173-184, 12 pgs.
Tada, M., et al., "Embryonic germ cells induce epigenetic reprogramming of somatic nucleus in hybrid cells," EMBO J, 1997, 16(21):6510-6520, 11 pgs.
Takahashi, S., et al., "Epigenetic differences between naïve and primed pluripotent stem cells," Cellular and Molecular Life Sciences, 2018, 75:1191-1203, 13 pgs.
Takashima, Y., et al., "Resetting Transcription Factor Control Circuitry toward Ground-State Pluripotency in Human," Cell, 2014, 158(6):1254-1269, 32 pgs.
Takebe, T., et al., "Human iPSC-Derived Miniature Organs: A Tool for Drug Studies," Clin Pharmacol Ther, 2014, 96(3):310-313, 4 pgs.
Takebe, T., et al., "Massive and Reproducible Production of Liver Buds Entirely from Human Pluripotent Stem Cells," Cell Reports, 2017, 21:2661-2670, 11 pgs.
Takebe, T., et al., "Vascularized and Complex Organ Buds from Diverse Tissues via Mesenchymal Cell-Driven Condensation," Cell Stem Cell, 2015, 16:556-565, 10 pgs.
Takebe, T., et al., "Vascularized and functional human liver from an iPSC-derived organ bud transplant," Nature, 2013, 499:481-484, 5 pgs.
Tamm, C., et al., "A Comparative Study of Protocols for Mouse Embryonic Stem Cell Culturing," PLoS ONE, 2013, 8(12):e81156, 10 pgs.
Tamminen, K., et al., "Intestinal Commitment and Maturation of Human Pluripotent Stem Cells Is Independent of Exogenous FGF4 and R-spondin1," PLOS One, Jul. 2015, 10(7):e0134551, 19 pgs.
Terry, B.S., et al., "Preliminary Mechanical Characterization of the Small Bowel for In Vivo Robotic Mobility," J. Biomech Eng, 2011, 133:091010-1-09101-7, 7 pgs.
The WNT homepage, "Small molecules in Wnt signalling," Nusse Lab, Jan. 2019, 2 pgs.

(56) References Cited

OTHER PUBLICATIONS

Theunissen, T.W., et al., "Systematic Identification of Culture Conditions for Induction and Maintenance of Naïve Human Pluripotency," Cell Stem Cell, 2014, 15:471-487, 47 pgs.
Tian, X., et al., "Modulation of Multidrug Resistance-Associated Protein 2 (Mrp2) and Mrp3 Expression and Function with Small Interfering RNA in Sandwich-Cultured Rat Hepatocytes," Mol Pharmacol, 2004, 66(4):1004-1010, 7 pgs.
Tran, K., et al. "Evaluation of regional and whole gut motility using the wireless motility capsule: relevance in clinical practice," Therap Adv Gasroenterol, 2012, 5(4):249-260, 12 pgs.
Trapnell, C., et al., "Transcript assembly and quantification by RNA-Seq reveals unannotated transcripts and isoform switching during cell differentiation," Nat Biotechnol, 2010, 28(5):511-515, 8 pgs.
Troy, D.B. (ed.), Remington: The Science and Practice of Pharmacy, 21$^{st}$ Ed., 2006, Lippincott, Williams & Wilkens, Baltimore, MD, 6 pgs., Table of Contents Only.
Tsedensodnom, O., et al., "ROS: Redux and Paradox in Fatty Liver Disease," Hepatology, 2013, 58(4):1210-1212, 3 pgs.
Tsukada, N., et al., "The Structure and Organization of the Bile Canalicular Cytoskeleton With Special Reference to Actin and Actin-Binding Proteins," Hepatology, 1995, 21(4):1106-1113, 8 pgs.
Tyml, K., et al., "Lipopolysaccharide reduces intercellular coupling in vitro and arteriolar conducted response in vivo," AJP-Heart Circ Physiol, 2001, 281:H1397-H1406, 10 pgs.
The United States Pharmacopeia: The National Formulary (USP 24 NF 19), United States Pharmacopeial Convention, Inc., Rockville, MD, 1999, 4 pgs., Table of Contents Only.
Valadi, H., et al., "Exosome-mediated transfer of mRNAs and microRNAs in a novel mechanism of genetic exchange between cells," Nat Cell Biol, 2007, 9(6):654-659, 17 pgs.
Van De Garde, M.D., et al., "Liver Monocytes and Kupffer Cells Remain Transcriptionally Distinct during Chronic Viral Infection," PLoS One, 2016, 11(11):e0166094, 16 pgs.
Venick, R.S., et al., "Unique Technical and Patient Characteristics of Retransplantation: A Detailed Single Center Analysis of Intestinal Transplantation," International Small Bowel Symposium 2013; Abstract 5.203 (online: https://www.tts.org/component/%20tts/?view=presentation&id=13190), Accessed Jun. 12, 2017, 4 pgs.
Verma, S., et al., "Diagnosis, management and prevention of drug-induced liver injury," Gut, 2009, 58:1555-1564, 10 pgs.
Vosough, M., et al., "Generation of Functional Hepatocyte-Like Cells from Human Pluripotent Stem Cells in a Scalable Suspension Culture," Stem Cells Dev, 2013, 22(20):2693-2705, 13 pgs.
Wakayama, T., et al., "Full-term development of mice from enucleated oocytes injected with cumulus cell nuclei," Nature, 1998, 394:369-374, 6 pgs.
Wang, S., (Ed.), "The role of homologous genes in the development of appendages," in Basis of Developmental Biology, Press of East China University of Science and Technology, 2014, pp. 184-185, 4 pgs.
Wang, Y., et al., "Hepatic stellate cells, liver innate immunity, and hepatitis C virus," J Gastroenterol Hepatol, 2013, 28(Suppl 1):112-115, 8 pgs.
Want, R., "An Introduction to RFID Technology," IEEE Pervas Comput, 2006, 5:25-33, 9 pgs.
Ware, C.B., "Concise Review: Lessons from Naïve Human Pluripotent Cells," Stem Cells, 2017, 35:35-41, 7 pgs.
Warren, C.R., et al., "Induced Pluripotent Stem Cell Differentiation Enables Functional Validation of GWAS Variants in Metabolic Disease," Cell Stem Cell, 2017, 20:547-557, 18 pgs.
Warren, C.R., et al., "The NextGen Genetic Association Studies Consortium: A Foray into In Vitro Population Genetics," Cell Stem Cell, 2017, 20:431-433, 3 pgs.
Wernig, M., et al., "In vitro reprogramming of fibroblasts into a pluripotent ES-cell-like state," Nature, 2007, 448:318-324, 8 pgs.
Wieck, M.M., et al., "Prolonged Absence of Mechanoluminal Stimulation in Human Intestine Alters the Transcriptome and Intestinal Stem Cell Niche," Cell Mol Gastroenterol Hepatol, 2017, 3(3):367-388e1, 23 pgs.
Wiley, L.A., et al., "cGMP production of patient-specific iPSCs and photoreceptors precursor cells to treat retinal degenerative blindness," Scientific Reports, 2016, 6:30742, 16 pgs.
Wilmut, I., et al., "Viable offspring derived from fetal and adult mammalian cells," Nature, 1997, 385:810-813, 4 pgs.
Xu, R., et al., "Association Between Patatin-Like Phospholipase Domain Containing 3 Gene (PNPLA3) Polymorphisms and Non-alcoholic Fatty Liver Disease: A HuGE Review and Meta-Analysis," Sci Rep, 2015, 5:9284, 11 pgs.
Xu, R., et al. (Eds.), "Retinoic acid receptor" in Basis and Clinic of Receptor, Shanghai Science and Technology Press, 1992, pp. 129-131, 2 pgs.
Yanagimachi, M.D., et al., "Robust and Highly-Efficient Differentiation of Functional Monocytic Cells from Human Pluripotent Stem Cells under Serum- and Feder Cell-Free Conditions," PLoS One, 2013, 8(4):e59243, 9 pgs.
Yang, K., et al., "Systems Pharmacology Modeling Predicts Delayed Presentation and Species Differences in Bile Acid-Mediated Troglitazone Hepatotoxicity," Clin Pharmacol Ther, 2014, 96(5):589-598, 21 pgs.
Yoneda, M., et al., "Noninvasive assessment of liver fibrosis by measurement of stiffness in patients with nonalcoholic fatty liver disease (NAFLD)," Dig Liver Dis, 2008, 40:371-378, 8 pgs.
Yu, H., et al., "The Contributions of Human Mini-Intestines to the Study of Intestinal Physiology and Pathophysiology," Annu Rev Physiol, 2017, 79:291-312, 22 pgs.
Zain, S.M., et al., "A common variant in the glucokinase regulatory gene rs780094 and risk of nonalcoholic fatty liver disease: A meta-analysis," J Gastroenterol Hepatol, 2015, 30:21-27, 7 pgs.
Zambrano, E., et al., "Total parenteral Nutrition Induced Liver Pathology: An Autopsy Series of 24 Newborn Cases," Pediatr Dev Pathol, 2004, 7:425-432, 8 pgs.
Zborowski, J., et al., "Induction of swelling of liver mitochondria by fatty acids of various chain length," Biochim Biophys Acta, 1963, 70:596-598, 3 pgs.
Zhang, R-R., et al., "Human iPSC-Derived Posterior Gut Progenitors Are Expandable and Capable of Forming Gut and Liver Organoids," Stem Cell Reports, 2018, 10(3):780-793, 14 pgs.
Zhao, Y., et al., "A XEN-like State Bridges Somatic Cells to Pluripotency during Chemical Reprogramming," Cell, 2015, 163:1678-1691, 15 pgs.
Zhong, J., et al., "Continuous-wave laser-assisted injection of single magnetic nanobeads into living cells," Sensors and Actuators B: Chemical, 2016, 230:298-305, 8 pgs.
Chinese Office Action, the Second Office Action and Supplementary Search Report, dated Dec. 19, 2019 for Application No. CN 201580034910.4, 11 pgs.
European Search Report and Written Opinion dated Oct. 31, 2019 for Application No. EP 17793451.0, 11 pgs.
International Search Report and Written Opinion dated Jul. 9, 2018 for Application No. PCT/US2018/027585, 12 pgs.
International Search Report and Written Opinion dated May 7, 2019 for Application No. PCT/US2018/067057, 15 pgs.
International Search Report and Written Opinion dated Oct. 29, 2019 for Application No. PCT/US2019/041985, 13 pgs.
International Search Report and Written Opinion dated Dec. 5, 2019 for Application No. PCT/US2019/050846, 10 pgs.
International Search Report and Written Opinion dated Dec. 13, 2019 for Application No. PCT/US2019/053408, 10 pgs.
U.S. Appl. No. 16/346,190, filed Apr. 30, 2019, by Takebe et al., entitled: "Liver Organoid Disease Models and Methods of Making and Using Same."
U.S. Appl. No. 16/599,620, filed Oct. 11, 2019, by Wells et al., entitled: "Methods and Systems for Converting Precursor Cells Into Intestinal Tissues Through Directed Differentiation."
U.S. Appl. No. 16/603,611, filed Oct. 8, 2019, by Mahe et al., entitled: "Methods of Making Improved Human Intestinal Organoid Compositions via Application of Strain and Human Intestinal Organoid Compositions Thereof."

(56) References Cited

OTHER PUBLICATIONS

U.S. Appl. No. 16/611,998, filed Nov. 8, 2019, by Takebe et al., entitled: "Liver Organoid Compositions and Methods of Making and Using Same."
Ader. M., et al., "Modeling human development in 3D culture," Current Opinion in Cell Biology, 2014, 31:23-28, 6 pgs.
Adorini, L., et al., "Farnesoid X receptor targeting to treat nonalcoholic steatohepatitis," Drug Discovery Today, Sep. 2012, 17(17/18):988-997, 10 pgs.
Agopian, V.G., et al., "Intestinal Stem Cell Organoid Transplantation Generates Neomucosa in Dogs," Journal of Gastrointestinal Surgery, Jan. 23, 2009, 13(5):971-982, XP055241418, 12 pgs.
Alessi, D.R., et al., "LKB1-Dependent Signaling Pathways," Annu Rev. Biochem., 2006, 75:137-63, 30 pgs.
Altman, G.H., et al., "Cell differentiation by mechanical stress," The FASEB Journal, 2001, 16(2):270-272, 13 pgs.
Ameri, J., et al., "FGF2 Specifies hESC-Derived Definitive Endoderm into Foregut/Midgut Cell Lineages in a Concentration-Dependent Manner," Stem Cells, ePUB Nov. 3, 2009, 28(1):45-56, 12 pgs.
Amieva, M.R., et al. *Helicobacter pylori* enter and survive within multivesicular vacuoles of epithelial cells," Cell. Microbiol., 2002, 4(10):677-690, 15 pgs.
Anderson, G., et al., "Loss of enteric dopaminergic neurons and associated changes in colon motility in an MPTP mouse model of Parkinson's disease," Exp Neurol, Sep. 2007, 207:4-12, 16 pgs.
Andrews, P.W., et al., "Embryonic stem (ES) cells and embryonal carcinoma (EC) cells: opposite sides of the same coin," Biochem Soc Trans, 2005, 33(part 6):1526-1530, 5 pgs.
Ang, S-L, et al., "The formation and maintenance of the definitive endoderm lineage in the mouse: involvement of HNF3/*forkhead* proteins," Development, 1993, 119:1301-1315, 15 pgs.
Anlauf, M., et al., "Chemical coding of the human gastrointestinal nervous system: cholinergic, VIPergic, and catecholaminergic phenotypes," The Journal of Comparative Neurology, 2003, 459:90-111, 22 pgs.
Arora, N., et al., "A process engineering approach to increase organoid yield," Development, 2017, 144:1128-1136, 9 pgs.
Asai, A., et al., "Paracrine signals regulate human liver organoid maturation from induced pluripotent stem cells," Development, 2017, 144:1056-1064, 9 pgs.
Aurora, M., et al., "hPSC-derived lung and intestinal organoids as models of human fetal tissue," Developmental Biology, 2016, 420:230-238, 9 pgs.
Avansino, J.R., et al., "Orthotopic transplantation of intestinal mucosal organoids in rodents," Surgery, Sep. 2006, 140(3):423-434, XP005610494, 12 pgs.
Baetge, G., et al., "Transient catecholaminergic (TC) cells in the vagus nerves and bowel of fetal mice: relationship to the development of enteric neurons," Developmental Biology, 1989, 132:189-211, 23 pgs.
Bajpai, R., et al., "CHD7 cooperates with PBAF to control multipotent neural crest formation," Nature, Feb. 18, 2010, 463:958-962, 7 pgs.
Bansal, D., et al., "An ex-vivo human intestinal model to study *Entamoeba histolytica* Pathogenesis," PLoS Neglected Tropical Diseases, Nov. 2009, 3(11):e551.
Baptista, P.M., et al., "The Use of Whold Organ Decellularization for the Generation of a Vascularized Liver Organoid," Hepatology, 2011, 53(2):604-617, 14 pgs.
Barker, N., et al., "Lgr5$^{+ve}$ Stem Cells Self-Renewal in the Stomach and Build Long-Lived Gastric Units In Vitro," Cell Stem Cell, 2010, 6:25-36, 12 pgs.
Barker, N., et al., "Tissue-Resident Adult Stem Cell Populations of Rapidly Self-Renewing Organs," Cell Stem Cell, Dec. 2010,7:656-670, 15 pgs.
Bartfeld, S., et al., "Stem cell-derived organoids and their application for medical research and patient treatment," J Mol Med, 2017, 95:729-738, 10 pgs.
Bastide, P., et al. "Sox9 regulates cell proliferation and is required for Paneth cell differentiation in the intestinal epithelium," JCB, 2007, 178(4), pp. 635-648, 14 pgs.

Baumann, K., "Colonic organoids for drug testing and colorectal disease modelling," Nature Reviews Molecular Cell Biology, Jul. 2017, 1 pg.
Beck, F., et al., "Expression of *Cdx*-2 in the mouse embryo and placenta: possible tole in patterning of the extra-embroyonic membranes," Dev Dyn, 1995, 204:219-227.
Bergner, A.J., et al., "Birthdating of myenteric neuron subtypes in the small intestine of the mouse," The Journal of Comparative Neurology, 2014, 522:514-527, 14 pgs.
Bitar, K.N., et al., "Intestinal Tissue Engineering: Current Concepts and Future Vision of Regenerative Medicine in the Gut," Neurogastroenterol Motil., Jan. 2012, 24(1):7-19, 20 pgs.
Blaugrund, E., et al., "Distinct subpopulations of enteric neuronal progenitors defined by time of development, sympathoadrenal lineage markers and *Mash-1*-dependence," Development 122, 1996, 309-320, 12 pgs.
Bohorquez, D.V., et al., "An Enteroendocrine Cell—Enteric Glia Connection Revealed by 3D Electron Microscopy," PLOS One, Feb. 2014, 9((2):e89881, 13 pgs.
Brevini, T.A.L., et al., "No shortcuts to pig embryonic stem cells," Theriogenology, 2010, 74:544-550, 7 pgs.
Bruens, L., et al., "Expanding the Tissue Toolbox: Deriving Colon Tissue from Human Pluripotent Stem Cells," Cell Stem Cell, Jul. 2017, 21(1):3-5, 3 pgs.
Brugmann, S.A., et al., "Building additional complexity to in vitro-derived intestinal tissues," Stem Cell Research & Therapy, 2013, 4(Suppl 1):S1, 5 pgs.
Burns, A.J., et al., "Neural stem cell therapies for enteic nervous system disorders," Nature Reviews/Gastroenterology & Hepatology, May 2014, 11:317-328, 12 pgs.
Cabezas, J., et al., "Nonalcoholic Fatty Liver Disease: A Pathological View," Liver Biopsy—Indications, Procedures, Results, Chapter 8, InTech, 2012, pp. 161-188, 29 pgs.
Campbell, F.C., et al., "Transplantation of cultured small bowl enterocytes," Gut, 1993, 34:1153-1155, 4 pgs.
Cao, L., et al., "Development of Intestinal Organoids as Tissue Surrogates: Cell Composition and the Epigenetic Control of Differentiation," Molecular Carcinogenesis, 2015, 54:189-202, 14 pgs.
Chen, C., et al., "*Pdx1* inactivation restricted to the intestinal epithelium in mice alters duodenal gene expression in enterocytes and enteroendocrine cells," Am. J. Physiol. Gastrointest. Liver Pyshiol., 2009, 297:G1126-G1137, 12 pgs.
Chen, T-W., et al., "Ultrasensitive fluorescent proteins for imaging neuronal activity," Nature, Jul. 18, 2013, 499:295-300, 8 pgs.
Cheng, X., et al., "Self-renewing endodermal progenitor lines generated from human pluripotent stem cells," Cell Stem Cell, Apr. 6, 2012, 10:371-384, 14 pgs.
Churin, Y., et al., "*Helicobacter pylori* CagA protein targets the c-Met receptor and enhances the motogenic response," J. Cell Biol., 2003, 161:249-255, 7 pgs.
Cieslar-Pobuda, A., et al., The expression pattern of PFKFB3 enzyme distinguishes between induced-pluripotent stem cells and cancer stem cells, Oncotarget, 6(30):29753-29770, 18 pgs.
Clevers, H., "Modeling Development and Disease with Organoids," Cell, Jun. 2016, 165:1586-1597, 12 pgs.
Coghlan, M.P., et al., "Selective small molecule inhibitors of glycogen synthase kinase-3 modulate glycogen metabolism and gene transcription," Chem. Biol., 2000, 7(10):793-803, 11 pgs.
Correia, C., et al., "Combining Hypoxia and Bioreactor Hydrodynamics Boosts Induced Pluripotent Stem Cell Differentiation Towards Cardiomyocytes," Stem Cell Rev and Rep, 2014, 10:786-801, 16 pgs.
Costa, M., et al., "A method for genetic modification of human embryonic stem cells using electroporation," Nature Protocols, Apr. 5, 2007, 2:792-796, 5 pgs.
Couzin, J., "Small RNAs Make Big Splash," Science, 2002, 298:2296-2297, 2 pgs.
Covacci, A., et al., "Molecular characterization of the 128-kDa immunodominant antigen of *Helicobacter pylori* associated with cytotoxicity and duodenal ulcer," Proc Natl Acad Sci USA, Jun. 1993, 90:5791-5795, 5 pgs.
Curchoe, C.L., et al., "Early acquisition of neural crest competence during hESCs neuralization," PloS One, Nov. 2010, 5:1-17, 17 pgs.

(56) References Cited

OTHER PUBLICATIONS

D'Amour, K.A., et al., "Efficient differentiation of human embryonic stem cells to definitive endoderm," Nature Biotechnology, 2005, 23:1534-1541, 9 pgs.

D'Amour, K.A., et al., "Production of pancreatic hormone-expressing endocrine cells from human embryonic stem cells," Nat Biotechnol, 2006, 24:1392-1401, 10 pgs.

Dahl, A., et al., "Translational Regenerative Medicine—Hepatic Systems," Chapter 34, Clinical Aspects of Regenerative Medicine, eds. A. Atala, M.D. and J. Allickson, PhD, Elsevier, Inc., 2015, pp. 469-484, 16 pgs.

Date, S., et al., "Mini-Gut Organoids: Reconstitution of the Stem Cell Niche," Annual Review of Cell and Developmental Biology, Nov. 2015, 31:269-289.

Davenport, C., et al., "Anterior-Posterior Patterning of Definitive Endoderm Generated from Human Embryonic Stem Cells Depends on the Differential Signaling of Retinoic Acid, Wnt-, and BMP-Signaling," Stem Cells, 2016, 34:2635-2647, 13 pgs.

De Santa Barbara, P., et al., "Development and differentiation of the intestinal epithelium," Cell Mol Life Sci, 2003, 60(7):1322-1332, 12 pgs.

Dedhia, P.H., et al., "Organoid Models of Human Gastrointestinal Development and Disease," Gastroenterology, 2016, 150:1098-1112, 15 pgs.

Dekaney, C.M., et al., "Expansion of intestinal stem cells associated with long-term adaptation following ileocecal resection in mice," Am J Physiol Gastrointest Liver Physiol, Sep. 13, 2007, 293:G1013-G1022, 10 pgs.

Denham, M., et al., "Multipotent caudal neural progenitors derived from human pluripotent stem cells that give rise to lineages of the central and peripheral nervous system," Stem Cells, Mar. 5, 2015, 33:1759-1770, 12 pgs.

Dessimoz, J., et al., "FGF signaling is necessary for establishing gut tube domains along the anterior-posterior axis in vivo," Mech Dev, 2006, 123:42-55, 14 pgs.

Discher, D.E., et al., "Growth Factors, Matrices, and Forces Combine and Control Stem Cells," Science, Jun. 2009, 324:1673-1677, 5 pgs.

Eberhard, J., et al., "A cohort study of the prognostic and treatment predictive value of SATB2 expression in colorectal cancer," British Journal of Cancer, 2012, 106:931-938, 8 pgs.

Eicher, A.K., et al., "Translating Developmental Principles to Generate Human Gastric Organoids," Cellular and Molecular Gastroenterology and Hepatology, 2018, 5(3):353-363, 11 pgs.

Elbashir, S.M., et al., "Functional anatomy of siRNAs for mediating efficient RNAi in *Drosophila melanogaster* embryo lysate," EMBO J., 2001, 20(23):6877-6888, 12 pgs.

Evans, M.J., et al., "Establishment in culture of pluripotent cells from mouse embryos," Nature, 1981, 292:154-156, 3 pgs.

Ezashi, T., et al., "Low $O_2$ tensions and the prevention of differentiation of hES cells," PNAS, Mar. 2005, 102(13):4783-4788, 6 pgs.

Fatehullah, A., et al., "Organoids as an in vitro model of human development and disease," Nature Cell Biology, Mar. 2106, 18(3):246-254, 9 pgs.

Finkbeiner, S.R., et al., "A Gutsy Task: Generating Intestinal Tissue from Human Pluripotent Stem Cells," Dig Dis Sci, 2013, 58:1176-1184, 9 pgs.

Finkbeiner, S.R., et al., "Stem Cell-Derived Human Intestinal Organoids as an Infection Model for Rotaviruses," mBio, Jul./Aug. 2012, 3(4):e00159-12, 6 pgs.

Fordham, R.P., et al., "Transplantation of expanded fetal intestinal progenitors contributes to colon regeneration after injury," Cell Stem Cell, Dec. 5, 2013, 13:734-744, 11 pgs.

Fu, M., et al., "Embryonic development of the ganglion plexuses and the concentric layer structure of human gut: a topographical study," Anatomy and Embryology, Feb. 27, 2004, 208:33-41, 10 pgs.

Fu, M., et al., "*HOXB5* expression is spatially and temporarily regulated in human embryonic gut during neural crest cell colonization and differentiation of enteric. neuroblasts," Developmental Dynamics, 2003, 228:1-10, 10 pgs.

Furness, J.B., "The enteric nervous system and neurogastroenterology," Nature Reviews/Gastroenterology & Hepatology, May 2012, 9:286-294, 9 pgs.

Gessner, R.C., et al., "Functional ultrasound imaging for assessment of extracellular matrix scaffolds used for liver organoid formation," Biomaterials, 2013, 34:9341-9351, 11 pgs.

Gori, M., et al., "Investigating nonalcoholic Fatty Liver Disease in a Liver-on-a-Chip Microfluidic Device," PLOS One, Jul. 2016, 11(7):e0159729, 15 pgs.

Gouon-Evans, V., et al., "BMP-4 is required for hepatic specification of mouse embryonic stem cell-derived definitive endoderm," Nature Biotechnology, Nov. 2006, 24(11):1402-1411, 10 pgs.

Gracz, A.D., et al., "Brief report: CD24 and CD44 mark human intestinal epithelial cell populations with characteristics of active and facultative stem cells," Stem Cells, Apr. 4, 2013, 31:2024-2030, 7 pgs.

Gracz, A.D., et al., "*Sox9* Expression Marks a Subset of CD24-expressing Small Intestine Epithelial Stem Cells the Form Organoids in vitro," Am J Physiol Gastroint Liver Physiol, 2010, 298:G590-600.

Gradwohl, G., et al., "*neurogenin3* is required for the development of the four endocrine cell lineages of the pancreas," Proc Natl Acad Sci USA, 2000, 97:1607-1611, 5 pgs.

Green, M.D., et al., "Generation of anterior foregut endoderm from human embryonic and induced pluripotent stem cells," Nature Biotechnology, Mar. 2011, 29(3):267-272, 7 pgs.

Gregorieff, A., et al., "Wnt signaling in the intestinal epithelium: from endoderm to cancer," Genes & Dev., 2005, 19:877-890, 15 pgs.

Groneberg, D.A., et al., "Intestinal peptide transport: ex vivo uptake studies and localization of peptide carrier PEPT1," Am J Physiol Gastrointest Liver Physiol, Sep. 2001, 281:G697-G704, 8 pgs.

Grosse, A.S., et al., "Cell dynamics in fetal intestinal epithelium: implications for intestinal growth and morphogenesis," Development, 2011, 138:4423-4432, 10 pgs.

Guilak, F., et al., "Control of Stem Cell Fate by Physical Interactions with the Extracellular Matrix," Cell Stem Cell, Jul. 2009, 5:17-26, 10 pgs.

Han, M-E., et al., "Gastric stem cells and gastric cancer stem cells," Anatomy & Cell Biology, 2013, 46:8-18, 11 pgs.

Hannon, G.J., "RNA interference," Nature, 2002, 418:244-251, 8 pgs.

Hannan, N.R.F., et al., "Generation of Multipotent Foregut Stem Cells from Human Pluripotent Stem Cells," Stem Cell Reports, Oct. 2013, 1:293-306, 14 pgs.

Hao, M.M., et al., "Development of enteric neuron diversity," J. Cell. Mol. Med., 2009 13:1193-1210, 18 pgs.

Hardy, T., et al., "Nonalcoholic fatty liver disease: new treatments," Curr Opin Gastroenterol, May 2015, 31(3):175-183, 9 pgs.

Haveri, H., et al., "Transcription factors GATA-4 and GATA-6 in normal and neoplastic human gastrointestinal mucosa," BMC Gastroenterlology, 2008, 8:9.

Hockemeyer, D., et al., "Genetic engineering of human ES and iPS cells using TALE nucleases," Nat Biotechnol., 2012, 29:731-734, 8 pgs.

Howell, J.C., et al., "Generating intestinal tissue from stem cells: potential for research and therapy," Regen Med., 6(6):743-755, 22 pgs.

Huch, M., et al., "Modeling mouse and human development using organoid cultures," Development, 2015, 142:3113-3125, 13 pgs.

Huch, M., et al., "Lgr5$^+$liver stem cells, hepatic organoids and regenerative medicine," Regen. Med., 2013, 8(4):385-387, 3 pgs.

Huebsch, N., et al., "Automated video-based analysis of contractility and calcium flux in human-induced pluripotent stem cell-derived cardiomyocytes cultured over different spatial scales," Tissue Engineering: Part C, 2015, 21:467-479, 15 pgs.

Hutvagner, G., et al., "A microRNA in a Multiple-Turnover RNAi Enzyme Complex," Science, Sep. 20, 2002, 297:2056-2060, 6 pgs.

Jenny, M., et al., "Neurogenin3 is differentially required for endocrine cell fate specification in the intestinal and gastric epithelium," EMBO J, 2002, 21(23):6338-6347, 10 pgs.

(56) References Cited

OTHER PUBLICATIONS

Johannesson, M., et al., "FGF4 and Retinoic Acid Direct Differentiation of hESCs into PDX1-Expressing Foregut Endoderm in a Time- and Concentration-Dependent Manner," PLoS One, Mar. 2009, 4(3):1-13, 13 pgs.

Johansson, K.A., et al., "Temporal Control of Neurogenin3 Activity in Pancreas Progenitors Reveals Competence Windows for the Generation of Different Endocrine Cell Types," Dev Cell, 2007, 12:457-465, 9 pgs.

Johnson, L.R., et al., "Stimulation of rat oxyntic gland mucosal growth by epidermal growth factor," Am. J. Physiol., 1980, 238:G45-49, 5 pgs.

Jung, P., et al., "Isolation and in vitro expansion of human colonic stem cells," Nature Medicine, Oct. 2011, 17:1225-1227, 3 pgs.

Juno, R.J., et al., "A serum factor after intestinal resection stimulates epidermal growth factor receptor signaling and proliferation in intestinal epithelial cells," Surgery, Aug. 2002, 132:377-383, 7 pgs.

Juno, R.J., et al., "A serum factor(s) after small bowel resection induces intestinal epithelial cell proliferation: effects of timing, site, and extent of resection," Journal of Pediatric Surgery, Jun. 2003, 38:868-874, 7 pgs.

Kabouridis, P.S., et al., "Microbiota controls the homeostasis of glial cells in the gut lamina propria," Neuron, Jan. 21, 2015, 85:289-295, 8 pgs.

Kaji, K., et al., "Virus-free induction of pluripotency and subsequent excision of reprogramming factors," Nature, Apr. 2009, 458:771-775, 6 pgs.

Katoh, M., "WNT Signaling in Stem Cell Biology and Regenerative Medicine," Current Drug Targets, 2008, 9(7):565-570, 6 pgs.

Kawaguchi, Y., et al., "The role of the transcriptional regulator Ptf1a in converting intestinal to pancreatic progenitors," Nat Genet, 2002, 32:128-134, 7 pgs.

Kim, T-H., et al., "Stomach development, stem cells and disease," Development, 2016, 143:554-565, 12 pgs.

Klimanskaya, I., et al., "Human embryonic stem cells derived without feeder cells," Lancet, 2005, 365:1636-1641, 6 pgs.

Koike, M., et al., "Effects of mechanical strain on proliferation and differentiation of bone marrow stromal cell line ST2," J Bone Miner Metab, 2005, 23:219-225, 7 pgs.

Kolahchi, A.R., et al., "Microfluidic-Bases Multi-Organ Platforms for Drug Discovery," Micromachines, 2016, 7(162):1-33, 33 pgs.

Koo, B-K, et al., "Controlled gene expression in primary *Lgr5* organoid cultures," Nature Methods, Jan. 1, 2012, 9(1):81-83, XP055225249, 5 pgs.

Kosinski, C., et al., "Indian hedgehog regulates intestinal stem cell fate through epithelial-mesenchymal interactions during development," Gastroenterology, Sep. 2010, 139:893-903, 17 pgs.

Kostrzewski, T., et al., "Three-dimensional perfused human in vitro model of non-alcoholic fatty liver disease," World J Gastroenterol, 2017, 23(2):204-215, 13 pgs.

Kovalenko, P.L., et al., "The Correlation Between the Expression of Differentiation Markers in Rat Small Intestinal Mucosa and the Transcript Levels of Schlafen 3," JAMA Surg., Sep. 4, 2013, 148:1013-1019, 7 pgs.

Kretzschmar, K., et al., "Organoids: Modeling Development and the Stem Cell Niche in a Dish," Developmental Cell, Sep. 2016, 38:590-600, 11 pgs.

Kroon, E., et al., "Pancreatic endoderm derived from human embryonic stem cells generates glucose-responsive insulin secreting cells in vivo," Nat Biotechnol, 2008, 26(4):443-52.

Kubo, A., et al., "Development of definitive endoderm from embryonic stem cells in culture," Development, 2004, 131:1651-1662, 12 pgs.

Kudoh, T., et al., "Distinct roles for Fgf, Wnt and retinoic acid in posteriorizing the neural ectoderm," Development, 2002, 129:4335-4346, 12 pgs.

Kumar, M., et al., "Signals from lateral plate mesoderm instruct endoderm toward a pancreatic fate," Dev Biol, 2003, 259:109-122, 14 pgs.

Kuratnik, A., et al., "Intestinal organoids as tissue surrogates for toxicological and pharmacological studies," Biochemical Pharmacology, 2013, 85:1721-1726, 6 pgs.

Lahar, N., et al., "Intestinal suhepithelial myofibroblasts support in vitro and in vivo growth of human small intestinal epithelium," PLoS One, Nov. 2011, 6:e26898, 9 pgs.

Lambert, P.F., et al., "Using an immortalized cell line to study the HPV life cycle in organotypic 'raft' cultures," Methods in Molecular Medicine, 2005, 119:141-155.

Lancaster, M.A., et al., "Organogenesis in a dish: modeling development and disease using organoid technologies," Science, Jul. 18, 2014, 345:283 & 1247125-1-9, 11 pgs.

Lavial, F., et al., "Chicken embryonic stem cells as a non-mammalian embryonic stem cell model," Develop. Growth Diff., 2010, 52:101-114, 14 pgs.

Le Douarin, N.M., et al., "Neural crest cell plasticity and its limits," Development 131, 2004, 4637-4650, 14 pgs.

Lee, C. S., et al., "*Neurogenin 3* is essential for the proper specification of gastric enteroendocrine cells and the maintenance of gastric epithelial cell identity," Genes Dev, 2002, 16:1488-1497, 11 pgs.

Lee, G., et al., "Isolation and directed differentiation of neural crest stem cells derived from human embryonic stem cells," Nature Biotechnology, Dec. 2007, 25:1468-1475, 9 pgs.

Levin, D.E., et al., "Human tissue-engineered small intestine forms from postnatal progenitor cells," Journal of Pediatric Surgery, 2013, 48:129-137, 9 pgs.

Li, Y., et al., "In vitro organogenesis from pluripotent stem cells," Organogenesis, Jun. 2014, 10(2):159-163, 5 pgs.

Li, Z., et al., "SATB2 is a sensitive marker for lower gastrointestinal well-differentiated neuroendocrine tumors," Int J Clin Exp Pathol, 2015, 8(6):7072-7082, 11 pgs.

Lin, C., et al., "The application of engineered liver tissues for novel drug discovery," Expert Opinion on Drug Discovery, 2015, 10(5):519-540.

Lindley, R.M., et al., "Human and Mouse Enteric Nervous System Neurosphere Transplants Regulate the Function of Aganglionic Embryonic Distal Colon," Gastroenterology, Jul. 2008, 135(1):205-216, XP022823118, 18 pgs.

Liu, J., et al., "A Small-Molecule Agonist of the Wnt Signaling Pathway," Angew Chem Int Ed Engl., 2005, 44(13):1987-1990, 4 pgs.

Logan, C.Y., et al., "The Wnt Signaling Pathway in Development and Disease," Annu. Rev. Cell Dev. Biol., 2004, 20:781-810, 32 pgs.

Longmire, T.A., et al., "Efficient Derivation of Purified Lung and Thyroid Progenitors from Embryonic Stem Cells," Stem Cell, 2012, 10:398-411, 14 pgs.

López-Díaz, L., et al., "Intestinal Neurogenin 3 directs differentiation of a bipotential secretory progenitor to endocrine cell rather than goblet cell fate," Dev Biol. 2007, 309:298-305, 8 pgs.

Lu, Y., et al., "A Novel 3D Liver Organoid System for Elucidation of Hepatic Glucose Metabolism," Biotechnol Bioeng., Feb. 2012, 109(2):595-604, 21 pgs.

Ludwig, T.E., et al, "Derivation of human embryonic stem cells in defined conditions," Nat Biotechnol, 2006, 24:185-187, 3 pgs.

Ludwig, T.E., et al., "Feeder-independent culture of human embryonic stem cells," Nat Methods, 2006, 3:637-646, 10 pgs.

Lui, V.C., et al., "Perturbation of hoxb5 signaling in vagal neural crests down-regulates ret leading to intestinal hypoganglionosis in mice," Gastroenterology, 2008, 134:1104-1115, 12 pgs.

Luo, X., et al., "Generation of endoderm lineages from pluripotent stem cells," Regenerative Medicine, 2017, 12(1):77-89, 13 pgs.

Mahe, M.M., et al., "Establishment of gastrointestinal epithelial organoids," Current Protocols in Mouse Biology, 2013, 3(4):217-240, XP002750112, 31 pgs.

Majumdar, A.P.N., "Postnatal Undernutrition: Effect of Epidermal Growth Factor on Growth and Function of the Gastrointestinal Tract in Rats," J. Pediatr. Gastroenterol. Nutr., 1984, 3:618-625, 8 pgs.

Martin, G.R., "Teratocarcinomas and mammalian embryogenesis," Science, 1980, 209:768-776, 9pgs.

Martín, M., et al., "Dorsal pancreas agenesis in retinoic acid-deficient *Raldh2* mutant mice," Dev Biol., 2005, 284:399-411, 13 pgs.

(56) References Cited

OTHER PUBLICATIONS

McCauley, H.A., et al., "Pluripotent stem cell-derived organoids: using principles of developmental biology to grow human tissues in a dish," Development, 2017, 144:958-962, 5 pgs.

McCracken, K.W., et al., "Generating human intestinal tissue from pluripotent stem cells in vitro," Nature Protocols, 2011, 6(12):1920-1928, 19 pgs.

McCracken, K.W., et al., "Mechanisms of embryonic stomach development," Seminars in Cell & Development Biology, 2017, 66:36-42, 7 pgs.

McCracken, K.W., et al., "Modelling human development and disease in pluripotent stem-cell-derived gastric organoids," Nature, Oct. 29, 2014, 516(7531):400-404, XP055210509, 30 pgs.

McCracken, K.W., et al., "Wnt/β-catenin promotes gastric fundus specification in mice and humans," Nature, Jan. 2017, 541(7636):182-187, 31 pgs.

McCracken, K.W., "Mechanisms of endoderm patterning and directed differentiation of human stem cells into foregut tissues," Dissertation, Graduate School of the University of Cincinnati, Jun. 19, 2014, 185 pgs.

McKeown, S.J., et al., "Hirschsprung disease: a developmental disorder of the enteric nervous system," Wiley Interdisciplinary Reviews Developmental Biology, Jan./Feb. 2013, 2:113-129, 17 pgs.

McLin, V.A. et al., "The Role of the Visceral Mesoderm in the Development of the Gastrointestinal Tract," Gastroenterology, 2009, 136:2074-2091, 18 pgs.

McLin, V.A., et al., "Repression of Wnt/β-catenin signaling in the anterior endoderm is essential for liver and pancreas development," Development, 2007, 134:2207-2217, 11 pgs.

McManus, M.T., et al., "Gene Silencing in Mammals by Small Interfering RNAs," Nat. Rev. Genet., Oct. 2002, 3:737-747, 13 pgs.

Meerbrey, K.L., et al., "The pINDUCER lentiviral toolkit for inducible RNA interference in vitro and in vivo," Proc Natl Acad Sci USA, 2011, 108:3665-3670, 6 pgs.

Mica, Y., et al., "Modeling neural crest induction, melanocyte specification and disease-related pigmentation defects in hESCs and patient-specific iPSCs," Cell Reports, Apr. 25, 2013, 3:1140-1152, 27 pgs.

Micallef, S.J., et al., "Endocrine cells develop within pancreatic bud-like structures derived from mouse ES cells differentiated in response to BMP4 and retinoic acid," Stem Cell Research, 2007, 1:25-36, 12 pgs.

Mills, J.C., et al., "Gastric Epithelial Stem Cells," Gastroenterology, 2011, 140:412-424, 13 pgs.

Miyabayashi, T., et al., "Wnt/β-catenin/CBP signaling maintains long-term murine embryonic stem cell pluripotency," Proc Natl Acad Sci USA, 2007, 104(13):5668-5673, 6 pgs.

Molotkov, A., et al., "Retinoic Acid Generated by *Raldh2* in Mesoderm is Required for Mouse Dorsal Endodermal Pancreas Development," Dev Dyn, 2005, 232:950-957, 8 pgs.

Mou, H., et al., "Generation of Multipotent Lung and Airway Progenitors from Mouse ESCs and Patient-Specific Cystic Fibrosis iPSCs," Stem Cell, 2012, 10:385-397, 13 pgs.

Mudaliar, S., et al., "Efficacy and Safety of the Farnesoid X Receptor Agonist Obeticholic Acid in Patients with Type 2 Diabetes and Nonalcoholic Fatty Liver Disease," Gastroenterology, 2013, 145:574-582, 10 pgs.

Mullin, E., "Tiny Human Esophagus Grown in the Lab—Here's Why: Miniature versions of the organ that guides food to the stomach could help scientists treat a variety of medical ailments," National Geographic, Sep. 20, 2018, downloaded from https://www.nationalgeographic.com/science/2018/09/news-human-esophagus-grown-lab-stem-cells-cancer-health.html, 5 pgs.

Munera, J.O., et al., "Differentiation of Human Pluripotent Stem Cells into Colonic Organoids via Transient Activation of BMP Signaling," Cell Stem Cell, Jul. 2017, 21(1):51-64.e6, 21 pgs.

Munera, J.O., et al., "Generation of Gastrointestinal Organoids from Human Pluripotent Stem Cells," Organ Regeneration, In: Tsuji, T., (eds), Organ Regeneration. Methods in Molecular Biology, vo. 1597, Humana Press, New York, NY, 2017, 11 pgs.

Muñoz, M., et al., "Conventional pluripotency markers are unspecific for bovine embryonic-derived cell-lines," Theriogenology, 2008, 69:1159-1164, 6 pgs.

Nandivada, P., et al., "Treatment of Parenteral Nutrition-Associated Liver Disease: The Role of Lipid Emulsions," Advances in Nutrition, Reviews from ASN EB 2013 Symposia, pp. 711-717, 7 pgs.

Neiiendam, J.L., et al., "An NCAM-derived FGF-receptor agonist, the FGL-peptide, induces neurite outgrowth and neuronal survival in primary rat neurons," J. Neurochem., 2004, 91(4):920-935, 17 pgs.

Neuschwander-Tetri, B.A., et al., "Farnesoid X nuclear receptor ligand obeticholic acid for non-cirrhotic, non-alcoholic steatohepatitis (FLINT): a multicentre, randomised, placebo-controlled trial," Lancet, 2015, 385:956-965, 10 pgs.

Noguchi, T-A.K., et al., "Generation of stomach tissue from mouse embryonic stem cells," Nature Cell Biology, 2015, 17(8):984-993, XP055225165, 20 pgs.

Obermayr, F., et al., "Development and developmental disorders of the enteric nervous system," Nature Reviews/Gastroenterology & Hepatology, Jan. 2013, 10:43-57, 15 pgs.

Ogaki, S., et al., "Wnt and Notch Signals Guide Embryonic Stem Cell Differentiation into the Intestinal Lineages," Stem Cells, 2013, 31:1086-1096, 11 pgs.

Okita, K., et al., "An Efficient Nonviral Method to Generate Integration-Free Human-Induced Pluripotent Stem Cells from Cord Blood and Peripheral Blood Cells," Stem Cells, 2013, 31:458-466, 9 pgs.

Okita, K., et al., "Generation of Mouse Induced Pluripotent Stem Cells Without Viral Vectors," Science, 2008, 322(5903):949-953, 6 pgs.

Olbe, L., et al., "A Mechanism by Which *Helicobacter pylori* Infection of the antrum Contributes to the Development of Duodenal Ulcer," Gastroenterology, 2001, 110:1386-1394, 9 pgs.

Ootani, A. et al., "Sustained in vitro intestinal epithelial culture within a Wnt-dependent stem cell niche," Nat Med, 2009, 15:701-706, 14 pgs.

Paddison, P.J., et al., "RNA interference: the new somatic cell genetics?", Cancer Cell, 2002, 2:17-23, 7 pgs.

Pai, R., et al., "Deoxycholic Acid Activates β-Catenin Signaling Pathway and Increases Colon Cell Cancer Growth and Invasiveness," Mol Biol Cell., 2004, 15(5):2156-2163, 8 pgs.

Paris, D.B.B.P., et al., "Equine embryos and embryonic stem cells: Defining reliable markers of pluripotency," Theriogenology, 2010, 74:516-524, 9 pgs.

Park, H.R., et al., "Lipotoxicity of Palmaitic Acid on Neural Progenitor Cells and Hippocampal Neurogenesis," Toxicol Res, 2011, 27(2):103-110, 8 pgs.

Park, J.S., et al., "Differential Effects of Equiaxial and Uniaxial Strain on Mesenchymal Stem Cells," Biotechnology and Bioengineering, Nov. 2004, 88(3):359-368, 10 pgs.

Park, J.S., et al., "The effect of matrix stiffness on the differentiation of mesenhymal stem cells in response to TGF-β," Biomaterials, 2011, 32:3921-3930, 10 pgs.

Park, K.I., et al., "Acute injury directs the migration, proliferation, and differentiation of solid organ stem cells: Evidence for the effect of hypoxia-ischemia in the CNS on clonal "reporter" neural stem cells," Experimental Neurology, 2006, 199:159-178, 23 pgs.

Parkin, D.M., "The global health burden of infection-associated cancers in the year 2002," Int. J. Cancer, 2006, 118:3030-3044, 15 pgs.

Pastula, A., et al., "Three-Dimensional Gastrointestinal Organoid Culture in Combination with Nerves or Fibroblasts: A Method to Characterize the Gastrointestinal Stem Cell Niche," Stem Cells International, 2016, 16 pgs.

Peek, R.M., Jr., "*Helicobacter pylori* infection and disease: from humans to animal models," Dis Model Mech, 2008, 1:50-55, 6 pgs.

Peek, R.M., Jr., et al., "*Helicobacter pylori* cagA+ Strains and Dissociation of Gastric Epithelial Cell Proliferation From Apoptosis," J. Natl. Cancer Inst., 1997, 89:863-868, 7 pgs.

(56) References Cited

OTHER PUBLICATIONS

Pennisi, C.P., Ph.D., et al., "Uniaxial Cyclic Strain Drives Assembly and Differentiation of Skeletal Myocytes," Tissue Engineering: Part A, 2011, 17(19-20):2543-2550, 8 pgs.
Petitte, J.N., et al., "Avian pluripotent stem cells," Mech. of Develop., 2004, 121:1159-1168, 10 pgs.
Pompaiah, M., et al., "Gastric Organoids: An Emerging Model System to Study *Helicobacter pylori* Pathogenesis," Molecular Pathogenesis and Signal Transduction by Helicobacter pylori, Current Topics in Microbiology and Immunology, N. Tegtmeyer, et al., (eds.), 2017, pp. 149-168.
Pulikkot, S., "Establishment of a 3D Culture Model of Gastric Stem Cells Supporting Their Differentiation into Mucous Cells Using Microfibrous Polycaprolactone Scaffold," Dissertation, United Arab Emirates University, College of Medicine and Health Sciences, May 2015, 187 pgs. (4 parts: Part 1—58 pgs; Part 2—69 pgs; Part 3—31 pgs; Part 4—29 pgs.).
Qi, M-C., et al., "Mechanical strain induces osteogenic differentiation: Cbfa1 and Ets-1 expression in stretched rat mesenchymal stem cells," Int J Oral Maxillofac Surg, 2008, 1 37:453-458, 6 pgs.
Ramachandran, S.D., et al., "In Vitro Generation of Functional Liver Organoid-Like Structures Using Adult Human Cells," Plos One, Oct. 2015, 14 pgs.
Rankin, S.A., et al., "Timing is everything: Reiterative Wnt, BMP and RA signaling regulate developmental competence during endoderm organogenesis," Developmental Biology, Feb. 1, 2018, 434(1):121-132, 12 pgs.
Ray, K., "Engineering human intestinal organoids with a functional ENS," Nature Reviews Gastroenterology & Hepatology, Nov. 2016, 1 pg.
Reilly, G.C., et al., "Intrinsic extracellular matrix properties regulate stem cell differentiation," Journal of Biomechanics, 2010, 43:55-62, 8 pgs.
Rennert, K., et al., "A microfluidically perfused three dimensional human liver model," Biomaterials, 2015, 71:119-131, 13 pgs.
Richards, M., et al., "The Transcriptome Profile of Human Embryonic Stem Cells as Defined by SAGE," Stem Cells, 2004, 22:51-64, 14 pgs.
Rohrschneider, M.R., et al., "Polarity and cell fate specification in the control of *C. elegans* gastrulation," Dev. Dyn., 2009, 238(4):789-796, 15 pgs.
Saenz, J.B., et al., "Stomach growth in a dish: A protocol has been developed to grow structures that resemble the main part of the stomach in vitro from human embryonic stem cells—an advance that provides insights into stomach development," Nature, Jan. 2017, 541:160-161, 2 pgs.
Saffrey, M.J., "Cellular changes in the enteric nervous system during ageing," Developmental Biology, 2013, 382:344-355, 12 pgs.
Saha, S., et al., "Inhibition of Human Embryonic Stem Cell Differentiation by Medical Strain," Journal of Cellular Physiology, 2006, 206:126-137, 12 pgs.
Saito, M., et al., "Reconstruction of liver organoid using a bioreactor," World J Gastroenterol, Mar. 2006, 12(12):1881-1888, 8 pgs.
Sampaziotis, F., et al., "Potential of Human Induced Pluripotent Stem Cells in Studies of Liver Disease," Hepatology, Jul. 2015, 62(1):303-311, 9 pgs.
Sancho, E., et al., "Signaling Pathways in Intestinal Development and Cancer," Annu. Rev. Cell Dev. Biol., 2004, 20:695-723, 31 pgs.
Sandoiu, A., "Scientists create human esophagus in stem cell first," Medical News Today, Sep. 21, 2018, downloaded from https://www.medicalnewstoday.com/articles/323118.php, 4 pgs.
Sasai, Y., "Next-Generation Regenerative Medicine: Organogenesis from Stem Cells in 3D Culture," Cell Stem Cell, May 2013, 12:520-530, 11 pgs.
Sasselli, V., et al., "The enteric nervous system," Developmental Biology, Jan. 2012, 366:64-73, 10 pgs.
Sato, T., et al., "Long-term expansion of epithelial organoids from human colon, adenoma, adenocarcinoma, and Barrett's epithelium," Gastroenterology, Nov. 2011, 141:1762-1772, 11 pgs.

Sato, T., et al., "Single Lgr5 stem cells build crypt-villus structures in vitro without a mesenchymal niche," Nature, 2009, 459:262-265, 5 pgs.
Schlieve, C.R., et al., "Created of Warm Blood and Nerves: Restoring an Enteric Nervous System in Organoids," Cell Stem Cell, Jan. 2017, 20:5-7, 3 pgs.
Schmelter, M., et al., "Embryonic stem cells utilize reactive oxygen species as transducers of mechanical strain-induced cardiovascular differentiation," The FASEB Journal, Jun. 2006, 20(8):1182-1184, 16 pgs.
Schonhoff, S.E., et al., "*Neurogenin* 3-expressing progenitor cells in the gastrointestinal tract differentiate into both endocrine and non-endocrine cell types," Dev Biol, 2004, 270:443-454, 12 pgs.
Schumacher, M.A., et al., "Gastric Sonic Hedgehog Acts as a Macrophage Chemoattractant During the Immune Response to *Helicobacter pylori*," Gastroenterology, 2012, 142:1150-1159, 16 pgs.
Schuppan, D., et al., "Non-alcoholic steatohepatitis: Pathogenesis and novel therapeutic approaches," Journal of Gastroenterology and Hepatology, 2013, 28(Suppl 1):68-76, 9 pgs.
Shah, S.B., et al., "Cellular self-assembly and biomaterials-based organoid models of development and diseases," Acta Biomaterialia, 2017, 53:29-45, 17 pgs.
Shan, J., et al., "Identification of a Specific Inhibitor of the Dishevelled PDZ Domain," Biochemistry, 2005, 44(47):15495-15503, 9 pgs.
Shimizu, N., et al., "Cyclic strain induces mouse embryonic stem cell differentiation into vascular smooth muscle cells by activating PDGF receptor β," J Appl Physiol, 2008, 104:766-772, 7 pgs.
Si-Tayeb, K., et al., "Highly Efficient Generation of Human Hepatocyte-Like Cells from Induced Pluripotent Stem Cells," Hepatology, 2010, 51:297-305, 9 pgs.
Singh, S., et al., "Comparative Effectiveness of Pharmacological Interventions for Nonalcoholic Steatohepatitis: A Systematic Review and Network Meta-analysis," Hepatology, Nov. 2015, 62(5):1417-1432, 16 pgs.
Simon-Assmann, P., et al., "In vitro models of intestinal epithelial cell differentiation," Cell Biol. Toxicol., 2007, 23:241-256, 16 pgs.
Sinagoga, K.L., et al., "Generating human intestinal tissues from pluripotent stem cells to study development and disease," The EMBO Journal, 2015, 34(9):1149-1163, 15 pgs.
Skardal, A., et al., "Organoid-on-a-chip and body-on-a-chip systems for drug screening and disease modeling," Drug Discovery Today, Sep. 2016, 21(9):1399-1411, 13 pgs.
Snoeck, H-W., "Generation of Anterior Foregut Derivatives from Pluripotent Stem Cells," Stem Cells Handbook, S. Sell (ed.), 2013, pp. 161-175.
Snykers, S., et al., "In Vitro Differentiation of Embryonic and Adult Stem Cells into Hepatocytes: State of the Art," Stem Cells, 2009, 27:577-605, 29 pgs.
Sonntag, F., et al., "Design and prototyping of a chip-based multi-micro-organoid culture system for substance testing, predictive to human (substance) exposure," Journal of Biotechnology, 2010, 148:70-75, 6 pgs.
Soto-Gutierrez, A., et al., "Engineering of an Hepatic Organoid to Develop Liver Assist Devices," Cell Transplant., 2010, 19(6):815-822, 12 pgs.
Spear, P.C., et al., "Interkinetic nuclear migration: A mysterious process in search of a function," Develop. Growth Differ., 2012, 54:306-316, 12 pgs.
Speer, M.D., A.L., et al., "Murine Tissue-Engineered Stomach Demonstrates Epithelial Differentiation," Journal of Surgical Research, Mar. 22, 2011, 171(1):6-14, XP028317226, 9 pgs.
Spence, J.R., et al., "Directed differentiation of human pluripotent stem cells into intestinal tissue in vitro," Nature, 2011, 470:105-109, 13 pgs.
Spence, J.R., et al., "Translational Embryology: Using Embryonic Principles to Generate Pancreatic Endocrine Cells from Embryonic Stem Cells," Developmental Dynamics, 2007, 236:3218-3227, 10 pgs.
Stadtfeld, M., et al., "Induced pluripotent stem cells generated without viral integrafion," Science, 2008, 322(5903):945-949, 12 pgs.

(56) References Cited

OTHER PUBLICATIONS

Stark, R., et al., "Development of an endoluminal intestinal lengthening capsule," Journal of Pediatric Surgery, 2012, 47:136-141, 6 pgs.
Sugawara, T., et al., "Organoids recapitulate organs?," Stem Cell Investig, 2018, vol. 5, Iss. 3, 4 pgs.
Sui, L., et al., "Signaling pathways during maintenance and definitive endoderm differentiation of embryonic stem cells," Int J Dev Bio, 2013, 57:1-12, 12 pgs.
Sun, Y., et al., "Genome engineering of stem cell organoids for disease modeling," Protein Cell, 2017, 8(5):315-327, 13 pgs.
Taipale, J., et al., "The Hedgehog and Wnt signalling pathways in cancer," Nature, 2001, 411:349-354, 8 pgs.
Tait, I.S., et al., "Colonic mucosal replacement by syngeneic small intestinal stem cell transplantation," The American Journal of Surgery, Jan. 1994, 167:67-72, 6 pgs.
Tait, I.S., et al., "Generation of neomucosa in vivo by transplantation of dissociated rat postnatal small intestinal epithelium," Differentiation, 1994 56:91-100, 10 pgs.
Takahashi, K. et al., "Induction of Pluripotent Stem Cells from Adult Human Fibroblasts by Defined Factors," Cell, 2007, 131:861-872, 12 pgs.
Takahashi, K., et al., "Induction of Pluripotent Stem Cells from Mouse Embryonic and Adult Fibroblast Cuhures by Defined Factors," Cell, 2006, 126:663-676, 14 pgs.
Takaki, M., et al., "In Vitro Formation of Enteric Neural Network Structure in a Gut-Like Organ Differentiated from Mouse Embryonic Stem Cells," Stem Cells, Jun. 9, 2006, 24(6):1414-1422, XP55241404, 9 pgs.
Tamminen, K., et al., "Intestinal Commitment and Maturation of Human Pluripotent Stem Cells Is Independent of Exogenous FGF4 and R-spondinl," PLOS One, Jul. 2015, 10(7):e0134551, 19 pgs.
Tang, W., et al., "Faithful expression of multiple proteins via 2A-peptide self-processing: a versatile and reliable method for manipulating brain circuits," The Journal of Neuroscience, Jul. 8, 2009, 29:8621-8629, 9 pgs.
Teo, A.K.K., et al., "Activin and BMP4 Synergistically Promote Formation of Definitive Endoderm in Human Embryonic Stem Cells," Stem Cells, 2012, 30:631-642, 12 pgs.
Thomson, J.A., et al., "Embryonic Stem Cell Lines Derived from Human Blastocysts," Science, 1998, 282(5391):1145-1147, 4 pgs.
Tiso, N., et al., "BMP signalling regulates anteroposterior endoderm patterning in zebrafish," Mech Dev, 2002, 118:29-37, 9 pgs.
Toivonen, S., et al., "Activin A and Wnt-dependent specification of human definitive endoderm cells," Experimental Cell Research, 2013, 319:2535-2544, 10 pgs.
Tsakmaki, A., et al., "3D intestinal organoids in metabolic research: virtual reality in a dish," Current Opinion in Pharmacology, 2017, 37:51-58, 8 pgs.
Tuschl, T., et al., "Targeted mRNA degradation by double-stranded RNA in vitro," Genes Dev., 1999, 13:3191-3197, 8 pgs.
Van Breemen, R.B., et al., "Caco-2 cell permeability assays to measure drug absorption," Expert Opin. Drug Metab. Toxicol., Aug. 2005, 1(2):175-185, 11 pgs.
Verzi, M.P., et al., "Role of the Homeodomain Transcription Factor Bapx1 in Mouse Distal Stomach Development," Gastroenterology, 2009, 136:1701-1710, 10 pgs.
Wallace, A.S., et al., "Development of the enteric nervous system, smooth muscle and interstitial cells of Cajal in the human gastrointestinal tract," Cell and Tissue Research, Jan. 26, 2005, 319:367-382, 16 pgs.
Wang, A., et al., "Generating cells of the gastrointestinal system: current approaches and applications for the differentiation of human pluripotent stem cells," J Mol Med, 2012, 90:763-771, 9 pgs.
Wang, F., et al., "Isolation and characterization of intestinal stem cells based on surface marker combinations and colony-formation assay," Gastroenterology, 2013, 145:383-395.e1-e21, 34 pgs.
Wang, J., et al., "Mutant Neurogenin-3 in Congenital Malabsorptive Diarrhea," New England Journal of Medicine, 2006, 355:270-280, 11 pgs.

Wang, Z., et al., "Retinoic acid regulates morphogenesis and patterning of posterior foregut derivatives," Dev Biol, 2006, 297:433-445.
Ward, D.F., Jr., et al., "Mechanical Strain Enhances Extracellular Matrix-Induced Gene Focusing and Promotes Osteogenic Differentiation of Human Mesenchymal Stem Cells Through an Extracellular-Related Kinase-Dependent Pathway," Stem Cells and Development, 2007, 16:467-479, 14 pgs.
Warlich, E., et al., "Lentiviral vector design and imaging approaches to visualize the early stages of cellular reprogramming," Mol. Ther., Apr. 2011, 19:782-789, 9 pgs.
Watson, C.L., et al., "An in vivo model of human small intestine using pluripotent stem cells," Nature Medicine, Oct. 19, 2014, 20(11):1310-1314, XP055241417, 7 pgs.
Wells, J.M., et al., "Early mouse endoderm is patterned by soluble factors from adjacent germ layers," Development, 2000, 127:1563-1572, 10 pgs.
Wells, J.M., et al., "How to Make an intestine," Development, Feb. 15, 2014, 141(4):752-760, XP055241409, 9 pgs.
Wen, S. et al., "*Helicobacter pylori* virulence factors in gastric carcinogenesis," Cancer Lett., 2009, 282:1-8, 8 pgs.
Willet, S.G., et al., "Stomach Organ and Cell Lineage Differentiation: From Embryogenesis to Adult Homeostasis," Cellular and Molecular Gastroenterology and Hepatolgy, 2016, 2(5):546-559, 14 pgs.
Williamson, R.C.N., et al., "Humoral stimulation of cell proliferation in small bowel after transection and resection in rats," Gastroenterology, 1978, 75:249-254, 6 pgs.
Woltjen, K., et al., "*piggyBac* transposition reprograms fibroblasts to induced pluripotent stem cells," Nature, 2009, 458:766-770, 8 pgs.
Workman, M.J., et al., "Engineered human pluripotent-stem-cell-derived intestinal tissues with a functional enteric nervous system," Nat Med, Jan. 2017, 23(1):49-59, 29 pgs.
Workman, M.J., "Generating 3D human intestinal organoids with an enteric nervous system," Thesis, Graduate School of the University of Cincinnati, Oct. 2014, 61 pgs.
Xia, H.H-X., et al. "Antral-Type Mucosa in the Gastric Incisura, Body, and Fundus (Antralization): A Link Between *Helicobacter pylori* Infection and Intestinal Metaplasia?", Am. J. Gastroenterol., 2000, 95:114-121, 8 ps.
Xinaris, C., et al., "Organoid Models and Applications in Biomedical Research," Nephron, 2015, 130:191-199, 9 pgs.
Yamada, S., et al. "Differentiation of immature enterocytes into enteroendocrine cells by *Pdx1* overexpression," Am. J. Physiol. Gastrointest. Liver Pyshiol., 2001, 281:G229-G236, 8 pgs.
Yin, C., et al., "Hepatic stellate cells in liver development, regeneration, and cancer," The Journal of Clinical Investigation, May 2013, 123(5):1902-1910, 9 pgs.
Young, H.M., et al., "Expression of Ret-, $p75^{NTR}$-, Phox2a-, Phox2b-, and tyrosine hydroxylase-immunoreactivity by undifferentiated neural crest-derived cells and different classes of enteric neurons in the embryonic mouse gut," Developmental Dynamics, 1999, 216:137-152, 16 pgs.
Young, H.M., et al., "GDNF is a chemoattractant for enteric neural cells," Developmental biology, Dec. 19, 2000, 229:503-516, 14 pgs.
Yuan, Y., et al., "Peptic ulcer disease today," Nat Clin Pract Gastroenterol Hepatol, 2006, 3:80-89 10 pgs.
Yui, S., et al., "Functional engraftment of colon epithelium expanded in vitro from a single adult Lgr5(+) stem cell," Nature Medicine, Apr. 2012, 18:618-623, 8 pgs.
Zachos, N.C., et al., "Human Enteroids/Colonoids and Intestinal Organoids Functionally Recapitulate Normal Intestinal Physiology and Pathophysiology," The Journal of Biological Chemistry, Feb. 2016, 291(8):3759-3766, 8 pgs.
Zhang, D., et a., "Neural crest regionalisation for enteric nervous system formation: implications for Hirschsprung's disease and stem cell therapy," Developmental Biology, Jan. 18, 2010, 339:280-294, 15 pgs.
Zhang, Q, et al., "Small-molecule synergist of the Wnt/β-catenin signaling pathway," Proc Natl Acad Sci USA, 2007, 104(18):7444-7448, 6 pgs.

(56) References Cited

OTHER PUBLICATIONS

Zhang, W., et al., "Elastomeric Free-Form Blood Vessels for Interconnecting Organs on Chip Systems," Lab Chip, Apr. 2016, 16(9):1579-1586, 19 pgs.
Zhang, Y. S., et al., "Multisensor-integrated organs-on-chips platforms for automated and continual in situ monitoring of organoid behaviors," PNAS Early Edition, 2017, 10 pgs.
Zhang, Y.S., et al., "Seeking the right context for evaluating nanomedicine: from tissue models in petri dishes to microfluidic organs-on-a-chip," Nanomedicine (Lond.), 2015, 10(5):685-688, 4 pgs.
Zhou, H., et al., "Generation of Induced Pluripotent Stem Cells Using Recombinant Proteins," Cell Stem Cell, 2009, 4(5):381-384, 4 pgs.
Zhou, J., et al., "The Potential for Gut Organoid Derived Interstitial Cells of Cajal in Replacement Therapy," International Journal of Molecular Sciences, Sep. 2017, 18:1-17 pgs.
Zhou, Q., et al., "In vivo reprogramming of adult pancreatic exocrine cells to β-cells," Nature, 2008, 455: 627-632, 6 pgs.
Zorn, A.M., et al., "Vertebrate endoderm develpment and organ formation," Rev Cell Dev Biol, 2009, 25:221-251, 36 pgs.
European Exam Report dated Sep. 28, 2017 for Application No. EP 15728704.6, 4 pgs.
European Exam Report dated Jul. 4, 2018 for Application No. EP 15728704.6, 3 pgs.
European Exam Report dated May 18, 2018 for Application No. EP 15791404.5, 3 pgs.
International Search Report dated Feb. 9, 2012 for Application No. PCT/US2011/035518, 7 pgs.
International Preliminary Report on Patentability and Written Opinion dated Nov. 6, 2012 for Application No. PCT/US2011/035518, 5 pgs.
International Search Report and Written Opinion dated Dec. 15, 2015 for Application No. PCT/US2015/032626, 19 pgs.
International Search Report and Written Opinion dated Jan. 25, 2016 for Application No. PCT/US2015/055956, 16 pgs.
International Preliminary Report on Patentability dated Apr. 18, 2017 for Application No. PCT/US2015/055956, 8 pgs.
International Search Report and Written Opinion dated Aug. 14, 2017 for Application No. PCT/US2017/013109, 17 pgs.
International Search Report and Written Opinion dated Jan. 19, 2018, for Application No. PCT/US2017/059845, 13 pgs.
International Search Report and Written Opinion dated Jan. 29, 2018 for Application No. PCT/US2017/059860, 13 pgs.
International Search Report and Written Opinion dated Jan. 18, 2018 for Application No. PCT/US2017/059865, 12 pgs.
International Search Report and Written Opinion dated Feb. 21, 2018 for Application No. PCT/US2017/064600, 15 pgs.
International Search Report and Written Opinion dated Jun. 14, 2018 for Application No. PCT/US2018/018585, 14 pgs.
International Searching Authority Invitaion to Pay Additional Fees, Where Applicable, Protest Fee, dated Jun. 27, 2018 for Application No. PCT/US2018/029083.
Singaporean Second Written Opinion dated Oct. 19, 2017 for Application No. SG11201609953X, 8 pgs.
Singaporean Second Written Opinion dated Sep. 4, 2018 for Application No. SG11201609953X, 6 pgs.
U.S. Appl. No. 61/332,178, filed May 6, 2010.
U.S. Appl. No. 62/003,719, filed May 28, 2014.
U.S. Appl. No. 62/065,131, filed Oct. 17, 2014.
U.S. Appl. No. 62/332,194, filed May 5, 2016.
Keung, A.J., et al., "Presentation Counts: Microenvironmental Regulation of Stem Cells by Biophysical and Material Cues," Annu. Rev. Cell Dev. Biol., 2010, 26:533-556, 26 pgs.
Barlow, A.J., et al., "Critical numbers of neural crest cells are required in the pathways from the neural tube to the foregut to ensure complete enteric nervous system formation," Development, 2008, 135:1681-1691, 11 pgs.
Burns, A.J., et al., "In ovo transplantation of enteric nervous system precursors from vagal to sacral neural crest results in extensive hindgut colonisation," Development, 2002, 129:2785-2796, 12 pgs.
Kawaguchi, J., et al., "Isolation and propagation of enteric neural crest progenitor cells from mouse embryonic stem cells and embryos," Development, 2010, 137:693-704, 12 pgs.
Merker, S.R., et al., "Gastrointestinal organoids: How they gut it out," Developmental Biology, 2016, 420:239-250, 12 pgs.
Mosher, J.T., et al., "Intrinsic differences among spatially distinct neural crest stem cells in terms of migratory properties, fate-determination, and ability to colonize the enteric nervous system," Dev. Biol., Mar. 2007, 303(1):1-15, 29 pgs.
An, W.F., et al., "Discovery of Potent and Highly Selective Inhibitors of GSK3b," Molecular Libraries, Probe Report, May 2014, 115 pgs.
Chang, H-M., et al., "BMP15 Suppresses Progesterone production by Down-Regulating StAR via ALK3 in Human Granulosa Cells," Molecular Endocrinology, 2013, 27:2093-2104, 12 pgs.
Deng, H., "Mechanisms of retinoic acid on the induction of differentiation of neural stem cells for newborn rat striatum," Chinese Doctoral and Master Dissertations Full-Text Database (Doctoral) Basic Science, Issue 4, Apr. 15, 2006, pp. 1-89. Reference unavailable.
Deng, H. et al., "Effects of all-trans retinoic acid on the differentiation of neural stem cells and the expression of c-myc gene," Chinese Journal of Tissue Engineering Research, Mar. 18, 2007, 11(11):2039-2042. Reference unavailable.
Krausova, M., et al., "Wnt signaling in adult intestinal stem cells and cancer," Cellular Signalling, 2014, 26:570-579, 10 pgs.
Lim, D.A., et al., "Noggin Antagonizes BMP Signaling to Create a Niche for Adult Neurogenesis," Neuron, Dec. 2000, 28:713-726, 14 pgs.
McMahon, J.A., et al., "Noggin-mediated antagonism of BMP signaling is required for growth and patterning of the neural tube and somite," Genes & Development, May 1998, 12:1438-1452, 15 pgs.
Ornitz, D.M., et al., "FGF signaling pathways in endochondral and intramembranous bone development and human genetic disease," Genes & Development, Jun. 2002, 16:1446-1465, 21 pgs.
Pan, Q., *Physiology*, University of Science and Technology of China Press, Jan. 31, 2014, pp. 149-150. Reference unavailable.
Que, J., et al., "Morphogenesis of the trachea and esophagus: current players and new roles for noggin and Bmps," Differentiation, 2006, 74:422-437, 16 pgs.
Raju, R., et al., "A Network Map of FGF-1/FGFR Signaling System," Journal of Signal Transduction, Apr. 2014, 2014:1-16, Article ID 962962, 16 pgs.
Su, N., et al., "Role of FGF/FGFR signaling in skeletal development and homeostatsis: learning from mouse models," Bone Research, 2014, 2:14003, 24 pgs.
Wan, W., et al., "The Role of Wnt Signaling in the Development of Alzheimer's Disease: A Potential Therapeutic Target?", BioMed Research International, 2014:1-9, Article ID 301575, 9 pgs.
Yanagita, M., "Modulator of bone morphogenetic protein activity in the progression of kidney diseases," Kidney International, 2006, 70:989-993, 5 pgs.
Yu, Y., *Chinese Studies on Disease Signaling Pathway and Targeted Therapy*, Anhui Science and Technology Press, May 31, 2013, p. 363. Reference unavailable.
Chinese Office Action, and Preliminary Search Report, dated Jan. 30, 2019 for Application No. CN 201580034910.4, 11 pgs.
Israeli Office Action dated Nov. 29, 2018 for Application No. IL 249253, 8 pgs.
Deward, A.D., et al., "Cellular Heterogeneity in the Mouse Esophagus Implicates the Presence of a Nonquiescent Epithelial Stem Cell Population," Cell Reports, 2014, 9:701-711, 12 pgs.
Trisno, S.L., et al., "Esophageal Organoids from Human Pluripotent Stem Cells Delineate Sox2 Functions during Esophageal Specification," Cell Stem Cell, 2018, 23:501-515, 23 pgs.
International Search Report and Written Opinion dated Jan. 8, 2019 for Application No. PCT/US2018/054635, 16 pgs.
Bain G., "Embryonic Stem Cells Express Neuronal Properties in Vitro," Developmental Biology, 1995, vol. 168, pp. 842-357.

(56) References Cited

OTHER PUBLICATIONS

Burns A.J., et al., "Enteric Nervous System Development: Analysis of the Selective Developmental Potentialities of Vagal and Sacral Neural Crest Cells using Quail-Chick Chimeras," The Anatomical Record, 2001, vol. 262, pp. 16-28.

Burrin D., et al., "Enteral Obeticholic Acid Prevents Hepatic Cholestasis in Total Parenteral Nutrition-Fed Neonatal Pigs", Hepatology, vol. 62, Oct. 2015, p. 307A.

Chauhan R.K., "Genetic and Functional Studies of Hirschsprung Disease", Doctoral Thesis: Department of Clinical Genetics, Erasmus University Rotterdam, the Netherlands, 2016; 202 pages.

Cunningham T.J., et al., "Mechanisms of Retinoic acid Signalling and its Roles in Organ and Limb development," Nature Reviews Molecular Cell Biology, vol. 16, No. 2, Jan. 5, 2015, pp. 110-123.

Dunn, "Cationic Nanoparticles for the Targeting and Delivery of Nucleic Acids to the Pulmonary Endothelium," University of Cincinnati, Sep. 19, 2018, Doctoral Thesis; downloaded from https://etd.ohiolink.edu/apexprod/rws_olink/r/1501/10?clear=10&p10_accession_num=ucin1544098242321181; 160 pages.

Goldstein A.M., et al., "BMP Signaling is Necessary for Neural Crest Cell Migration and Ganglion Formation in the Enteric Nervous System," Mechanisms of Development, 2013, vol. 122, pp. 821-833.

Guan Y., et al., "Human Hepatic Organoids for the Analysis of Human genetic Diseases," JCI Insight, Sep. 7, 2017, vol. 2(17), e94954; 17 pages.

Huang H., "Differentiation of Human Embryonic Stem Cells into Smooth Muscle Cells in Adherent Monolayer Culture," Biochemical and Biophysical Research Communications, 2006, vol. 351 pp. 321-327.

Jones P., et al., "Stromal Expression of Jagged 1 Promotes Colony Formation by Fetal Hematopoietic Progenitor Cells," Blood, Sep. 1, 1998, vol. 92, No. 5, pp. 1505-1511.

Kruitwagen H.S. et al., "SCH-O-5 Long-Term Adult Feline Liver Organoid Cultures for Disease Modelling of Hepatic Lipidosis," Research Communications of the 26th ECVIM-CA Congress, Sep. 2016; ECVIM Abstracts pp. 203-204.

Kruitwagen H.S., et al., "Long-Term Adult Feline Liver Organoid Cultures for Disease Modeling of Hepatic Steatosis", Stem Cell Reports, Apr. 2017, vol. 8(4), pp. 822-830.

Lachmann N., et al., "Large-Scale Hematopoietic Differentiation of Human Induced Pluripotent Stem Cells Provides Granulocytes or Macrophages for Cell Replacement Therapies," Stem Cell Report, Feb. 10, 2015, vol. 4, pp. 282-296.

Lai F.P-L., et al., "Correction of Hirschsprung-Associated Mutations in Human Induced Pluripotent Stem Cells via Clustered Regularly Interspaced Short Palindromic Repeats/Cas9, Restores Neural Crest Cell Function," Gastroenterology, 2017, vol. 153, No. 1, pp. 139-153.

Liu J.A-J. et al., "Identification of GLI Mutations in Patients with Hirschsprung Disease that Disrupt Enteric Nervous System Development in Mice," Gastroenterology, 2015, vol. 149, No. 7, pp. 1837-1848.

McCracken K.W. et al., "Generating Human Intestinal Tissue from Pluripotent Stem Cells in Vitro," Nature Protocols, vol. 6, No. 12, Nov. 10, 2011, pp. 1920-1928.

McCracken K.W., et al., "Modelling Human Development and Disease in Pluripotent Stem-Cell-Derived Gastric Organoids", Nature, Oct. 29, 2014, vol. 516, No. 7531, pp. 400-404.

Mori R., et al., "Micropatterned Organoid Culture of Rat Hepatocytes and HepG2 Cells", Journal of Bioscience and Bioengineering, Sep. 2008, vol. 106(3), pp. 237-242.

Nantasanti S., et al., "Concise Review: Organoids are a Powerful Tool for the Study of Liver Disease and Personalized Treatment Design in Humans and Animals: Organoids for Disease Modeling and Therapy," Stem Cells Translational Medicine, Jan. 21, 2016, vol. 5(3), pp. 325-330.

Okada Y., et al., "Retinoic-Acid-Concentration-Dependent Acquisition of Neural Cell Identity during in Vitro Differentiation of Mouse Embryonic Stem Cells," Developmental Biology, 2004, vol. 275, pp. 124-142.

Paddison P.J., et al., "Short Hairpin Activated Gene Silencing in Mammalian Cells," Methods in Molecular Biology, 2004, vol. 265, pp. 85-100.

Ricchi M., et al., "Differential Effect of Oleic and Palmitic Acid on Lipid Accumulation and Apoptosis in Cultured Hepatocytes," Journal of Gastroenterology and Hepatology, May 2009, vol. 24(5), pp. 830-840.

Sherwood, et al., "Transcriptional Dynamics of Endodermal Organ Formation," Developmental Dynamics, Jan. 2009, vol. 238, Issue 1, pp. 29-42.

Siller R., et al., "Small-Molecule-Driven Hepatocyte Differentiation of Human Pluripotent Stem Cells", Stem Cell Reports, May 2015, vol. 4, No. 5, pp. 939-952.

Simkin J.E., et al., "Retinoic Acid Upregulates Ret and Induces Chain Migration and Population Expansion in Vagal Neural Crest Cells to Colonise the Embryonic Gut,"PLoS ONE, May 2013, vol. 8(5), e64077, pp. 1-12.

Takebe T., et al., "Generation of a Vasularized and Functional Human Liver from an iPSC-derived Organ Bud Transplant," Nature Protocols, Feb. 2014, vol. 9, Issue 2, pp. 396-409.

Vu, et al., "Regulation of Appetite, Body Composition and Metabolic Hormones by Vasoactive Intestinal Polypeptide (VIP)", Journal of Molecular Neuroscience, Apr. 23, 2015, vol. 56, No. 2, pp. 377-387.

Yamaguchi Y., et al., "Purified Interleukin 5 Supports the Terminal Differentiation and Proliferation of Murine Eosinophilic Precursors," Journal of Experimental Medicine, Jan. 1988, vol. 167, pp. 43-56.

Zhang, et al., "The Existence of Epithelial-to-Mesenchymal Cells with the Ability to Support Hematopoiesis in Human Fetal Liver," Cell Biology International, Mar. 2005, vol. 29, No. 3, pp. 213-219.

\* cited by examiner

METHODS FOR THE IN VITRO MANUFACTURE OF GASTRIC FUNDUS TISSUE AND COMPOSITIONS RELATED TO SAME

CROSS REFERENCE TO RELATED APPLICATIONS

This application claims priority to and benefit of International Application No. PCT/US2017/031309, entitled "Methods for the In Vitro Manufacture of Gastric Fundus Tissue and Compositions Related to Same," filed May 5, 2017, which claims the benefit of and priority to U.S. Provisional Patent Application 62/332,194, filed May 5, 2016, the contents of which are incorporated by reference in their entirety.

GOVERNMENT SUPPORT CLAUSE

This invention was made with government support under AI116491 and DK092456 awarded by the National Institutes of Health. The government has certain rights in the invention.

BACKGROUND

Despite the global prevalence of gastric disease, there are few adequate models to study the fundus epithelium of the human stomach. The development of human fundic-type gastric organoids (hFGOs) would be a novel and powerful model system to study the molecular basis of human gastric physiology, pathophysiology, and drug discovery.

BRIEF SUMMARY

The instant disclosure relates to methods for converting mammalian definitive endoderm (DE) cells into specific tissue(s) or organ(s) through directed differentiation. In particular, the disclosure relates to formation of gastric fundus tissue and/or organoids formed from differentiated definitive endoderm.

BRIEF DESCRIPTION OF THE DRAWINGS

Those of skill in the art will understand that the drawings, described below, are for illustrative purposes only. The drawings are not intended to limit the scope of the present teachings in any way.

Figure 1:
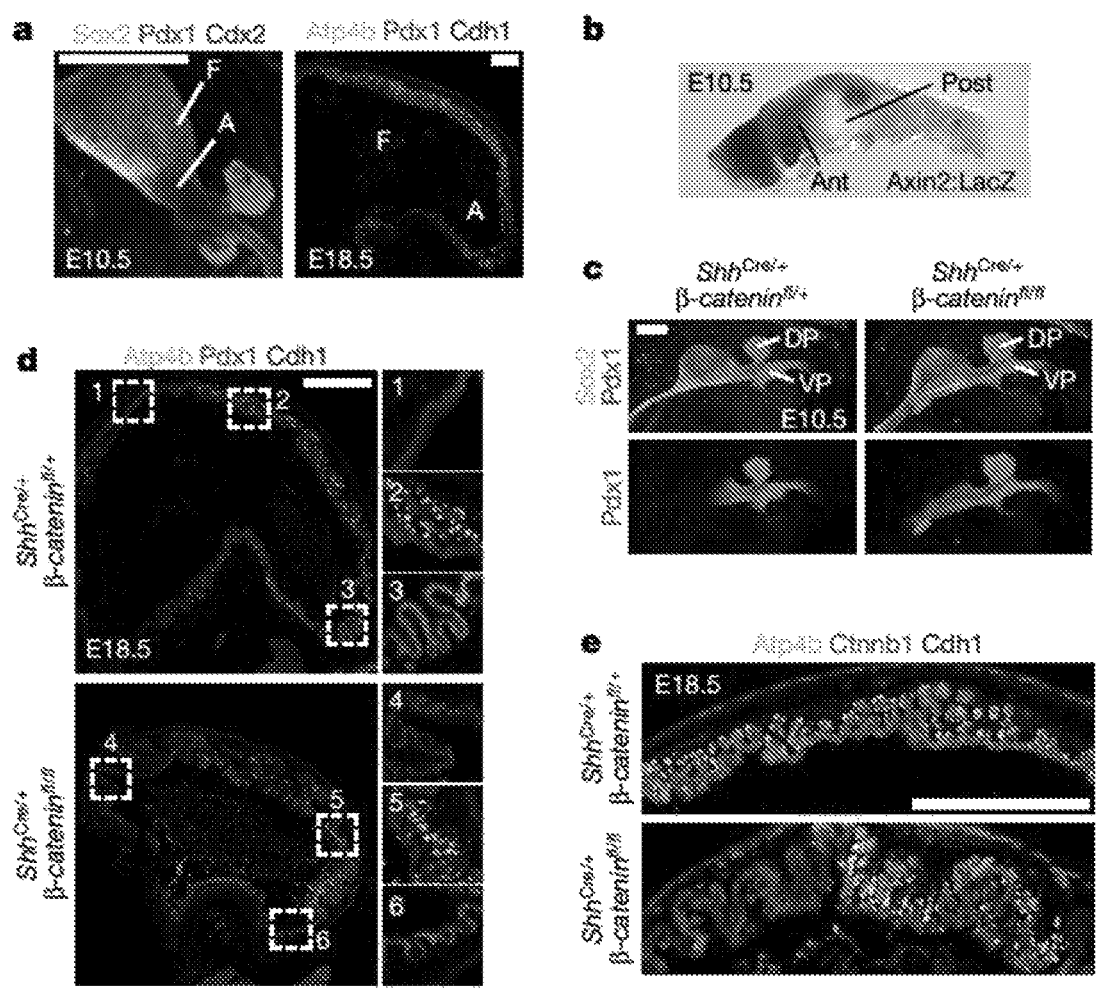
FIG. 1. Wnt/β-catenin signaling is required for specification of the embryonic fundus in mice. a, Pdx1 and Sox2 were expressed in the antrum (a), whereas Pdx1 was absent in the fundus (f), identified by Atp4b-expressing parietal cells at E18.5. b, X-gal staining of an E10.5 foregut from an Axin2:LacZ reporter embryo showed that Wnt activity was restricted to the anterior domain of the stomach but excluded from the posterior stomach. c, Deletion of β-catenin in the gastric epithelium caused an anterior expansion of Pdx1 into the fundic region of the stomach. d, In E18.5 Shh$^{Cre/+}$β-catenin$^{fl/fl}$ (cKO) embryos, Pdx1 was expressed throughout the stomach, except in some remaining patches of parietal cell-containing epithelium. Insets 1a-c and 2a-c show boxed regions in control and cKO stomach, respectively. e, In the cKO stomach, Ctnnb1 exhibited mosaic deletion, and parietal cells only differentiated in Ctnnb1-sufficient epithelium. Scale bars, 250 µm (a), 200 µm (c), and 500 µm (d and e).

Further, differentiation of parietal cells could not be induced through MEK inhibition as they could prior to passaging. Error bars represent s.d.

DETAILED DESCRIPTION OF THE INVENTION

Unless otherwise noted, terms are to be understood according to conventional usage by those of ordinary skill in the relevant art.

As used herein, the term "gastric fundus tissue" means a fundic type of gastric epithelium found in the corpus that contains fundic cell types, including but not limited to acid-producing parietal cells and protease-producing chief cells.

As used herein, the term "definitive endoderm (DE) cell" means one of the three primary germ layers produced by the process of gastrulation.

As used herein the term "wnt signalling pathway" means the wnt/beta-catenin pathway and is a signal transduction pathway that is mediated by Wnt ligands and frizzled cell surface receptors that acts through the beta-catenin protein.

As used herein the term "activator" with respect to a pathway, such as a "wnt pathway" means a substance that activates the Wnt/beta-catenin pathway such that Wnt/beta-catenin targets are increased.

As used herein, the term "FGF signaling pathway activator" means a substance that activates the FGF pathway such that FGF targets are increased.

As used herein, the term "BMP signalling pathway inhibitor" a substance that interferes with the BMP pathway and causes BMP targets to be decreased.

As used herein, the term "growth factor" means a substance capable of stimulating cellular processes including but not limited to growth, proliferation, morphogenesis or differentiation.

As used herein, the term "fundic lineage" means cell types found in fundic epithelium in the corpus stomach.

As used herein, the term "SOX2+GATA+PDX1− epithelium" means epithelium that expresses the listed proteins.

As used herein, the term "stable expression" of a marker means expression that does not change upon modification of the growth environment.

As used herein, the term "totipotent stem cells" (also known as omnipotent stem cells) are stem cells that can differentiate into embryonic and extra-embryonic cell types. Such cells can construct a complete, viable, organism. These cells are produced from the fusion of an egg and sperm cell. Cells produced by the first few divisions of the fertilized egg are also totipotent.

As used herein, the term "pluripotent stem cells (PSCs)," also commonly known as PS cells, encompasses any cells that can differentiate into nearly all cells, i.e., cells derived from any of the three germ layers (germinal epithelium), including endoderm (interior stomach lining, gastrointestinal tract, the lungs), mesoderm (muscle, bone, blood, urogenital), and ectoderm (epidermal tissues and nervous system). PSCs can be the descendants of totipotent cells, derived from embryos (including embryonic germ cells) or obtained through induction of a non-pluripotent cell, such as an adult somatic cell, by forcing the expression of certain genes.

As used herein, the term "induced pluripotent stem cells (iPSCs)," also commonly abbreviated as iPS cells, refers to a type of pluripotent stem cells artificially derived from a normally non-pluripotent cell, such as an adult somatic cell, by inducing a "forced" expression of certain genes.

As used herein, the term "precursor cell" encompasses any cells that can be used in methods described herein, through which one or more precursor cells acquire the ability to renew itself or differentiate into one or more specialized cell types. In some embodiments, a precursor cell is pluripotent or has the capacity to becoming pluripotent. In some embodiments, the precursor cells are subjected to the treatment of external factors (e.g., growth factors) to acquire pluripotency. In some embodiments, a precursor cell can be a totipotent stem cell; a pluripotent stem cell (induced or non-induced); a multipotent stem cell; and a unipotent stem cell. In some embodiments, a precursor cell can be from an embryo, an infant, a child, or an adult. In some embodiments, a precursor cell can be a somatic cell subject to treatment such that pluripotency is conferred via genetic manipulation or protein/peptide treatment.

In developmental biology, cellular differentiation is the process by which a less specialized cell becomes a more specialized cell type. As used herein, the term "directed differentiation" describes a process through which a less specialized cell becomes a particular specialized target cell type. The particularity of the specialized target cell type can be determined by any applicable methods that can be used to define or alter the destiny of the initial cell. Exemplary methods include but are not limited to genetic manipulation, chemical treatment, protein treatment, and nucleic acid treatment.

As used herein, the term "cellular constituents" are individual genes, proteins, mRNA expressing genes, and/or any other variable cellular component or protein activities such as the degree of protein modification (e.g., phosphorylation), for example, that is typically measured in biological experiments (e.g., by microarray or immunohistochemistry) by those skilled in the art. Significant discoveries relating to the complex networks of biochemical processes underlying living systems, common human diseases, and gene discovery and structure determination can now be attributed to the application of cellular constituent abundance data as part of the research process. Cellular constituent abundance data can help to identify biomarkers, discriminate disease subtypes and identify mechanisms of toxicity.

Pluripotent Stem Cells Derived from Embryonic Cells

In some embodiments, an important step is to obtain stem cells that are pluripotent or can be induced to become pluripotent. In some embodiments, pluripotent stem cells are derived from embryonic stem cells, which are in turn derived from totipotent cells of the early mammalian embryo and are capable of unlimited, undifferentiated proliferation in vitro. Embryonic stem cells are pluripotent stem cells derived from the inner cell mass of the blastocyst, an early-stage embryo. Methods for deriving embryonic stem cells from blastocytes are well known in the art. Human embryonic stem cells H9 (H9-hESCs) are used in the exemplary embodiments described in the present application, but it would be understood by one of skill in the art that the methods and systems described herein are applicable to any stem cells.

Additional stem cells that can be used in embodiments in accordance with the present invention include but are not limited to those provided by or described in the database hosted by the National Stem Cell Bank (NSCB), Human Embryonic Stem Cell Research Center at the University of California, San Francisco (UCSF); WISC cell Bank at the Wi Cell Research Institute; the University of Wisconsin Stem Cell and Regenerative Medicine Center (UW-SCRMC); Novocell, Inc. (San Diego, Calif.); Cellartis AB (Goteborg, Sweden); ES Cell International Pte Ltd (Singapore); Technion at the Israel Institute of Technology (Haifa, Israel); and the Stem Cell Database hosted by Princeton University and the University of Pennsylvania. Exemplary embryonic stem cells that can be used in embodiments in accordance with the present invention include but are not limited to SA01 (SA001); SA02 (SA002); ES01 (HES-1); ES02 (HES-2); ES03 (HES-3); ES04 (HES-4); ES05 (HES-5); ES06 (HES-6); BG01 (BGN-01); BG02 (BGN-02); BG03 (BGN-03); TE03 (13); TE04 (14); TE06 (16); UC01 (HSF1); UC06 (HSF6); WA01 (H1); WA07 (H7); WA09 (H9); WA13 (H13); WA14 (H14).

More details on embryonic stem cells can be found in, for example, Thomson et al., 1998, "Embryonic Stem Cell Lines Derived from Human Blastocysts," Science 282 (5391):1145-1147; Andrews et al., 2005, "Embryonic stem (ES) cells and embryonal carcinoma (EC) cells: opposite sides of the same coin," Biochem Soc Trans 33:1526-1530; Martin 1980, "Teratocarcinomas and mammalian embryogenesis,". Science 209 (4458):768-776; Evans and Kaufman, 1981, "Establishment in culture of pluripotent cells from mouse embryos," Nature 292(5819): 154-156; Klimanskaya et al., 2005, "Human embryonic stem cells derived without feeder cells," Lancet 365 (9471): 1636-1641; each of which is hereby incorporated herein in its entirety.

Induced Pluripotent Stem Cells (iPSCs)

In some embodiments, iPSCs are derived by transfection of certain stem cell-associated genes into non-pluripotent cells, such as adult fibroblasts. Transfection is typically achieved through viral vectors, such as retroviruses. Transfected genes include the master transcriptional regulators Oct-3/4 (Pouf51) and Sox2, although it is suggested that other genes enhance the efficiency of induction. After 3-4 weeks, small numbers of transfected cells begin to become morphologically and biochemically similar to pluripotent stem cells, and are typically isolated through morphological selection, doubling time, or through a reporter gene and antibiotic selection. As used herein, iPSCs include but are not limited to first generation iPSCs, second generation iPSCs in mice, and human induced pluripotent stem cells. In some embodiments, a retroviral system is used to transform human fibroblasts intopluripotent stem cells using four pivotal genes: Oct3/4, Sox2, Klf4, and c-Myc. In alternative embodiments, a lentiviral system is used to transform somatic cells with OCT4, SOX2, NANOG, and LIN28. Genes whose expression are induced in iPSCs include but are not limited to Oct-3/4 (e.g., Pou5fl); certain members of the Sox gene family (e.g., Sox1, Sox2, Sox3, and Sox15); certain members of the Klf family (e.g., Klf1, Klf2, Klf4, and Klf5), certain members of the Myc family (e.g., C-myc, L-myc, and N-myc), Nanog, and LIN28.

In some embodiments, non-viral based technologies are employed to generate iPSCs. In some embodiments, an adenovirus can be used to transport the requisite four genes into the DNA of skin and liver cells of mice, resulting in cells identical to embryonic stem cells. Since the adenovirus does not combine any of its own genes with the targeted host, the danger of creating tumors is eliminated. In some embodiments, reprogramming can be accomplished via plasmid without any virus transfection system at all, although at very low efficiencies. In other embodiments, direct delivery of proteins is used to generate iPSCs, thus eliminating the need for viruses or genetic modification. In some embodiment, generation of mouse iPSCs is possible using a similar methodology: a repeated treatment of the cells with certain proteins channeled into the cells via poly-arginine anchors was sufficient to induce pluripotency. In some embodiments, the expression of pluripotency induction genes can also be increased by treating somatic cells with FGF2 under low oxygen conditions.

More details on embryonic stem cells can be found in, for example, Kaji et al., 2009, "Virus free induction of pluripotency and subsequent excision of reprogramming factors," Nature 458:771-775; Woltj en et al., 2009, "piggyBac transposition reprograms fibroblasts to induced pluripotent stem cells," Nature 458:766-770; Okita et al., 2008, "Generation of Mouse Induced Pluripotent Stem Cells Without Viral Vectors," Science 322(5903):949-953; Stadtfeld et al., 2008, "Induced Pluripotent Stem Cells Generated without Viral Integration," Science 322(5903):945-949; and Zhou et al., 2009, "Generation of Induced Pluripotent Stem Cells Using Recombinant Proteins," Cell Stem Cell 4(5):381-384; each of which is hereby incorporated herein in its entirety.

In some embodiments, exemplary iPS cell lines include but not limited to iPS-DF19-9; iPS-DF19-9; iPS-DF4-3; iPS-DF6-9; iPS(Foreskin); iPS(IMR90); and iPS(IMR90).

More details on the functions of signaling pathways relating to DE development can be found in, for example, Zorn and Wells, 2009, "Vertebrate endoderm development and organ formation," Annu Rev Cell Dev Biol 25:221-251; Dessimoz et al., 2006, "FGF signaling is necessary for establishing gut tube domains along the anterior-posterior axis in vivo," Mech Dev 123:42-55; McLin et al., 2007, "Repression of Wnt/β-catenin signaling in the anterior endoderm is essential for liver and pancreas development. Development," 134:2207-2217; Wells and Melton, 2000, Development 127:1563-1572; de Santa Barbara et al., 2003, "Development and differentiation of the intestinal epithelium," Cell Mol Life Sci 60(7): 1322-1332; each of which is hereby incorporated herein in its entirety.

Any methods for producing definitive endoderm from pluripotent cells (e.g., iPSCs or ESCs) are applicable to the methods described herein. In some embodiments, pluripotent cells are derived from a morula. In some embodiments, pluripotent stem cells are stem cells. Stem cells used in these methods can include, but are not limited to, embryonic stem cells. Embryonic stem cells can be derived from the embryonic inner cell mass or from the embryonic gonadal ridges. Embryonic stem cells or germ cells can originate from a variety of animal species including, but not limited to, various mammalian species including humans. In some embodiments, human embryonic stem cells are used to produce definitive endoderm. In some embodiments, human embryonic germ cells are used to produce definitive endoderm. In some embodiments, iPSCs are used to produce definitive endoderm.

Disclosed herein are methods for differentiating human pluripotent stem cells (PSCs) into gastric organoids containing fundic epithelium. Applicant first identified, and then recapitulated key events in embryonic fundus development to arrive at the claimed compositions. Applicant found that disruption of Wnt/β-catenin signaling in mouse embryos led to conversion of fundic to antral epithelium, while β-catenin activation in hPSC-derived foregut progenitors promoted the development of human fundic-type gastric organoids (hFGOs). Applicant then used hFGOs to identify temporally distinct roles for multiple signaling pathways in epithelial morphogenesis and differentiation of fundic cell types, including chief cells and functional parietal cells. While hFGOs are a powerful new model for studying the development of the human fundus and its lineages, they also represent a critical new model system to study the molecular basis of human gastric physiology, pathophysiology, and drug discovery.

In one aspect, an in vitro method of inducing formation of a gastric fundus tissue is disclosed. The method may comprise the steps of:

a) contacting a mammalian definitive endoderm (DE) cell with a wnt pathway activator, an FGF signaling pathway activator (for example, FGF4), a BMP signalling pathway inhibitor (e.g., Noggin), and retinoic acid, for a first period. Wnt signalling may be activated either with a protein like Wnt3a, for example, or via a chemical like Chiron, for example, which inhibits GSK3β. The first period may be three days±24 hours. The retinoic acid may be added for the third day of the first period±24 hours. In one aspect, the first period may be carried out for a period of time sufficient to form a three-dimensional posterior foregut spheroid from the definitive endoderm.

b) suspending said three-dimensional posterior foregut spheroid in a basement membrane matrix with a growth factor, a Wnt signalling pathway activator, a EGF signalling pathway activator, a BMP signalling pathway inhibitor, and retinoic acid for a second period. The second period may be three days±24 hours. The second period may be carried out for a period of time sufficient to induce a fundic lineage comprising fundal hGOs (hFGOs).

c) culturing the hFGOs of step b) with a wnt pathway activator and a EGF signalling pathway activator for a third period. The third period may be, for example, 11 days±24 hours.

d) culturing the hFGOs of step c with a wnt signaling pathway activator, a EGF signalling pathway activator, and FGF10 for a fourth period. The fourth period may be, for example, 10 days±24 hours.

e) contacting said hFGOs of step d with a MEK inhibitor for a fifth period. The MEK inhibitor may be, for example, PD0325901. The fifth period may be for a two-day period±24 hours, or for a period of time sufficient to form a gastric fundus tissue comprising a functional fundic cell type.

In one aspect, step e) may further comprise the step of contacting the fundal hGOs with an activator of BMP4 signalling. In certain aspects, step e may be carried out for a period of time sufficient to develop SOX2+GATA+PDX1− epithelium.

In one aspect, the functional fundic cell type may be a parietal cell that expresses proton pump proteins and secretes acid. In one aspect, the functional fundic cell type may be a chief cell that secretes pepsinogen.

In one aspect, step d and step e are carried out for a period of time sufficient to confer stable expression of lineage markers MUC5AC, MUC6, PGC, and GHRL.

In one aspect, the definitive endoderm may be derived from a precursor cell selected from an embryonic stem cell, an embryonic germ cell, an induced pluripotent stem cell, a mesoderm cell, a definitive endoderm cell, a posterior endoderm cell, a posterior endoderm cell, and a hindgut cell, a definitive endoderm derived from a pluripotent stem cell, a definitive endoderm derived from a pluripotent stem cell selected from an embryonic stem cell, an adult stem cell, or an induced pluripotent stem cell.

In one aspect, the definitive endoderm may be derived from contacting a pluripotent stem cell with one or more molecules selected from Activin, the BMP subgroups of the TGF-beta superfamily of growth factors; Nodal, Activin A, Activin B, BMP4, Wnt3a, and combinations thereof.

There are many ways to activate the Wnt/beta-catenin pathway (see http://web.stanford.edu/group/nusselab/cgi-bin/wnt/). Suitable Some existing wnt signalling pathway activators include but are not limited to:

Protein-based activators: Wnt ligands including but not limited to Wnt1, Wnt2, Wnt2b, Wnt3, Wnt3a, Wnt8, et al; modifiers of Wnt ligand activity including but not limited to activated Wnt frizzled receptors, (LRP) co-receptors, R-spondin proteins, Dkk proteins, regulators of Wnt ligand secretion and trafficking (Wntless, Porcupine), inhibiting beta-catenin degredation APC and GSK3beta inhibition, activated beta-catenin, constitutively active TCF/Lef proteins.

Chemical activators: there are over 28 known chemicals that either activate or inhibit Wnt/beta-catenin signaling. Some activators include but are not limited to GSK3-beta inhibitors CHIR99021, BIO, LY2090314, SB-216763, lithium, porcupine inhibitors IWP, LGK974, C59, SFRP inhibitor WAY-316606, beta-catenin activator DCA.

In one aspect, the WNT pathway activator may be one or more molecules selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16, for example, Wnt3a, or for example, Wnt3a at a concentration between about 50 to about 1500 ng/ml.

Suitable FGF signalling pathway activators include: FGF ligands FGF2, 4, 5, 8, et al. Activated forms of FGF receptors. Proteins and chemicals that stimulate the FGF receptor and signaling components downstream of the receptors including MAPK, MEK, ERK proteins and chemicals that modulate their activity. FGF signaling can be activated by inhibiting inhibitors of FGF signaling pathways including but not limited to Sprouty protein family members.

In one aspect, the BMP signalling pathway inhibitor may be selected from Noggin, Dorsomorphin, LDN189, DMH-1, and combinations thereof, for example, wherein said precursor cell may be contacted with a BMP inhibitor at a concentration between about 50 to about 1500 ng/ml.

In one aspect, the steps are conducted in vitro.

In one aspect, a composition comprising gastric tissue produced according to the aforementioned method(s) is disclosed. The gastric tissue may be characterized, for example, by being free of innervation and/or blood vessels.

In one aspect, an in vitro method of inducing formation of a gastric fundus tissue is disclosed. The method may comprise the steps of contacting a fundal hGO (hFGO) with a wnt pathway activating agent and an EGF signalling pathway activating agent for a first period, and a MEK inhibitor for a second period, (wherein said MEK inhibitor may be PD0325901), wherein said first and second periods are carried out for a period of time sufficient to form a functional fundic cell type;

wherein said hFGO are obtained by contacting a three-dimensional posterior foregut spheroid in a basement membrane matrix with a growth factor, a wnt pathway activating agent, an EGF signalling pathway activator, a BMP signalling pathway inhibitor, and retinoic acid for a period of time sufficient to convert said three-dimensional posterior foregut spheroid to said hFGO;

wherein said three-dimensional posterior foregut spheroids are obtained by contacting a mammalian definitive endoderm (DE) cells with a wnt pathway activating agent, an FGF signaling pathway activating agent, a BMP signalling pathway inhibitor, and retinoic acid.

EXAMPLES

Recently, considerable progress has been made in the development of three-dimensional in vitro organoid systems[1,2]. Organoids have proven to be powerful experimental models that combine architectural complexity and cellular diversity with the tractability and scalability of traditional cell culture methods. Organoid generation through directed differentiation of pluripotent stem cells (PSCs; comprising both embryonic stem cells and induced PSCs) offers several advantages over other approaches including an unlimited source of starting material, no requirement for surgical acquisition of tissue, and ease of genetic manipulations. Further, PSC-based methods permit direct investigation of mechanisms underlying normal and aberrant human development[3]. However, differentiating PSCs into specific organoid types depends on a robust molecular knowledge of normal organ development. For some organs, such as the stomach, there are large gaps in understanding of molecular pathways that drive embryonic development.

The stomach is one of the most structurally diverse organs among mammals[4]. In humans, the gastric mucosa generally consists of two types of epithelial glands[5,6]. Located in the more proximal anatomic domains—the corpus and fundus— of the stomach, oxyntic glands comprise acid-secreting parietal cells, protease-producing chief cells, mucus-producing cells, and endocrine cells. Antral-type glands, located in the more distal antrum and pylorus, contain mostly mucous and endocrine cells. To simplify the anatomic- and species-specific systems of nomenclature, the terms 'fundus' and 'antrum' are used to broadly describe these two histologic types of gastric epithelia. Applicant has previously developed a method to direct the differentiation of hPSCs into three-dimensional gastric tissue (human gastric organoids; hGOs) that contained a pure antral epithelium with normal antral cell types[7]. While the antral hGOs (hAGOs) are a robust system for studying antral lineage allocation and host-microbe interactions in the stomach, they do not allow for studies of fundic biology and disease. More recently, Noguchi et. al. successfully differentiated mouse ESCs into organoids comprising various types of mouse gastric tissue[8]. However, this approach used mouse ESC aggregation and spontaneous differentiation resulting in organoids that were heterogeneous, evidenced by the presence of stratified epithelia. Moreover, species differences make the mouse stomach suboptimal for modeling human gastric disease[9]. Thus, a robust and efficient PSC-derived model of the human fundus epithelium would represent a significant advance in the field of gastric biology.

Embryonic organ development is guided by a series of instructive cues between neighboring tissues[10,11], and differentiation of hPSCs into specific lineages has relied heavily on use of these signals to direct differentiation in vitro. Applicant previously identified a step-wise differentiation approach to generate hAGOs, whereby hPSCs were differentiated into definitive endoderm, patterned to posterior foregut, then specified into presumptive antral epithelium[7]. Applicant hypothesized that the fundus and antrum derive from a common population of posterior foregut progenitors, which could be directed toward the fundic lineage if provided with the appropriate signals. However, given that the mechanisms that drive fundus development in vivo were not previously known, Applicant first had to identify signaling pathways that pattern the embryonic stomach along the proximal-distal axis.

Embryonic Stomach Pattern Formation

To aid investigation of the pathways that regulate fundus specification during embryonic development, Applicant analyzed mouse embryos to identify molecular markers that could distinguish between presumptive fundus, antrum and forestomach. At E14.5 Applicant found that Sox2 was expressed in all foregut organ lineages while Gata4 was restricted to the glandular stomach epithelium. Within the Gata4+ domain, Pdx1 was specific to the presumptive antral region (FIG. 6, *a*); thus, the embryonic fundus domain is believed to be Sox2+Gata+Pdx1−. Further, Applicant analyzed published microarray datasets (GSM326648-GSM32665012 and GSM80809-GMS8081613) and dissected regions of the E14.5 foregut to demonstrate that expression of the transcription factors Irx2, Irx3, and Irx5 was greater than ten-fold enriched in the embryonic fundus compared to antrum (FIG. 6, *b-c*), indicating that their expression can further distinguish between regions of the glandular gastric epithelium.

Figure 6:
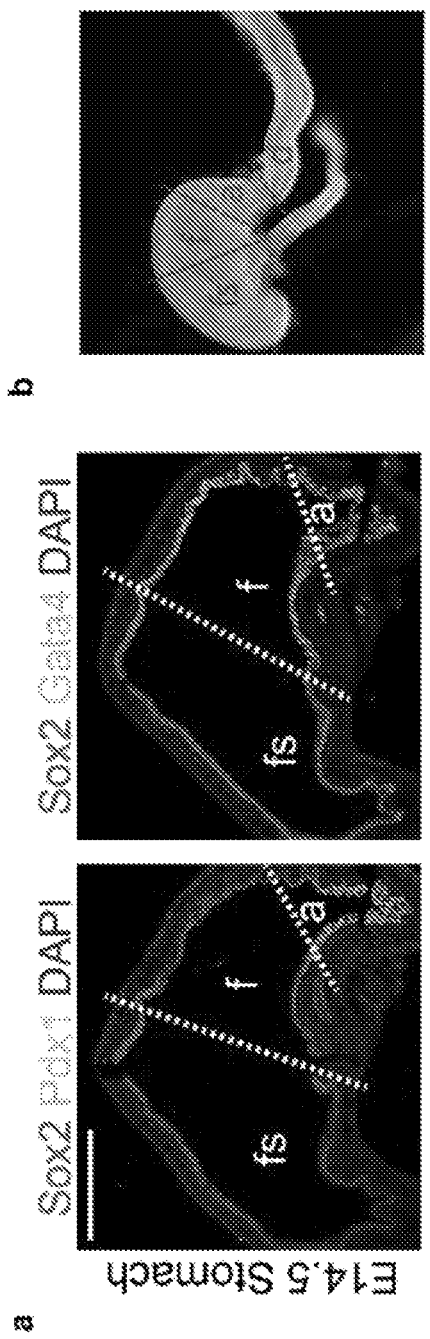
FIG. 6. Defining molecular domains in the developing stomach in vivo. a, Analysis of Sox2, Pdx1, and Gata4 in the embryonic mouse stomach (E14.5) showed that the fundus (f) was Sox2+Gata4+Pdx1−, whereas the antrum (a) was Sox2+Gata4+Pdx1+. The forestomach (fs) expressed Sox2 but neither Gata4 nor Pdx1. b, Brightfield stereomicrograph showing dissected regions of the E14.5 mouse stomach that were analyzed by qPCR. fs, forestomach; f, fundus; a, antrum; d, duodenum. c, Dissected regions in b were analyzed by qPCR for known regionally expressed markers (Sox2, P63, Gata4, Pdx1, and Cdx2) to validate the accuracy of micro-dissection. qPCR analysis of the dissected E14.5 stomach regions showed that putative fundus markers Irx1, Irx2, Irx3, Irx5, and Pitx1 were enriched in the fundus compared to the antrum. n=4 biological replicates per dissected region. Scale bar, 500 µm. Error bars represent s.d.
Figure 6:
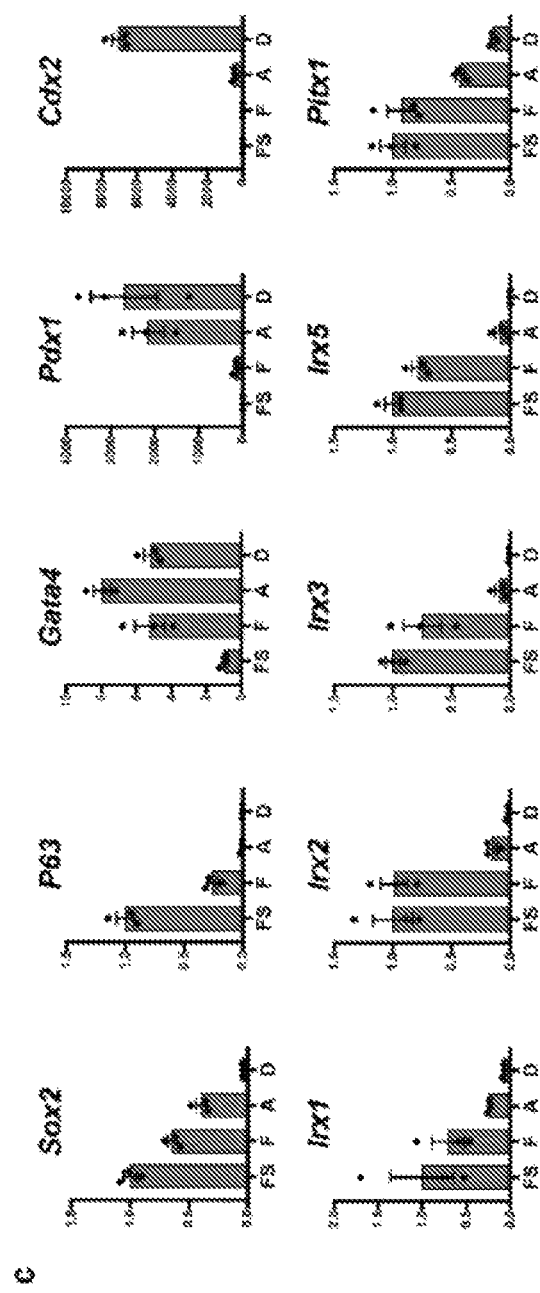
Figure 7:
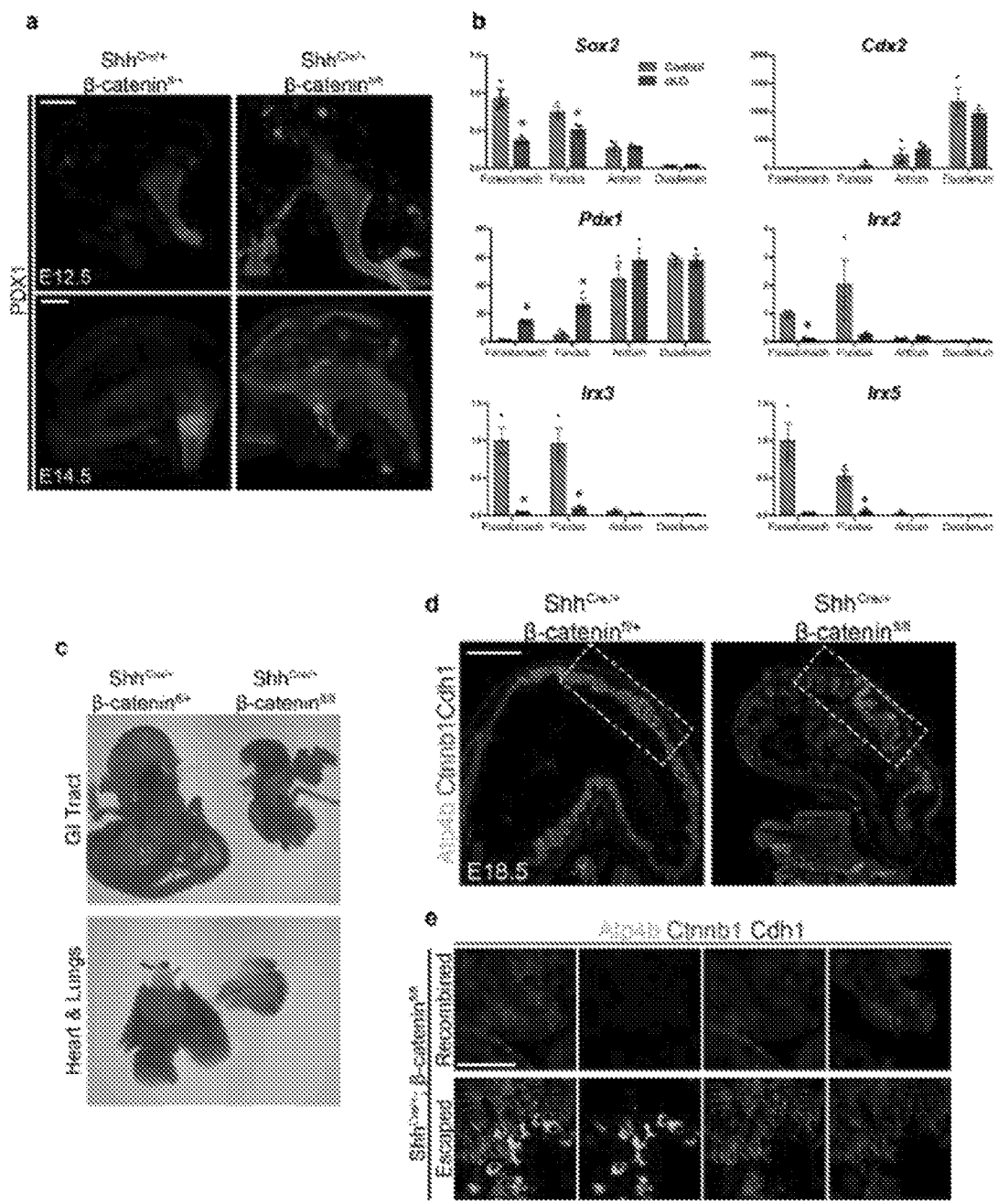
FIG. 7. Analysis of β-catenin cKO embryos. a, By E12.4 and E14.5, ectopic Pdx1 expression was observed throughout the dorsal gastric epithelium, as well as the most proximal gastric epithelium of the cKO embryo. b, qPCR analysis of dissected regions (FIG. 6, b) of E14.5 cKO foregut showed significant up-regulation of Pdx1 in the fundus and forestomach domains. Conversely, Irx2, Irx3, and Irx5 were markedly reduced in these proximal regions. *, p<0.05; two tailed Student's t-test n=3 biological replicates per dissected region for each genotype. c, Stereomicrographs of E18.5 dissected viscera demonstrated that cKO embryos exhibited lung agenesis as previously reported. The GI tract, particularly the stomach, was dramatically reduced in size. d, Immunofluorescent staining at E18.5 revealed mosaic deletion pattern of Ctnnb1. Boxed regions are shown in FIG. 1, e, In the E18.5 cKO stomach, recombined glands lacking Ctnnb1 staining did not contain parietal cells whereas robust parietal cell differentiation was observed in Ctnnb1-positive glands. Scale bars, 200 µm (a), 500 µm (d), and 50 µm (e). Error bars represent s.d.

At the molecular level, the presumptive fundic and antral domains of the stomach were already established by E10.5 (FIG. 6, *a*). At that point in development, the canonical Wnt signaling pathway was active in the proximal stomach but exhibited little or no activity in the distal stomach[14], as shown using the Wnt reporter mouse strain Axin2-lacZ (FIG. 1*b*). While the regulation of Wnt/β-catenin signaling is known to play a role in establishing the pyloric-duodenal boundary[14,15], its role in gastric epithelial patterning had not been investigated. To determine whether Wnt/β-catenin signaling was functionally required for establishing the fundus in vivo, Applicant deleted β-catenin (Ctnnb1) in the foregut epithelium using Shh-cre (Shh-cre;β-cateninfl/fl=cKO). Disruption of Wnt/β-catenin signaling resulted in the loss of fundic identity, demonstrated by ectopic Pdx1 expression in the fundus at E10.5 (FIG. 1, *c*). Ectopic Pdx1 was initially restricted to the ventral half of the fundic epithelium, consistent with previously reported recombination activity using this Shh-cre line[16], but it then expanded over time to include a majority of the proximal stomach and greater curvature by E14.5 (FIG. 7, *a*). Additionally, expression of the fundus markers Irx2, Irx3, and Irx5 were dramatically reduced in the cKO embryos (FIG. 7, *b*). Collectively, these data support the conclusion that epithelial Wnt/β-catenin signaling regulates gastric pattern formation, as it is required for the initial specification of fundus identity while repressing antral fate in the embryonic mouse stomach.

To determine the impact of early Wnt/β-catenin-mediated patterning abnormalities on subsequent cytodifferentiation, Applicant analyzed cKO embryos at E18.5. The stomach in cKO embryos was malformed and reduced in size at E18.5 (FIG. 1, *d* and FIG. 7, *c-d*), suggestive of a role for Wnt/β-catenin in promoting stomach growth during late stages of development. Moreover, the cKO stomach was completely mis-patterned with ectopic Pdx1 expression throughout the proximal-most regions of the epithelium (FIG. 1, *d*). Parietal cells, a fundic cell type marked by expression of Atp4b, were reduced in the CKO stomach (FIG. 1, *d*) and completely absent in β-catenin deficient epithelium (FIG. 1, *e*). In contrast, the parietal cells that did develop were only observed in β-catenin-expressing epithelium (FIG. 1, *e* and FIG. 7, *d-e*). Taken together, these in vivo data support a model by which Wnt/β-catenin signaling induces fundus specification and inhibits antral identity. Further, disruption of this early patterning coincides with subsequent cell autonomous loss of parietal cells, suggesting that cytodifferentiation is impaired secondary to developmental patterning defects.

Differentiation of Fundic hGOs from hPSCs

Figure 2:
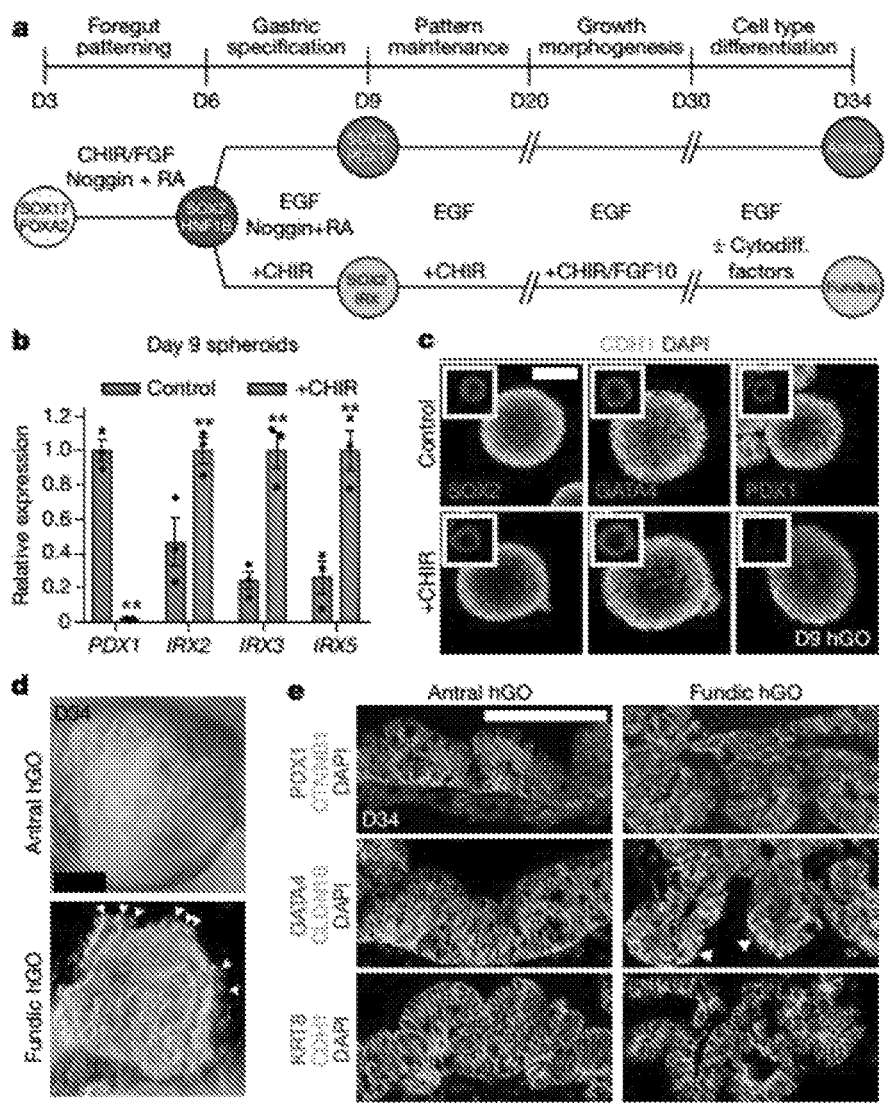
FIG. 2. β-catenin activation promotes fundus development from human foregut progenitor spheroids. a, Schematized diagram of differentiation protocol for both fundic and antral hGOs. b, c, At day 9, CHIR-treated organoids exhibited reduction in PDX1, increase in IRX2, IRX3, and IRX5, and no change in gastric markers SOX2 or GATA4. *, $p<0.05$; two-tailed Student's t-test; n=3 biological replicates, data representative of 4 independent experiments. d, hFGOs grew comparably to hAGOs, but also exhibited glandular budding morphogenesis (white arrowheads). e, Both hGOs contained epithelium that expressed CDH1, KRT8, and CTNNB1, as well as gastric markers GATA4 and CLDN18. hAGOs exhibited nearly ubiquitous PDX1 expression while hFGOs did not. Scale bars, 50 µm (c), 500 µm (d) and 100 µm (e). Error bars represent s.e.m.

Applicant next investigated the role of Wnt/β-catenin signaling in establishing fundic-antral pattern of the developing human stomach. To model early stages of stomach differentiation, Applicant started with a previously described protocol for differentiating hPSCs into antrum-like gastric organoids, which recapitulates the normal stages of early gastric development with high fidelity[7]. Starting with three-dimensional posterior foregut spheroids (SOX2+HNF1β+), Applicant tested whether stimulation of Wnt/β-catenin signaling would direct posterior foregut epithelium into the fundic (SOX2+GATA+PDX1−) lineage rather than antrum (SOX2+GATA+PDX1+) during the gastric specification stage (FIG. 2, *a*). Indeed, activating β-catenin with the GSK3β inhibitor CHIR99021 (CHIR) for three days resulted in nearly complete repression of PDX1 at day 9, accompanied by significantly increased expression of IRX2, IRX3, and IRX5 (FIG. 2, *b-c*). Importantly, SOX2 and GATA4 levels were unaffected by CHIR treatment, confirming that spheroids retained their gastric identity. Thus, CHIR exposure resulted in formation of SOX2+GATA+PDX1− epithelium with increased IRX expression, a signature consistent with the presumptive fundic epithelium.

Figure 8:
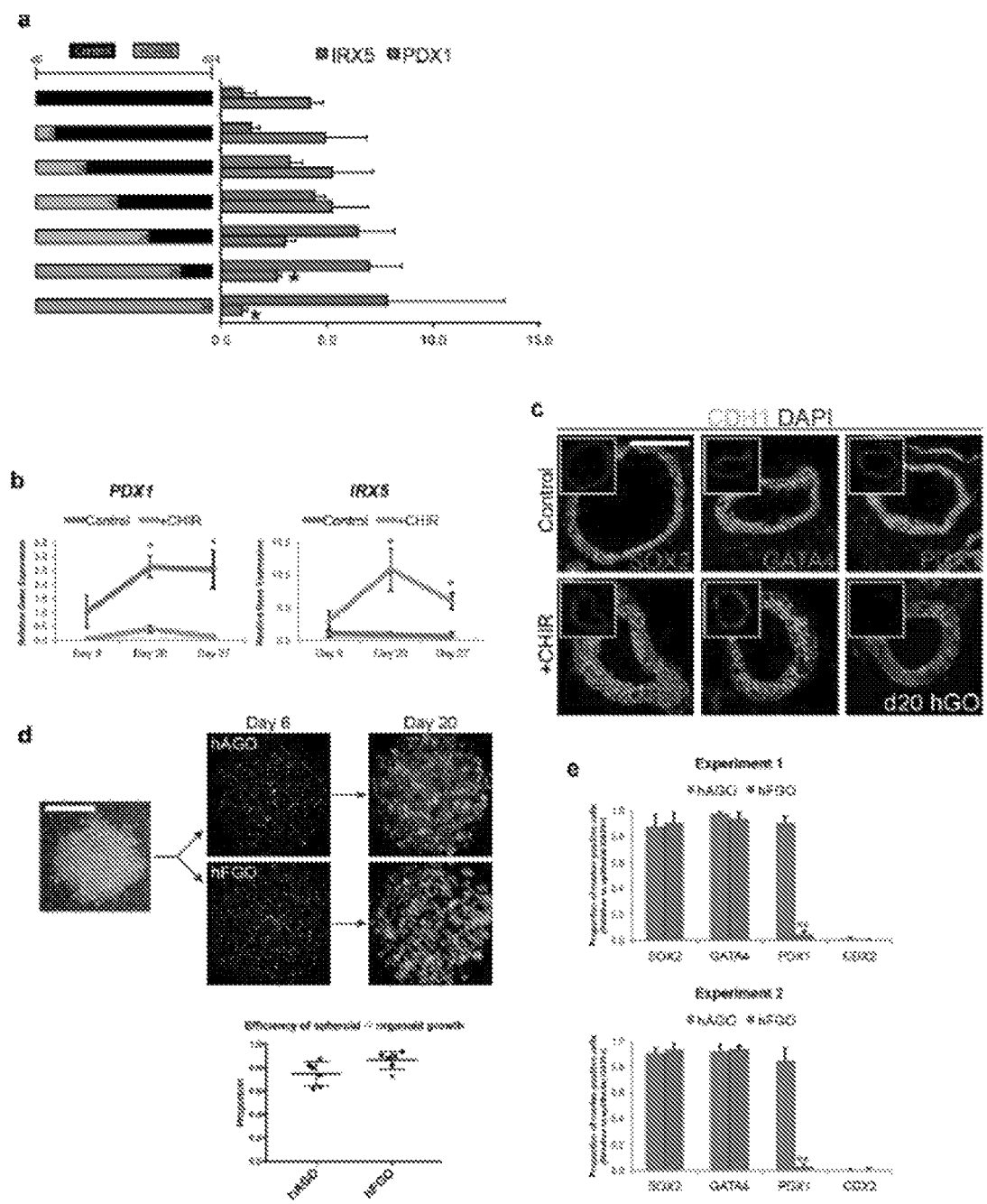
FIG. 8. Stable induction of fundic fate in hGOs and efficiency of protocol. a, Applicant investigated how long CHIR treatment was necessary to establish fundus identity. Brief CHIR treatment (d6-9) and subsequent growth of organoids in control growth medium until day 34 resulted in fundic organoids expressing the antral marker PDX1, suggesting that short CHIR treatment did not produce a stable fundic fate. Applicant then tested whether longer exposures to CHIR were required to retain fundic fate and found that only continuous treatment through at least day 29 could maintain low expression of the antral marker PDX1. *, p<0.05 compared to control antral hGOs; two tailed Student's t-test. n=3 biological replicates, data representative of 2 independent experiments. b, c, Over the course of the protocol, PDX1 remained low in CHIR-treated organoids, while IRX5 expression was persistently elevated. *, p<0.05; two-tailed Student's t-test; n=3 biological replicates per timepoint. d, Conversion of d6 posterior foregut spheroids to early stage gastric organoids (d20) is greater than 80% efficient in both the hAGO and hFGO protocols. e, At d20, hFGO epithelium is ~90% GATA4+/SOX2+/PDX1− whereas hAGO epithelium is ~90% GATA4+/SOX2+/PDX1+. **, p<0.001, two-tailed Student's t-test, n=4 biological replicates per experiment, two individual experiments shown. Scale bars, 100 µm (c) and 200 µm (d).
Figure 9:
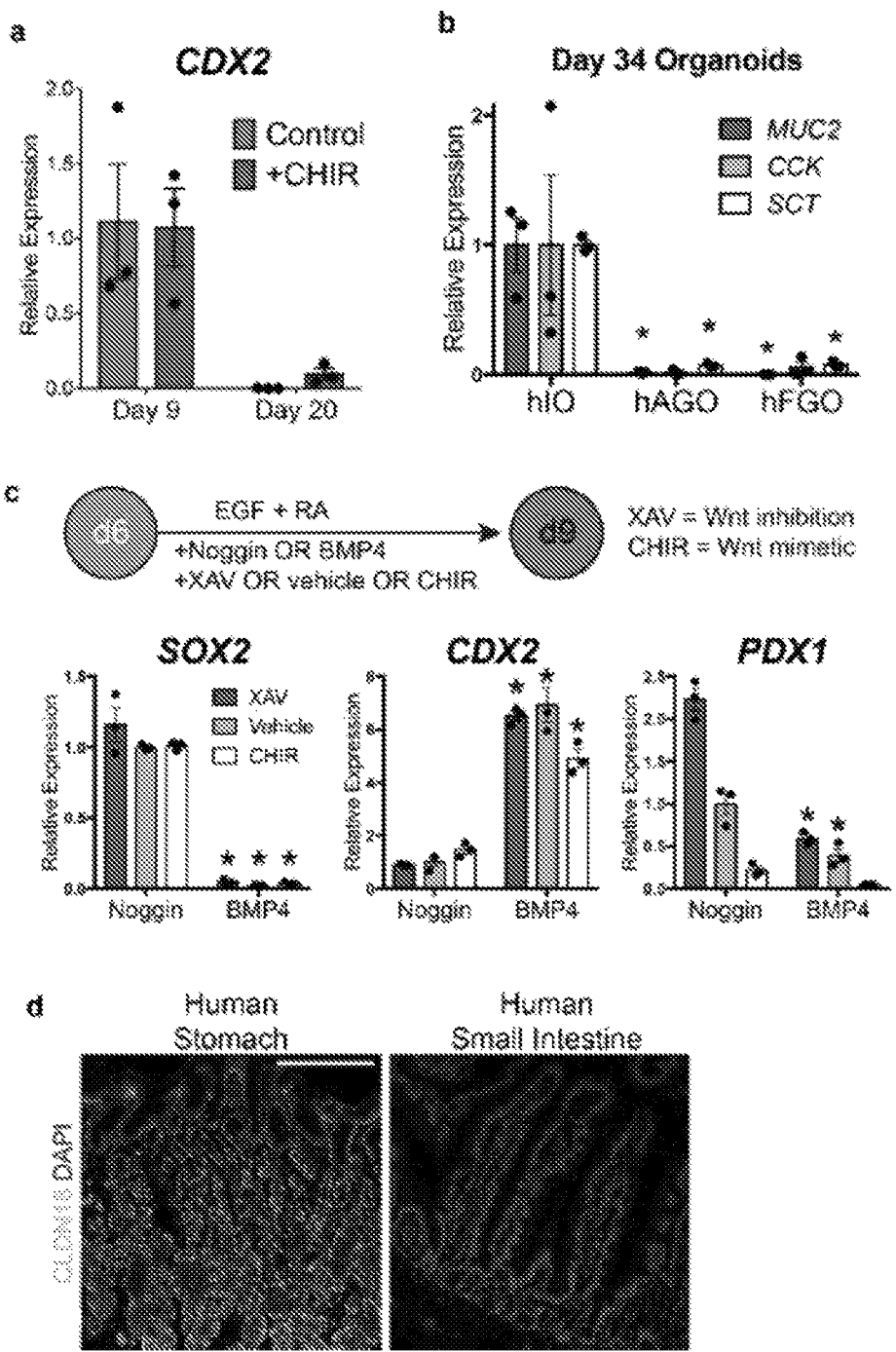
FIG. 9. BMP-dependence of Wnt/β-catenin activation to induce intestinal fate from foregut progenitors. a, The intestine-specific transcription factor CDX2 was not significantly induced in CHIR-treated hGOs at either day 9 or day 20. b, Neither fundic nor antral hGOs expressed genes associated with intestinal cell types, including MUC2, CCK, and SCT, when compared to human intestinal organoids (hIOs). *, p<0.05 compared to hIO; two tailed Student's t-test. n=3 biological replicates. c, Anterior-posterior fate is coordinately controlled by WNT and BMP activity. In the presence of the BMP inhibitor Noggin, all organoids maintained foregut (SOX2+) regardless of Wnt/β-catenin pathway activity; however in the presence of BMP4, all organoids were posteriorized (CDX2+). Activation of Wnt (CHIR) in a BMP inhibited state resulted in fundus pattern (SOX2+, PDX1−, CDX2−) whereas activation of WNT (CHIR) and addition of BMP4 resulted in an intestinal fate (CDX2+). *, p<0.05 compared to analogous Noggin-treated condition; two tailed Student's t-test. n=3 biological replicates. d, Immunofluorescent staining of human tissues revealed that CLDN18 was a gastric-specific epithelial marker that is not found in the intestine. Scale bar, 200 µm. Error bars represent s.e.m.

Applicant then sought to determine whether CHIR-treated spheroids would further develop into more mature hGOs containing a fundus-like epithelium. Interestingly, a three-day pulse of CHIR from days 6-9 was not sufficient to irreversibly specify a fundic identity, as the hGOs ultimately reverted to a PDX1+ antral phenotype at later stages. However, continued Wnt stimulation via CHIR treatment through at least day 29 led to stable induction of fundic gene expression (FIG. 8, a). This was consistent with the prolonged activity of Wnt/β-catenin signaling during embryonic stomach development in vivo. Although previous studies indicated that ectopic Wnt activation in the embryonic stomach promoted intestinal fate[14,15], CHIR-treated hGOs did not exhibit a significant increase in intestinal markers CDX2, MUC2, CCK, or SCT (FIG. 8, *e* and FIG. 9, *a-b*). Applicant further demonstrated that CDX2 remained suppressed despite Wnt/β-catenin activation due to concomitant inhibition of BMP signaling, as replacing Noggin with BMP4 led to robust expression of the intestinal transcription factor (FIG. 9, *c*).

Figure 10:
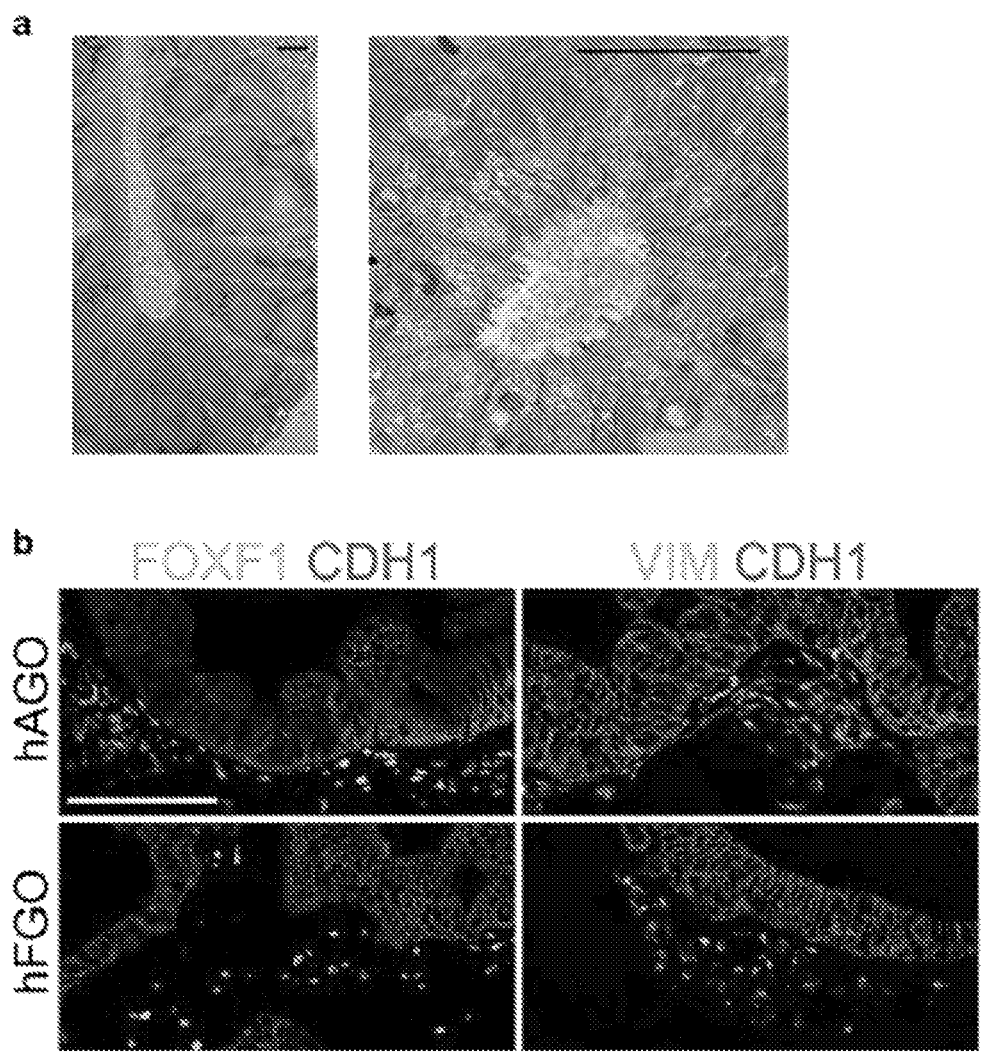
FIG. 10. hFGOs contain organized glands supported by associated mesenchymal layer. a, Transmission electron micrographs demonstrated that hFGO glands exhibited organized architecture with narrow apical membranes. b, Both hFGOs and hAGOs contained a supporting layer FOXF1+/VIM+ undifferentiated fibroblasts. Scale bars, 5 µm (a) and 100 µm (b).

Once regional domains are established in early development, the primitive gastric epithelium undergoes periods of growth, glandular morphogenesis, and differentiation of definitive cell types. Applicant previously showed that hAGOs underwent a similar progression of morphologic and cellular development7. CHIR-treated hFGOs grew at a similar rate and efficiency compared to hAGOs, as 75-90% of all spheroids plated grew into organoids (FIG. 8, *d*). At day 20, both types of hGOs contained epithelia that expressed the gastric SOX2/GATA4 signature in >90% of cells, while PDX1 was restricted to hAGOs (87.1±8.4% in hAGOs and 3.9±2.0% in hFGOs, p=3.07×10$^{-6}$; FIG. 8, *e*). The organoids maintained their respective gastric identities throughout their development (FIG. 8, b-c). By day 34, hFGOs and hAGOs comprised CDH1+CTNNB1+KRT8+ polarized, columnar epithelia that ubiquitously expressed the gastric-specific[17] claudin CLDN[18] (FIG. 2, *e* and FIG. 9, *d*), as well as comparable undifferentiated mesenchymal cells (FIG. 10, *b*). One notable difference was that hFGOs had a distinctive architecture with organized glands that bud from the organoid epithelium (FIG. 2, *d-e* and FIG. 10, *a*), while hAGOs had complex folding and primitive gland-like organization but rarely glandular buds[7]. Thus, the novel Wnt/β-catenin dependent mechanism of specifying fundus is conserved in humans and can be manipulated to generate three-dimensional hFGOs with a glandular epithelium that molecularly resembles the developing fundus.

Region-Specific Gastric Cytodifferentiation

Figure 3:
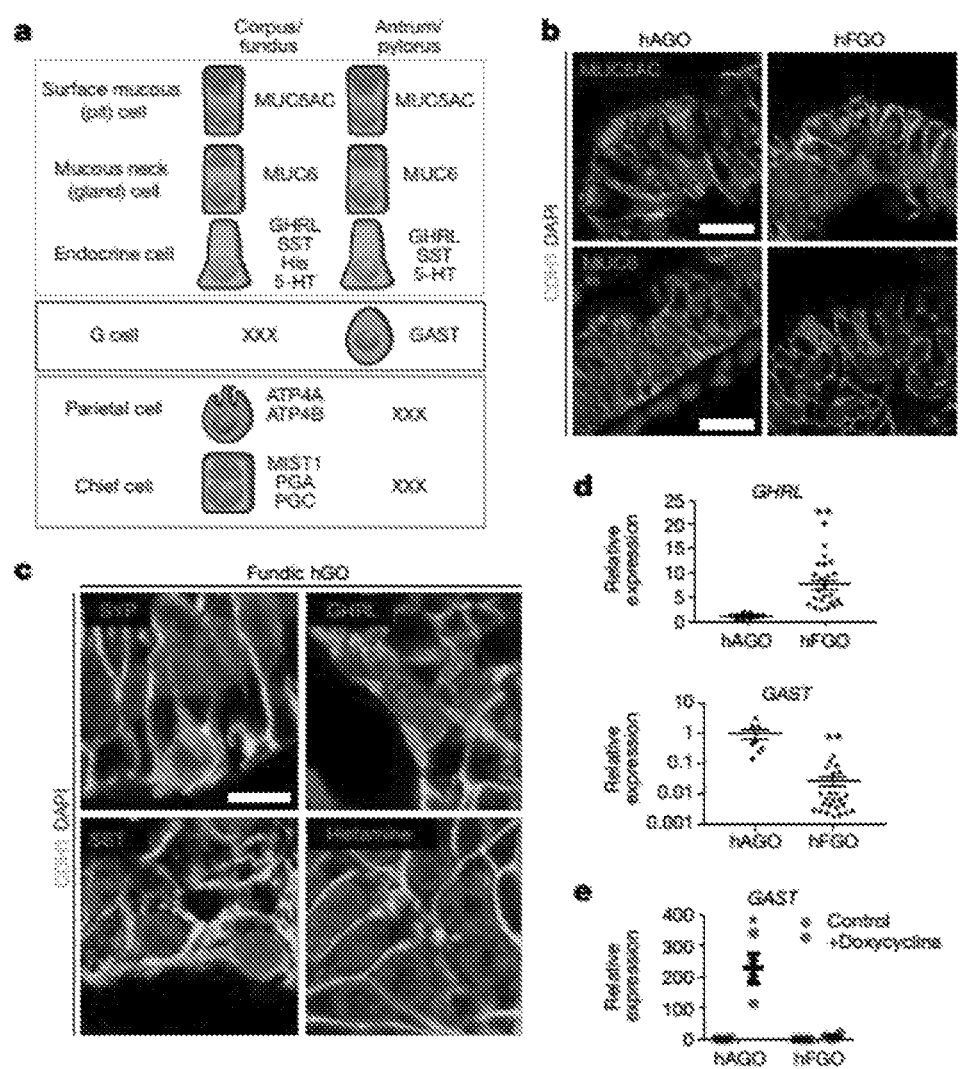
FIG. 3. Differentiation of mucous and endocrine cell lineages in hGOs. a, Schematic of the shared and distinct lineages found in fundic and antral glands of the stomach. b, Both antral and fundic hGOs contained MUC5AC-positive surface mucous cells and MUC6-positive mucous neck cells. c, d, hFGOs contained endocrine cells expressing the pan-endocrine marker SYP. Diverse hormone cell types were identified in hFGOs, including GHRL-, SST-, and histamine-expressing endocrine cells. The antral-specific G-cell marker GAST was expressed in hAGOs but not hFGOs; conversely, GHRL was enriched in hFGOs. **, $p<0.01$; two-tailed Student's t-test; n=8 and 24 biological replicates in hAGOs and hFGOs respectively, data representative of 6 independent experiments. e, hAGOs, but not hFGOs, were competent to give rise to antral-specific GAST-expressing endocrine cells in response to expression of the pro-endocrine transcription actor NEUROG3 (+dox). *, $p<0.01$; two-tailed Student's t-test; n=4 biological replicates, data representative of 3 independent experiments. Error bars represent s.e.m.
Figure 11:
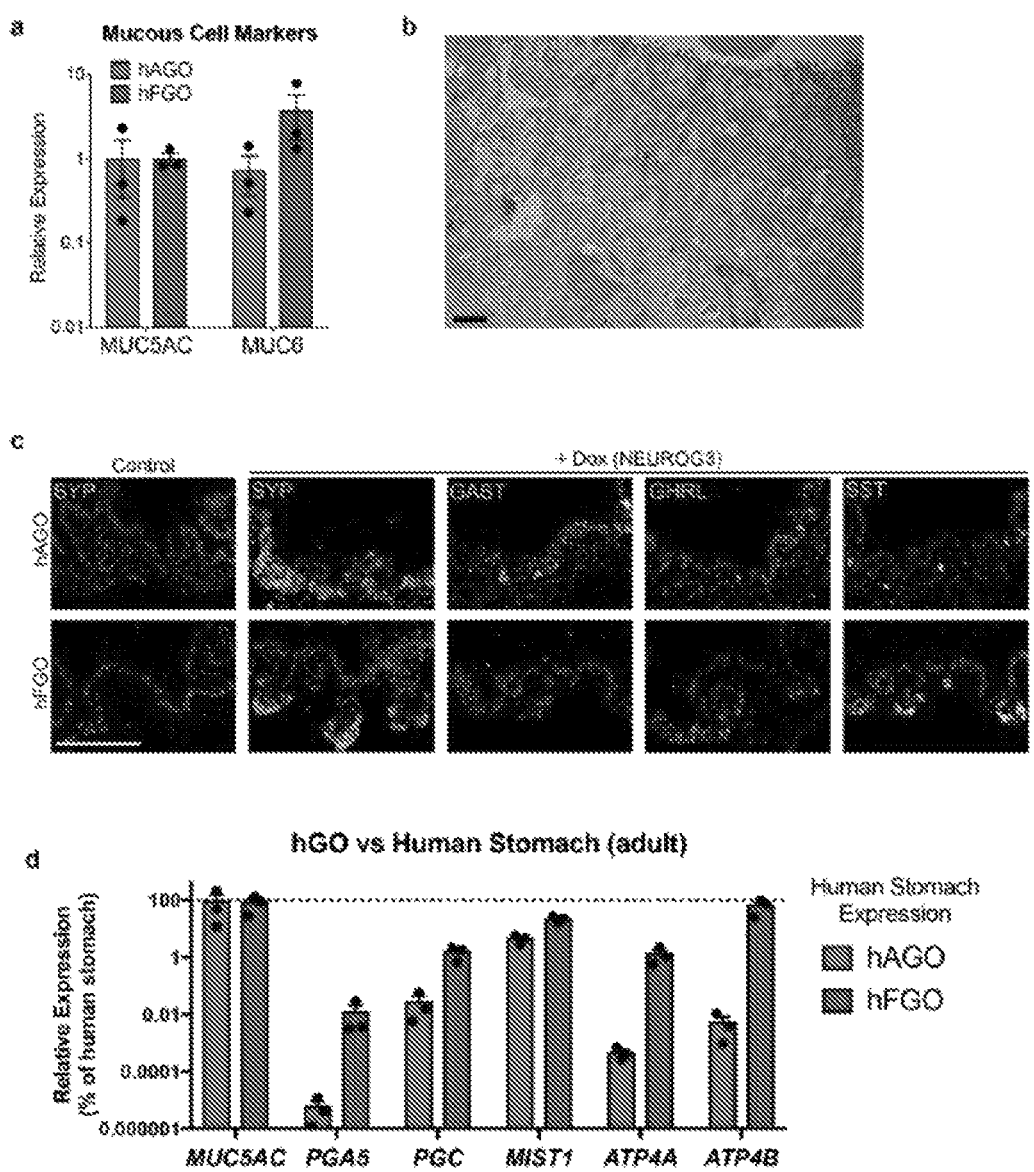
FIG. 11. Region-specific cytodifferentiation in human gastric organoids. a, Antral and fundic hGOs exhibited comparable expression of mucous cell markers MUC5AC and MUC6. b, As shown in transmission electron micrograph, hFGOs contained abundant cells exhibiting granule pattern consistent with mucous neck cells, the precursors to differentiated chief cells. c, Exogenous expression of NEUROG3 in hGOs derived from NEUROG3-deficient hESC line induced robust differentiation of SYP-positive endocrine cells. While both hAGOs and hFGOs formed GHRL- and SST-expressing endocrine cells, specification of GAST+ G-cells was observed only in hAGOs. d, Expression comparison of cell lineage markers in hGOs and human gastric biopsy tissue. qPCR analyses demonstrated that hGOs exhibited comparable expression levels of several lineage markers (MUC5AC, ATP4B), while other genes were expressed at much lower levels (ATP4A, PGA5, and PGC) than found in the fully differentiated, mature human stomach. Scale bars, 5 µm (b) and 100 µm (c). Error bars represent s.d. (a) and s.e.m. (b).

Differentiated antral gastric cell types were first detected in hAGOs around day 27 and then increased by day 347, analogous to the first few weeks of postnatal development in the mouse stomach[18]. At day 34, hFGOs contained both MUC5AC+ surface mucous cells and MUC6+ mucous neck cells as expected, similar to the hAGOs (FIG. 3, a-b and FIG. 11, a). hFGOs also formed a variety of endocrine cell types (FIG. 3, c), but expression of the hormone GAST was specific to hAGOs while GHRL was enriched 10-fold in hFGOs (FIG. 3, d), consistent with the normal gastroendocrine pattern[19]. To functionally define the region-specific competence of hGOs, Applicant used an inducible system to over-express the proendocrine transcription factor NEUROG3. Expression of NEUROG3 in both hGO subtypes resulted in robust expression of the pan-endocrine marker SYP, as well as the common gastric hormones SST and GHRL (FIG. 11, c). However, only the hAGOs and not hFGOs were competent to give rise to GAST-expressing G-cells (FIG. 3, e and FIG. 11, c), consistent with the antrum-specific distribution of G-cells in the human stomach[19].

Figure 4:
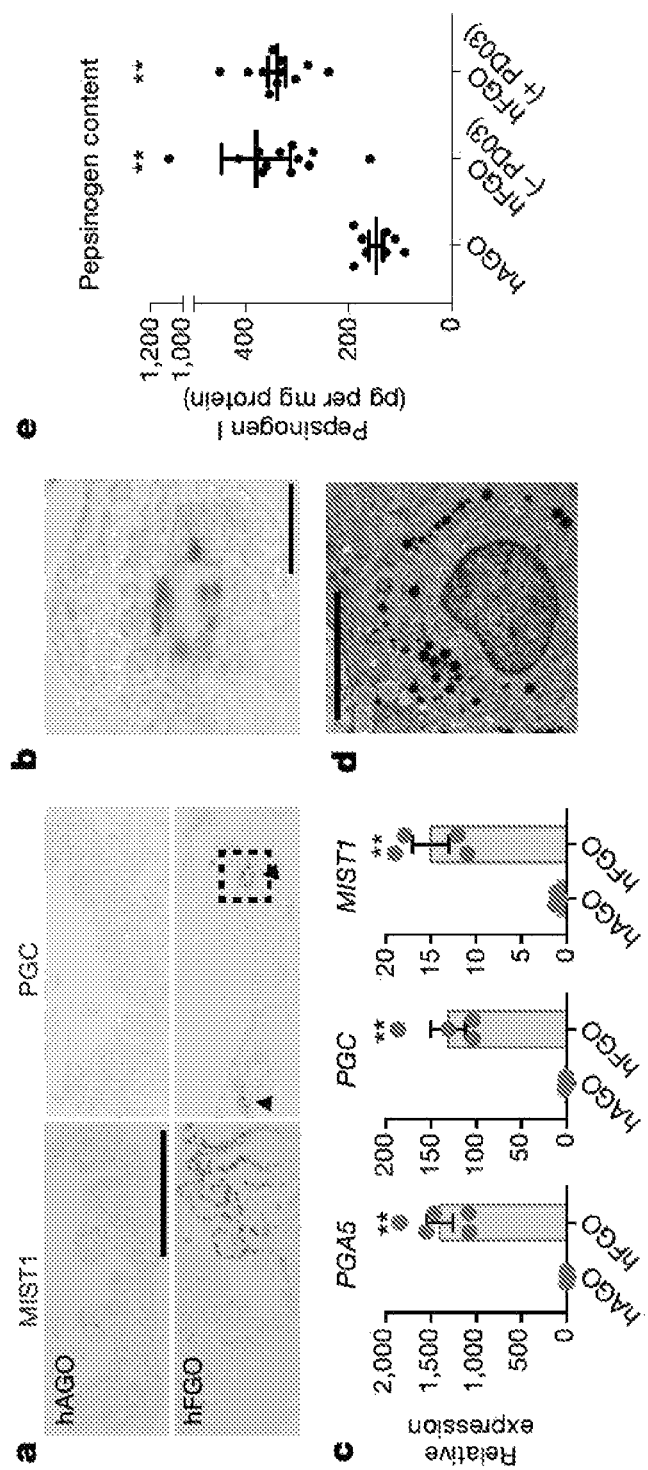
FIG. 4. Formation of chief cells in hFGOs. a, hFGOs had a both MIST1 and Pepsinogen C (PGC) positive cells. b, High magnification of boxed region in panel (a) showing a gland with a cluster of cells with apical PGC staining. c, hFGOs had significantly increased expression of chief cell markers PGA5 (1,000-fold), PGC (100-fold), and MIST1 (>10-fold) as compared to hAGOs. , $p<0.05$; two-tailed Student's t-test. n=3 biological replicates, data representative of 4 independent experiments. d, Transmission electron micrograph of an hFGO cell containing dense zymogen granules, indicative of a chief cell. e, Pepsinogen protein content in hFGOs as compared to hAGOs in the presence or absence of the MEK inhibitor (PD03). , $p<0.0001$ compared to hAGOs, two-tailed Student's t-test, n=8, 12, and 11 biological replicates in hAGOs, control hFGOs and hFGOs (no PD03), respectively. Scale bars, 200 µm (a), 25 µm (b), and 10 µm (d). Error bars represent s.e.m.
Figure 12:
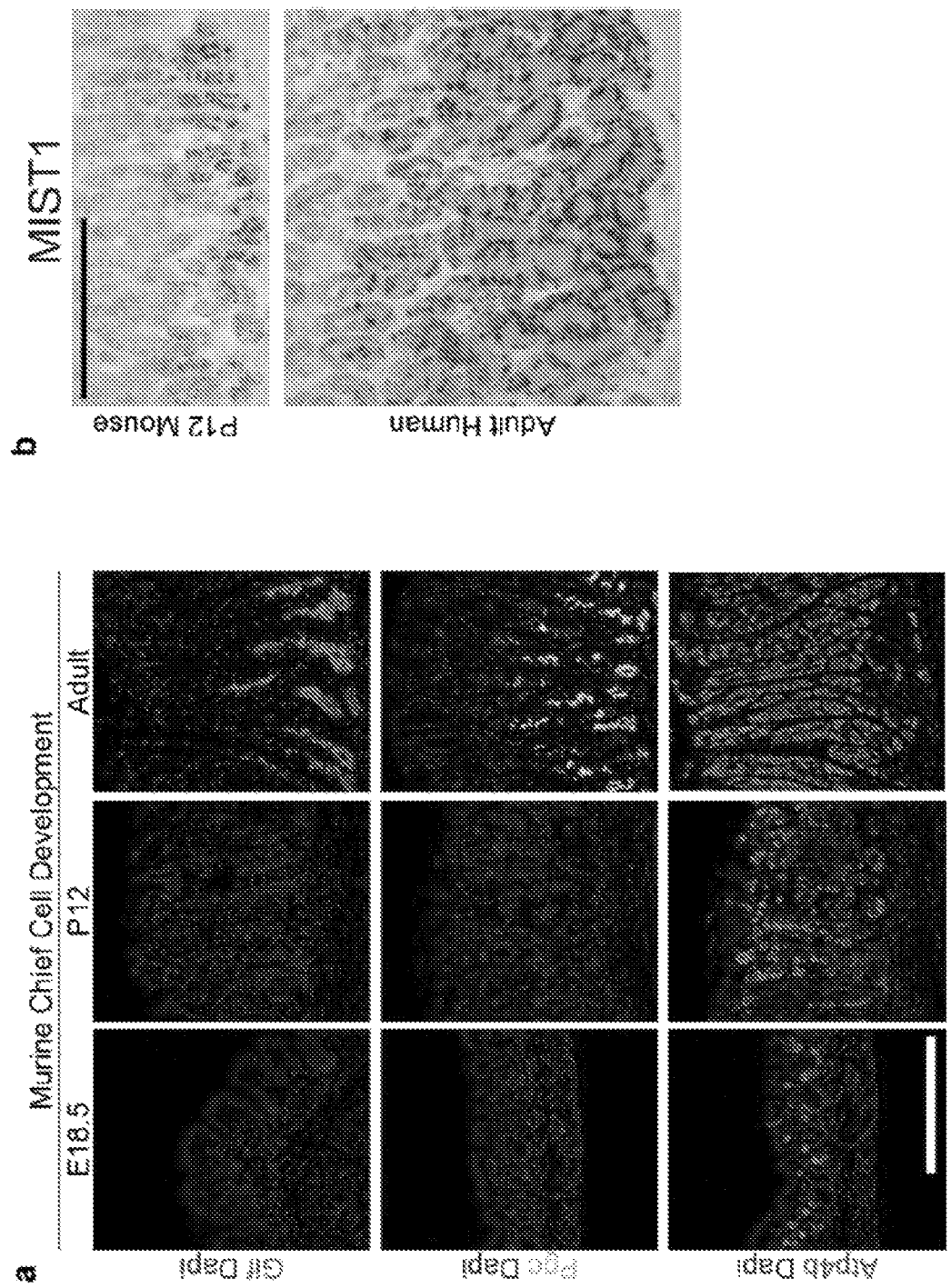
FIG. 12. Analysis of murine chief cell development. a, Unlike parietal cells, which expressed functional markers (Atp4b) as early as late embryonic stages, chief cell gene products were not detectable until much later stages of development. In the embryonic (E18.5) and juvenile (P12) stomach, Gif and Pgc were not yet expressed, indicating that chief cells mature much later in development than other lineages in the gastric epithelium. b, Despite the absence of Pgc, the P12 mouse stomach did contain abundant glandular cells expressing nuclear Mist1, a chief cell-specific marker. Thus, chief cells were indeed specified earlier but took several weeks to develop robust expression of terminal differentiation markers. Scale bars, 100 µm (a) and 200 µm (b).

Chief cells, the fundus-specific secretory lineage, reside in the base of oxyntic glands and have been proposed as a type of reserve stem cell[20]. hFGOs exhibited epithelial expression of the chief cell-specific[21] transcription factor MIST1 (FIG. 4, a), had 100-1,000-fold increases in transcripts for the proenzymes PGA5 and PGC (FIG. 4, c), and contained significantly increased pepsinogen content measured by ELISA (FIG. 4, e). However the transcript levels were less than 1% those found in the adult human stomach (FIG. 11, d) and pepsinogen-positive cells were only rarely detectable by immunohistochemistry (FIG. 4, b-c). Consistent with this, zymogen granule-containing cells[22] were identified by TEM (FIG. 4, d) but were rare. In contrast, cells with a more immature mucous granule pattern were abundant (FIG. 11, b). Since chief cells in vivo do not exhibit robust pepsinogen expression for the first few weeks of life (FIG. 12, a-b), Applicant concluded that the chief cells were present in hFGOs but were immature. hFGOs therefore represent a robust platform to dissect the intrinsic and extrinsic mechanisms that regulate chief cell maturation.

Pathways Controlling Parietal Cell Differentiation

Figure 5:
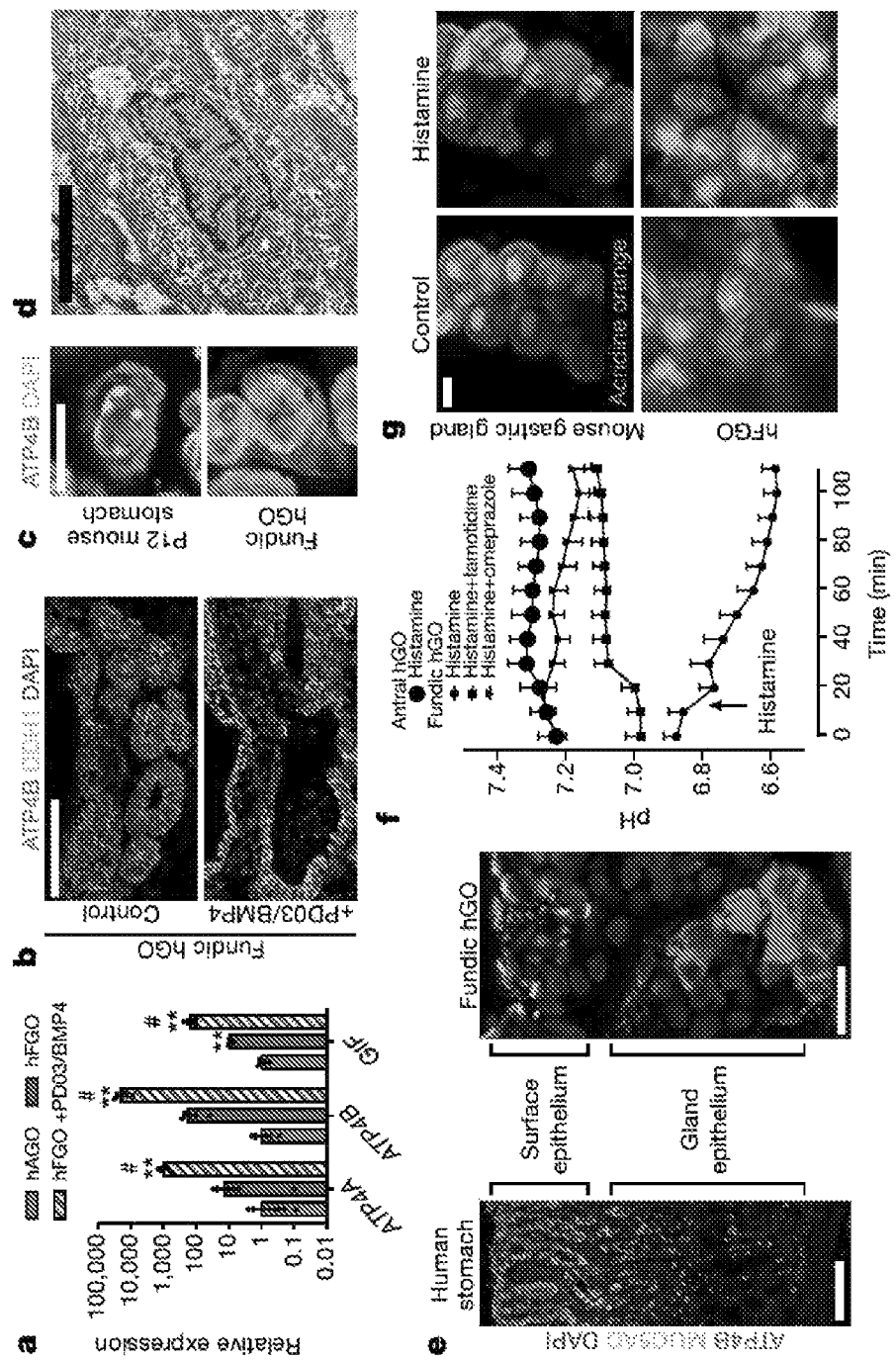
FIG. 5. Identification of pathways that drive differentiation of functional parietal cells in hFGOs. a, Expression of parietal cell genes ATP4, ATP4B, and GIF exhibited 10-100-fold increase in hFGOs compared to antral at baseline, but was dramatically increased by exposing hFGOs to a two-day pulse of PD03/BMP4. **, $p<0.05$ compared to hAGOs; #, $p<0.05$ compared to control hFGOs, two-tailed Student's t-test, n=4 biological replicates, data representative of 15 independent experiments. b, Stimulated differentiation of ATP4B-expressing parietal cells following treatment with PD03/BMP4. c, hFGO-derived parietal cells resembled those found in the maturing mouse fundic epithelium in vivo. d, Transmission electron micrograph of an hFGO cell with canalicular structure reminiscent of parietal cells. e, The epithelium of human fundic glands and hFGO epithelium were organized into MUC5AC-expressing cells in the surface epithelium and ATP4B-expressing parietal cells in the glandular units. f, Analysis of luminal pH in organoids in response to histamine by luminal injection of SNARF-5F. The luminal pH in hFGOs rapidly dropped, while hAGOs exhibited no response. The acidification was blocked by pretreating the organoids with either famotidine or omeprazole. n=9, 9, 7, and 4 biological replicates in hFGOs (histamine), hFGOs (histamine and famotidine), hFGOs (histamine and omeprazole), and hAGOs (histamine), respectively; data representative of three independent experiments. g, Histamine induced acridine orange (AO) dye accumulation in a canalicular-type pattern in isolated mouse gastric glands and in hFGOs after 60 minutes. Scale bars, 100 µm (b), 10 µm (c), 10 µm (d), 100 µm (e; human fundus), 20 µm (e; hFGO), and 10 µm (g). Error bars represent s.e.m.
Figure 13:
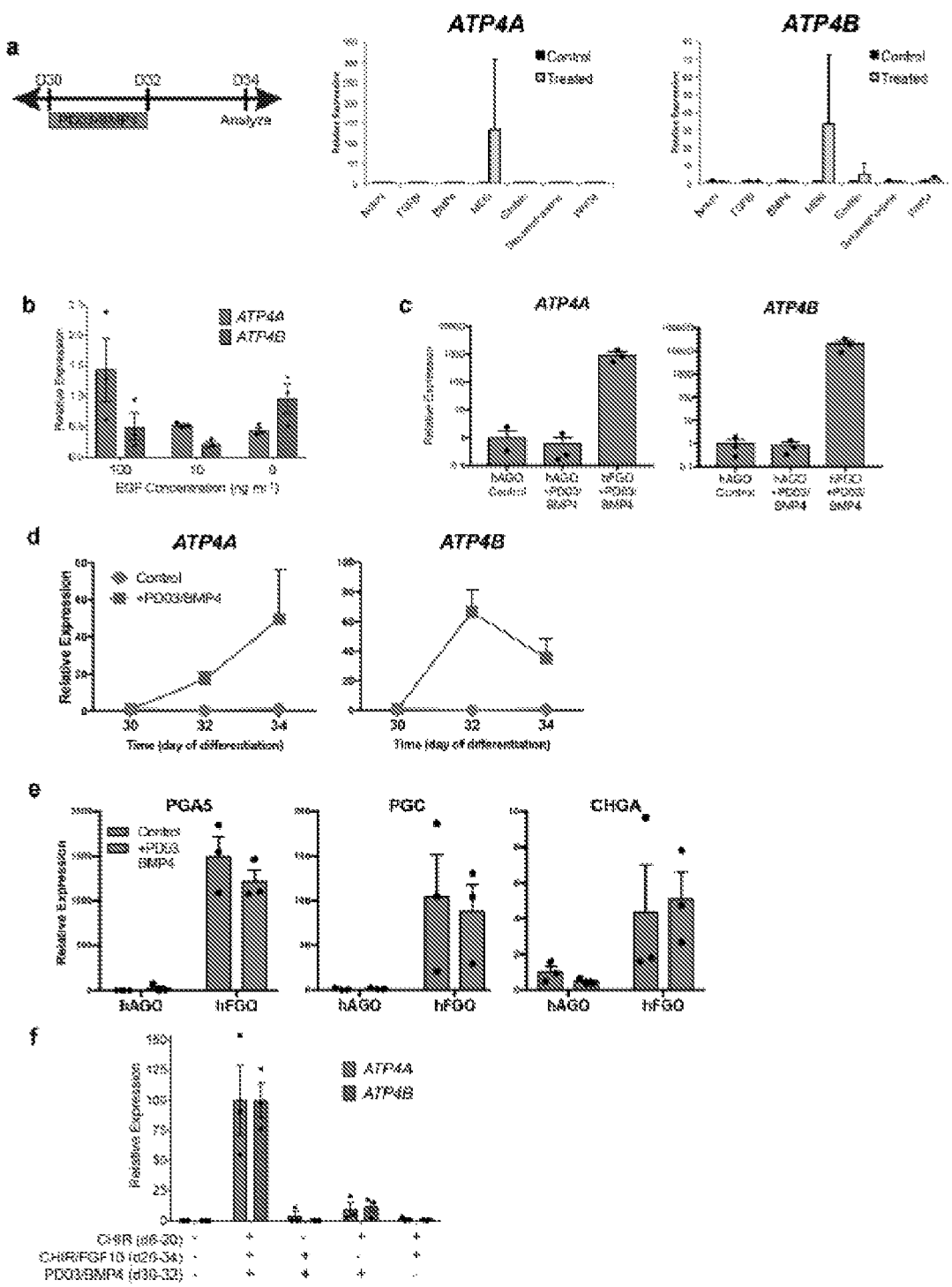
FIG. 13. Screen for pathways that promote differentiation of parietal cells in fundic hGOs. a, To test for growth factors/small molecules capable of inducing parietal cell differentiation, hFGOs were exposed for two days (30-32) to the indicated agonist or antagonist and then analyzed at day 34. In a screening experiment of different pathways, only MEK inhibition with PD03 was found to robustly induce expression of ATP4A/B. b, Reduction or removal of EGF from the culture medium was not sufficient to reproduce the effect of MEK inhibition. c, The ability of PD03/BMP4 to induce parietal cell development was exclusive to fundic hGOs, as antral hGOs did not express fundic markers in response to PD03/BMP4. d, Exposure to PD03/BMP4 rapidly increased expression of ATP4A and ATP4B in fundic hGOs. e, Induction of parietal cell generation with PD03/BMP4 did not significantly impact the differentiation of chief cells (PGA5 and PGC) and endocrine cells (CHGA). f, The manipulations at each stage of the hFGO differentiation protocol was required for robust parietal cell differentiation, as removal of any single step led to loss of ATP4A/B expression. Error bars represent s.d. (a-c) and s.e.m. (d-f).

At baseline, hFGOs contained only a small number of parietal cells (PCs; FIG. 5, a-b), the defining cell type of fundic glands that acidify the gastric lumen via the proton pump (consisting of ATP4A and ATP4B subunits). Identification of efficient methods to increase PC populations has remained elusive due to a lack of understanding of the signaling mechanisms that drive their development. Applicant therefore used PSC-derived hFGOs as a platform to functionally screen candidate signaling pathways for a role in regulating PC differentiation. For screening, Applicant exposed day 30 hFGOs to signaling agonists or antagonists for two days and analyzed PC differentiation at day 34. While the majority of signaling manipulations had no appreciable effect, transient inhibition of the MEK pathway with PD0325901 (PD03) resulted in substantial up-regulation of both ATP4A and ATB4B (FIG. 13, a). Further, while BMP4 alone did not affect PC gene expression, it could enhance the effect of PD03 (data not shown). Thus, a two-day pulse of PD03/BMP4 was sufficient to induce rapid and robust expression of PC markers ATP4A, ATP4B and GIF (FIG. 5, a-b and FIG. 13, d). Interestingly, this effect was not observed by simply removing EGF or FGF from the culture medium (FIG. 13, b), suggesting that there are likely endogenous signaling interactions upstream of MEK/ERK that are responsible for limiting PC differentiation in hFGO cultures. Further, PD03/BMP4 treatment only affected the PC lineage (FIG. 13, e), and was unable to induce PCs in hAGOs (FIG. 13, c), further emphasizing that early patterning of the gastric epithelium defines its ultimate differentiation potential.

Figure 14:
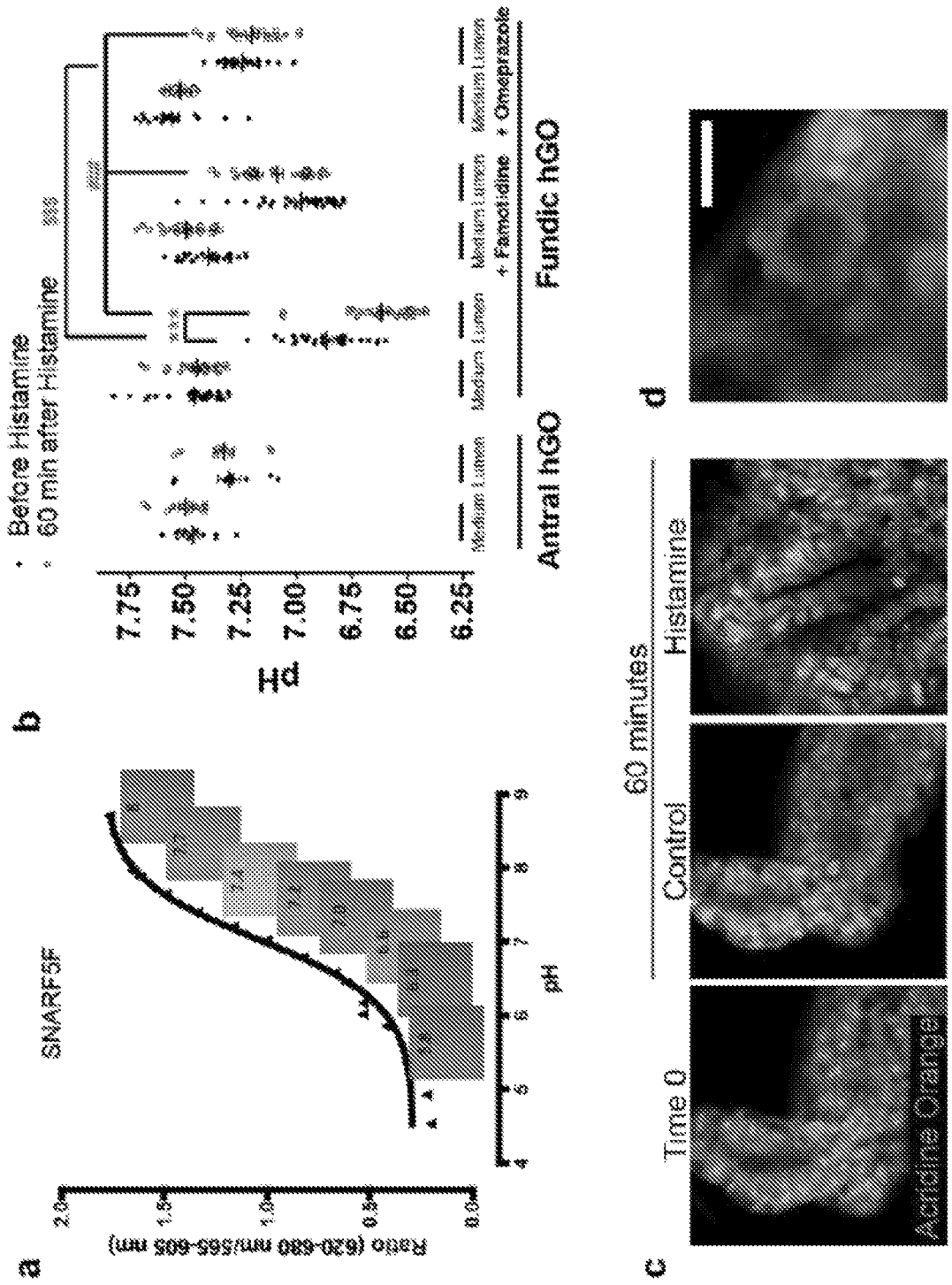
FIG. 14. Live in vitro pH monitoring in gastric organoids. a, The dye SNAFR5F exhibits responsiveness over pH range of 5-8, which makes it well suited to detect physiologic changes in response to parietal cell-mediated acid secretion. b, Media and luminal pH measurements recorded before (closed circles) and 60 minutes following addition of histamine (open circles). Antral hGOs did not respond, while the fundic hGO luminal pH decreased in response to histamine. The acidification was inhibited by pre-treatment of organoids with either famotidine or omeprazole. Further, omeprazole was sufficient to raise the pH in fundic organoids prior to histamine exposure, suggesting a baseline acid secretion in the fundic organoids. Media pH did not change in any organoids. ***, $p<0.001$ compared to before histamine; \$\$\$, $p<0.001$ compared to luminal pH without histamine; ###, $p<0.001$ compared to luminal pH with histamine; two tailed Student's t-test. c, hFGOs contained parietal cell-dense glands in which acridine orange (AO) accumulated in nearly all of the cells lining the lumen of the gland. d, AO accumulation was observed in a canalicular-type pattern in parietal cells in hFGOs. Scale bars, 10 µm. Error bars represent s.d.

At day 34 hFGO epithelia exhibited comparable organization to the human stomach, with mucous cells lining the surface domain and PCs concentrated in the glandular portion (FIG. 5, e). Moreover, parietal cell morphology closely resembled maturing parietal cells in vivo (FIG. 5, c). Given their resemblance to PCs in vivo and their tubulovesicular ultrastructure as seen on TEM (FIG. 5, d), Applicant hypothesized that the PCs in hFGOs would exhibit the ability to secrete acid in response to appropriate stimuli. Measured using a pH sensitive dye (SNARF5F) with real time confocal microscopy (FIG. 14, a), hFGOs produced a swift and marked decrease in luminal pH in response to histamine that was blocked by either the H2 antagonist famotidine or the H+K+-ATPase antagonist omeprazole (FIG. 5, f and FIG. 14, b). To visualize the cellular response to histamine, hGOs were cultured with the fluorescent dye acridine orange (AO), which shifts to an orange color when sequestered in acidic compartments[23]. Similar to isolated mouse gastric glands, AO accumulated in acidified cellular vesicles in hFGO glands in response to histamine (FIG. 5, g and FIG. 14, c-d). These data indicate that the PCs underwent appropriate changes in secretory canalicular structure in response to acid-inducing stimuli.

Figure 15:
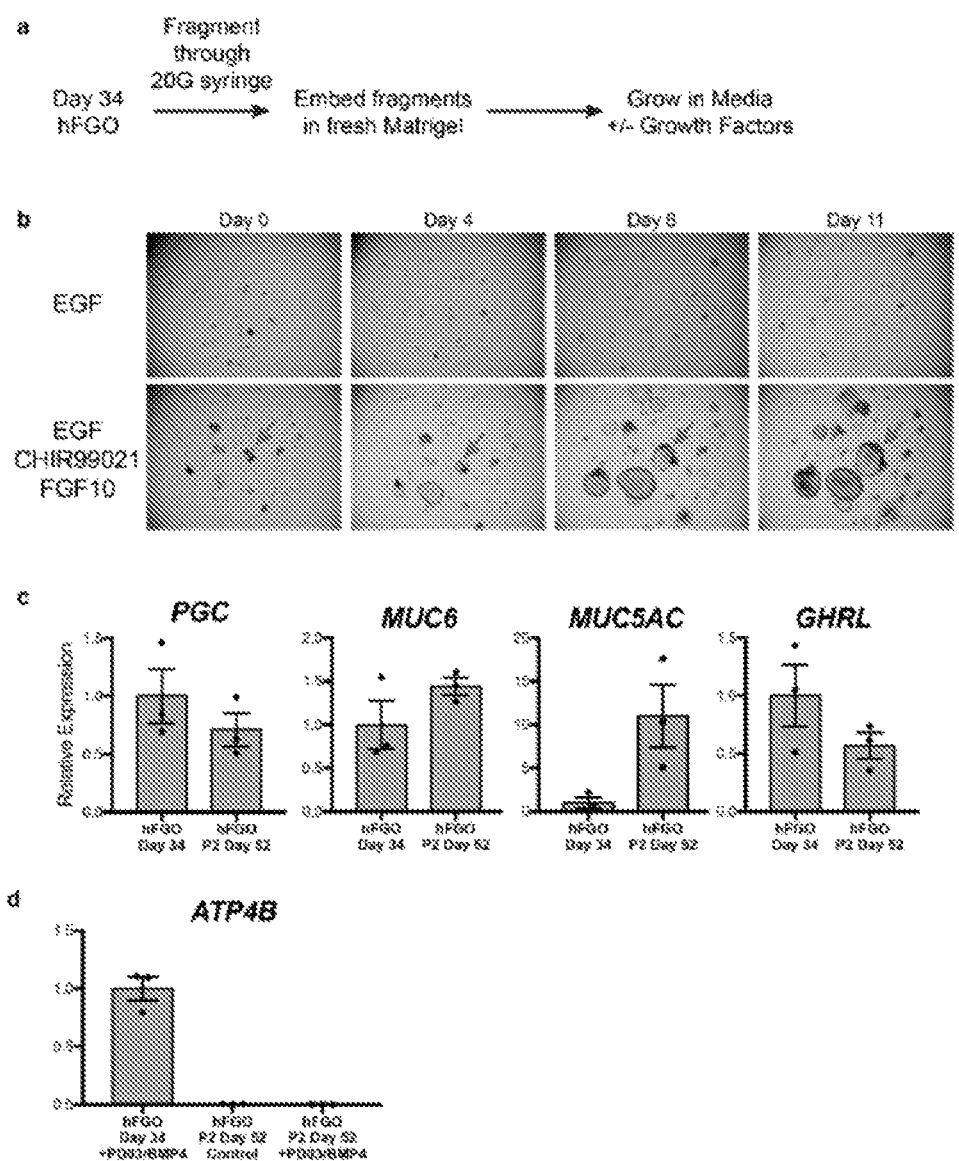
FIG. 15. Serial passaging of human gastric organoids. a, Schematic representation of experiments to determine the presence of gastric stem cells in hGOs. b, When fragments were grown in culture medium containing only EGF, they did not grow or expand to form new organoids. However, addition of CHIR and FGF10 to the culture medium was sufficient to support the growth of individual fragments into newly formed organoids. c, Following two passages, hFGOs still expressed genes consistent with a gastric phenotype, including PGC, MUC6, MUC5AC, and GHRL. This ability to undergo serial passaging with maintenance of gastric identity supports the conclusion that hFGOs contain cells with properties analogous to those of adult gastric stem cells. d, Although passaged hFGOs expressed markers associated with several differentiated gastric cell types, they did not express genes associated with parietal cells such as ATP4B.

In vivo, differentiated gastric cell lineages are thought to derive from a common pool of undifferentiated stem or progenitor cells. Here Applicant has demonstrated the ability to alter the relative proportions of cell types in hFGOs, either through genetic means (NEUROG3-mediated regulation of endocrine cells) or by manipulation of extrinsic signaling pathways (PD03/BMP4 for PCs). These observations led to the hypothesis that hFGOs might contain a population of gastric stem cells analogous to those that have been isolated from the adult stomach. Indeed, Applicant found that dissociated day 34 hFGOs could be passaged serially to give rise to new organoids (FIG. 15, a-b). Re-growth of organoids from passaged hFGOs was dependent on high Wnt and high FGF culture medium, similar to what is used to grow primary gastric tissue organoids[24,25]. Following two rounds of passaging, hFGOs maintained expression of lineage markers MUC5AC, MUC6, PGC, and GHRL; however, they did not contain PCs and were refractory to PD03/BMP4-mediated induction of the parietal lineage (FIG. 15, c-d). This finding was similar to what has been observed in adult stem cell-derived gastric organoids, which do not robustly produce PCs despite being derived from the bona fide oxyntic mucosa[20,26]. Thus it will be important to identify conditions that preserve PC competence in long-term cultures of hGOs and adult gastric organoids.

In summary, Applicant has directly applied in vivo and in vitro discovery-based studies towards the differentiation of hPSCs into a new tissue type. Applicant has defined a novel function of Wnt/β-catenin signaling in specifying the fundic domain during stomach development in mice, and used Wnt modulation as the mechanistic basis to direct differentiation of hPSCs into three-dimensional human fundic organoids. In both mouse and human, Wnt-mediated fundus specification was led to the subsequent formation of PCs. The fundus-specific manipulations at each stage of this directed differentiation protocol led to robust PC induction (FIG. 13, f). Previous reports identified that the mesenchymal factor Barx1 indirectly acts to repress Wnt signaling and that helps to prevent intestinal gene expression in the stomach[14,15]. Given that the current study identified an epithelial Wnt/β-catenin function, and the previous work identified a mesenchymal pathway, it seems likely that Wnt/β-catenin may have distinct roles in the epithelium versus mesenchyme. For example, the mesenchymal role for Wnt/β-catenin could modulate other signaling pathways such as BMP[27], which our data show synergizes with Wnt to promote intestinal specification from early endoderm (FIG. 7 and FIG. 9, c) The human gastric organoid systems might be useful, in combination with animal models, to dissect how these signaling pathways interact in the mesenchyme and epithelium to coordinate early embryonic gastrointestinal development.

Pathways that control differentiation of gastric progenitor cells into distinct lineages are also lacking. Applicant has demonstrated the utility of this new hGO platform to identify that MEK/ERK signaling potently represses parietal cell specification. Consistent with these findings, transgenic activation of MEK/MAPK-dependent pathways led to loss of parietal cells in vivo[28,29]. Therefore, hGOs are a new and tractable human model system to identify and study signaling mechanisms involved in normal cellular homeostasis in the fundus and antrum. Further, aberrant regulation of developmental programs may also contribute to gastric disease, as corpus/fundus pathology is often associated with parietal cell atrophy[30-32], antral-type histology[33], and even misexpression of Pdx134. Thus targeting of these pathways could have clinical utility, as Choi et. al. recently demonstrated that pharmacologic inhibition of MEK was sufficient to restore normal parietal cell differentiation in a mouse model of metaplasia[35]. Additionally, having now established both antral- and fundic-type hGOs, it is possible to study how these human gastric tissues interact physiologically, differentially respond to infection and injury, and respond to pharmacologic treatments.

Methods

Mouse Experiments

The following genetic mouse strains were obtained from The Jackson Laboratory, housed at Cincinnati Children's Hospital Research Foundation animal facility, and maintained according to IACUC protocol (0B09074): Axin2: LacZ (stock no. 009120), Shh:Cre (stock no. 005622), and β-cateninfloxed (stock no. 004152). Timed matings, with the morning the vaginal plug was observed being denoted as E0.5, were used to generate embryos at various stages that were harvested for either wholemount staining or tissue dissection. At least two litters of embryos were analyzed at each developmental stage examined. Both male and female embryos were analyzed.

Pluripotent Stem Cell Culture

Human embryonic stem cell line WA01 (H1; obtained from WiCell) was supplied by the Pluripotent Stem Cell Facility at Cincinnati Children's Hospital Medical Center. Cell identity was confirmed by short tandem repeat analysis (Microsatellite STR Analysis; Applied Biosystems), and cells were routinely tested for *mycoplasma* contamination (MycoAlert *Mycoplasma* Detection Kit; Lonza). Pluripotent cells were maintained in feeder-free conditions on HESC-qualified Matrigel (BD Biosciences) in mTesR1 media (Stem Cell Technologies). Colonies were passaged every four days using dispase (Invitrogen).

Differentiation of Posterior Foregut Spheroids

The protocol for directed differentiation of gastric organoids was adapted from our previous protocol[7], and Table 1 contains the complete list of media and growth factors for each stage. For differentiation, hPSCs were dissociated into single cells using Accutase (Stem Cell Technologies) and plated into 24-well plates at a density of roughly 200,000 cells per well in mTesR1 with Y-27632 (10 μM; Stemgent). The following day, cells were differentiated into definitive endoderm (DE) by adding Activin A (100 ng/ml; Cell Guidance Systems) in RPMI 1640 media (Invitrogen) for three days. Media was also supplemented with NEAA (1×; Gibco) and defined FBS (dFBS; Invitrogen) at 0%, 0.2%, and 2.0% on days 1, 2, and 3, respectively. Additionally, BMP4 (50 ng/ml; R&D Systems) was added on the first day. Subsequently, DE was differentiated to posterior foregut endoderm by exposing cells to CHIR99021 (2 μM; Stemgent), FGF4 (500 ng/ml; R&D Systems), and Noggin (200 ng/ml; R&D systems) for three days in RPMI 1640 supplemented with NEAA and 2.0% dFBS. Retinoic acid (2 μM; Sigma Aldrich) was added for the final day. Media was changed every day. This process resulted in the spontaneous formation of three-dimensional posterior foregut spheroids.

TABLE 1

Differentiation protocol for fundic hGOs. Activin A (100 ng/ml; R&D Systems), CHIR99021 (2 uM; Stemgent), FGF4 (500 ng/ml; R&D systems), PD0325901 (2 uM; Stemgent), BMP4 (50 ng/ml; R&D Systems).

| Day | Base Media | Supplement | Activin A | CHIR99021 | FGF4 | Noggin | RA | EGF | FGF10 | PD03 | BMP4 |
|---|---|---|---|---|---|---|---|---|---|---|---|
| 0-1 | RPMI | NEAA | + | | | | | | | | + |
| 1-2 | RPMI | 0.2% FCS, NEAA | + | | | | | | | | |
| 2-3 | RPMI | 2.0% FCS, NEAA | + | | | | | | | | |
| 3-5 | RPMI | 2.0% FCS, NEAA | | + | + | + | | | | | |
| 5-6 | RPMI | 2.0% FCS, NEAA | | + | + | + | + | | | | |
| 6-9 | BGM* | n/a | | +** | | | + | + | + | | |
| 9-13 | BGM* | n/a | | +** | | | + | | + | | |
| 13-20 | BGM* | n/a | | +** | | | | | + | | |
| 20-30 | BGM* | n/a | | +** | | | | | + | +** | |
| 30-32 | BGM* | n/a | | +** | | | | | + | +** | + | + |
| 32-34 | BGM* | n/a | | +** | | | | | + | +** | | |

*BGM (basic gut media) = Advanced DMEM/F12, N2 (1X; Invitrogen), B27 (1X; Invitrogen) L-glutamine, HEPES (10 uM), and penicillin/streptomycin.
**Specific to fundus hGO protocol.

Three-Dimensional Culture of Foregut Spheroids-Gastric Organoids

Posterior foregut spheroids were collected and transferred to a three-dimensional culture system as previously described[36]. Briefly, spheroids were suspended in 50 µl Matrigel (BD Biosciences) and plated as a droplet into 24-well plates. The matrigel was allowed to solidify for 10 minutes in the tissue culture incubator, then overlayed with basic gut media (BGM) containing growth factors and/or small molecule agonsists. BGM consisted of Advanced DMEM/F12 media (Gibco) supplemented with N2 (1×; Invitrogen), B27 (1×; Invitrogen), HEPES (10 µM; Gibco), L-glutamine, penicillin/streptomycin, and EGF (100 ng/ml; R&D Systems). During days 6-9, spheroids were cultured with RA and noggin to specify the antral lineage. For fundic specification, CHIR was added during this stage. Antral hGOs were subsequently cultured in BGM with only EGF. Fundic hGOs were continuously exposed to CHIR from day 6-30. In addition, FGF10 (50 ng/ml; R&D Systems) was added to fundic hGOs from day 20-30 as it was shown to enhance the glandular morphogenesis driven by CHIR (data not shown). On day 20, organoids were collected and re-plated at a dilution of 1:10-1:20.

For screening experiments to identify factors that increase parietal cell differentiation, hFGOs were grown to day 30, then exposed for two days to individual signaling pathway agonists and antagonists: DAPT (1 µM; Stemgent), SB431542 (10 µM; Stemgent), BMP4 (50 ng/ml; R&D Systems), PD0325901 (2 µM; Stemgent), Gastrin (10 nM; Sigma Aldrich), Dexamethasone (50 nM; Sigma Aldrich), and Wnt5a (50 ng/ml; R&D Systems). Following treatment, hFGOs were grown for two more days to day 34, then analyzed by qPCR.

RNA Isolation and qPCR

Total RNA was isolated using Nucleospin RNA II kit (Machery Nagel) and converted to cDNA as previously described7. qPCR was performed on Quantstudio 6 (Applied Biosystems) using Quantitect SYBR-Green master mix (Qiagen), and primer sequences are listed below.

```
Primer Sequences
Primers used for qPCR were the following:
hATP4A,
forward
5'-TGGTAGTAGCCAAAGCAGCC-3', reverse
5'-TGCCATCCAGGCTAGTGAG-3';

hATP4B,
forward
5'-ACCACGTAGAAGGCCACGTA-3', reverse
5'-TGGAGGAGTTCCAGCGTTAC-3';

hAXIN2,
forward
5'-CTGGTGCAAAGACATAGCCA-3', reverse
5'-AGTGTGAGGTCCACGGAAAC-3';

hCCK,
forward
5'-CGGTCACTTATCCTGTGGCT-3', reverse
5'-CTGCGAAGATCAATCCAGCA-3';

hCDX2,
forward
5'-CTGGAGCTGGAGAAGGAGTTTC-3', reverse
5'-ATTTTAACCTGCCTCTCAGAGAGC-3';

hCHGA,
forward
5'-TGACCTCAACGATGCATTTC-3', reverse
5'-CTGTCCTGGCTCTTCTGCTC-3';

hGAPDH,
forward
5'-CCCATCACCATCTTCCAGGAG-3', reverse
5'-CTTCTCCATGGTGGTGAAGACG-3';

hGAST,
forward
5'-CAGAGCCAGTGCAAAGATCA-3', reverse
5'-AGAGACCTGAGAGGCACCAG-3';

hGATA4,
forward
5'-TCCAAACCAGAAAACGGAAGC-3', reverse
5'-GCCCGTAGTGAGATGACAGG-3';

hGHRL,
forward
5'-GCTGGTACTGAACCCCTGAC-3', reverse
5'-GATGGAGGTCAAGCAGAAGG-3';

hGIF,
forward
5'-CATTTTCCGCGATATTGTTG-3', reverse
5'-GCACAGCGCAAAAATCCTAT-3';

hIRX2,
forward
5'-GTGGTGTGCGCGTCGTA-3', reverse
5'-GGCGTTCAGCCCCTACC-3';

hIRX3,
forward
5'-GGAGAGAGCCGATAAGACCA-3', reverse
5'-AGTGCCTTGGAAGTGGAGAA-3';

hIRX5,
forward
5'-GGTGTGTGGTCGTAGGGAGA-3', reverse
5'-GCTACAACTCGCACCTCCA-3';

hMIST1,
forward
5'-TGCTGGACATGGTCAGGAT-3', reverse
5'-CGGACAAGAAGCTCTCCAAG-3';

hMUC2,
forward
5'-TGTAGGCATCGCTCTTCTCA-3',
``` reverse
5'-GACACCATCTACCTCACCCG-3';

hMUC5AC,
forward
5'-CCAAGGAGAACCTCCCATAT-3', reverse
5'-CCAAGCGTCATTCCTGAG-3';

hMUC6,
forward
5'-CAGCAGGAGGAGATCACGTTCAAG-3', reverse
5'-GTGGGTGTTTTCCTGTCTGTCATC-3';

hPDX1,
forward
5'-CGTCCGCTTGTTCTCCTC-3', reverse
5'-CCTTTCCCATGGATGAAGTC-3';

hSCT,
forward
5'-GGTTCTGAAACCATAGGCCC-3', reverse
5'-GTCAGGGTCCAACATGCC-3';

hSOX2,
forward
5'-GCTTAGCCTCGTCGATGAAC-3', reverse
5'-AACCCCAAGATGCACAACTC-3';

mCdx2,
forward
5'-TCTGTGTACACCACCCGGTA-3', reverse
5'-GAAACCTGTGCGAGTGGATG-3';

mGata4,
forward
5'-CCATCTCGCCTCCAGAGT-3', reverse
5'-CTGGAAGACACCCCAATCTC-3';

mGapdh,
forward
5'-TTGATGGCAACAATCTCCAC-3', reverse
5'-CGTCCCGTAGACAAAATGGT-3';

mIrx1,
forward
5'-AATAAGCAGGCGTTGTGTGG-3', reverse
5'-CTCAGCCTCTTCTCGCAGAT-3';

mIrx2,
forward
5'-AGCTGGTATGGATAGGCCG-3', reverse
5'-GGCTTCCCGTCCTACGTG-3';

mIrx3,
forward
5'-ATAAGACCAGAGCAGCGTCC-3', reverse
5'-GTGCCTTGGAAGTGGAGAAA-3';

mIrx5,
forward
5'-GGAGTGTGGTCGTAGGGAGA-3', reverse
5'-GCTACAACTCGCACCTCCA-3';

mPdx1,
forward
5'-ACGGGTCCTCTTGTTTTCCT-3', reverse
5'-TGGATGAAATCCACCAAAGC-3';

mPitx1,
forward
5'-GTCCATGGAGGTGGGGAC-3', reverse
5'-GCTTAGGCGCCACTCTCTT-3';

mSox2,
forward
5'-AAAGCGTTAATTTGGATGGG-3', reverse
5'-ACAAGAGAATTGGGAGGGGT-3';

mTrp63,
forward
5'-AGCTTCTTCAGTTCGGTGGA-3', reverse
5'-CCTCCAACACAGATTACCCG-3'.

Immunofluorescent Staining

Tissues were fixed in 4% paraformaldehyde overnight at 4° C., then washed thoroughly in PBS. For wholemount immunofluorescent staining, embryos were processed as previously described37. Briefly, they were permeabilized in Dent's Bleach (4:1:1 EtOH:DMSO:30% H2O2) for two hours at room temperature and rehydrated through series of methanol washes. Embryos were then blocked for one hour, incubated in primary antibody overnight at 4° C., washed in PBS, incubated in primary antibody overnight at 4° C., and thoroughly washed. For paraffin embedding, tissues were dehydrated through series of ethanol washes, washed in xylene, then embedded in paraffin. For staining, slides were deparaffinized and rehydrated. Antigen retrieval was performed in citrate buffer for 45 minutes in steamer. Primary antibodies were incubated overnight at 4° C. Following primary antibody, slides were washed in PBS then incubated with secondary antibody (at dilution of 1:500) for one hour at room temperature. Secondary antibodies (Jackson ImmunoResearch Laboratories) were made in donkey and conjugated to Alexa Fluor 488, 594, or 647.

Primary Antibodies

Antibodies used for immunofluorescent staining are listed with antigen, host species, manufacturer and catalogue number, and dilution used for staining. Atp4b, rabbit, Santa Cruz sc84304, 1:500; Cdh1, goat, R&D Systems AF648, 1:500; Cdh1, mouse, BD Biosciences 610182, 1:500; Cdx2, mouse, Biogenex MU392A, 1:500, Cldn18, rabbit, Sigma HPA018446, 1:200; Ctnnb1, rabbit, Santa Cruz sc7190, 1:100; FoxF1, goat, R&D Systems F4798, 1:500, Gastrin, rabbit, Dako A0568, 1:1,000; Gata4, goat, Santa Cruz sc1237, 1:200; Gif, rabbit, Sigma HPA040774, 1:100; Ghrl, goat, Santa Cruz sc10368, 1:200; Histamine, rabbit, Immunostar 22939, 1:1,000; Krt8, rat, DSHB troma-1-s; 1:100; Mist1, rabbit, Sigma HPA047834, 1:200; Muc5ac, mouse, Abcam ab3649, 1:500; Muc6, mouse, Abcam ab49462, 1:100; Pdx1, goat, Abcam ab47383, 1:5,000; Pgc, sheep, Abcam ab31464, 1:10,000; Sst, goat, Santa Cruz sc7819, 1:100; Syp, guinea pig, Synaptic Systems 101004, 1:1,000; Vimentin, goat, Santa Cruz sc7557, 1:200

Imaging

Confocal imaging was performed on Nikon A1Rsi inverted confocal microscope. For wholemount imaging, embryos were dehydrated in methanol and cleared in Murray's clear (2:1 benzyl benzoate:benzyl alcohol) just prior to imaging. After staining, slides were mounted with Fluoromount G (SouthernBiotech), and air-dried overnight at room temperature.

Transmission Electron Microscopy

For TEM, hGOs were processed as previously described7. Briefly, organoids were fixed in 3% glutaraldehyde, washed in 0.1 M sodium cacodylate buffer, and incubated for one hour 4% osmium tetroxide. They were subsequently washed then dehydrated in ethanol series, and finally embedded in propylene oxide/LX112. Tissue was then sectioned and stained with 2% uranyl acetate followed by lead citrate. Images were visualized on Hitachi transmission electron microscope.

Pepsinogen ELISA

ELISA was performed using the Human Pepsinogen I (PGI) ELISA Kit (Thermo Scientific, EHPGI) according to manufacturer's instructions. Briefly, day 34 hGOs were collected and incubated in Cell Recovery Solution (Corning) for one hour at 4° C. then washed in PBS. Organoids were lysed with RIPA buffer followed by vigorous vortexing at high velocity for 30 minutes at room temperature. Lysates were pelleted and supernatant was collected and stored at −80° C. For ELISA, the samples and standards were performed in technical replicates. The reactions were measured on µQuant microplate plate reader (Bio Tek). Absorbance at 450 nm was measured, and the 570 nm absorbance was subtracted.

Acid Secretion Assays

Acid secretion assays were performed as previously described (Schumacher et al., 2015). hGOs were grown in the chambered coverglass (Thermo Scientific) and the chamber was placed on an inverted confocal microscope (Zeiss LSM 710), and experiments were performed under 5% $CO_2$ and 37° C. conditions (incubation chamber, PeCon, Erbach, Germany).

Freshly isolated mouse gastric fundic glands or cultured hGO were incubated with acridine orange (10 µM), then acridine orange fluorescence was excited at 458 nm or 488 nm and images were collected at 600-650 nm (Red) or 500-550 nm (Green), respectively. On the other hand, to monitor hGOs luminal pH, the ratiometric pH sensitive dye, 5-(and-6)-carboxy SNARF-5F (5 mM stock: EX 560 nm, EM 565-605 (Green) and 620-680 (Red) nm: Invitrogen) was microinjected (46-92 nl) into the lumen and monitored. Fluorescent dye also added into medium. Histamine (100 µM; Sigma) was added to media, while famotidine (100 µM; Sigma) or omeprazole (100 µM; Sigma) were pre-incubated at least 30 min before histamine. Images were analyzed using MetaMorph software (Molecular Devices, Downingtown, Pa.). Background corrected 620-680/565-605 nm ratio values were converted to pH using a standard curve.

Statistical Analysis

Statistical significance was determined using unpaired Student's T-test or one-way ANOVA with Dunnett's multiple comparison post-hoc test. A p value of <0.05 was considered significant.

Statistics and Experimental Reproducibility

No statistical analysis was used to determine experimental sample size, no specific method of randomization was used, and the investigators were not blinded during experiments. Statistical methods and measures are described in figure legends. The protocol for differentiation of fundic hGOs was successfully completed >20 times by seven independent users in the laboratory. In all cases, data shown are derived from a single experiment that is representative of multiple experiments.

EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A gastric fundus tissue is generated in vitro, comprising the following steps:

a) a mammalian definitive endoderm (DE) cell is contacted with a wnt pathway activator, an FGF signaling pathway activator (for example, FGF4), a BMP signalling pathway inhibitor (e.g., Noggin), and retinoic acid, for a first period, wherein the first period is sufficient to form a three-dimensional posterior foregut spheroid from said definitive endoderm;

b) the three-dimensional posterior foregut spheroid is suspended in a basement membrane matrix (for example, Matrigel) with a growth factor, Wnt signalling pathway activator, EGF signalling pathway activator, BMP signalling pathway inhibitor, and retinoic acid for a second period, sufficient to induce a fundic lineage comprising fundal hGOs (hFGOs);

c) the hFGOs of step b) are cultured in the presence of wnt pathway activator and EGF signalling pathway activator for a third period, d) the hFGOs of step c are cultured with wnt signaling pathway activator, EGF signalling pathway activator, and FGF10 for a fourth period;

e) the hFGOs of step d are contacted with a MEK inhibitor for a fifth period, (the MEK inhibitor may be, for example, PD0325901), for a period of time sufficient to form gastric fundus tissue comprising a functional fundic cell type.

Example 2

The method of Example 1, wherein said first period is three days±24 hours and wherein said retinoic acid is added for the third day of said period±24 hours

Example 3

The method of any preceding example, wherein said second period is three days±24 hours

Example 4

The method of any preceding example, wherein said third period is 11 days±24 hours

Example 5

The method of any preceding example, wherein said fourth period is 10 days±24 hours

Example 6

The method of any preceding example, wherein said fifth period is a two day period±24 hours

Example 7

The method of any preceding example, wherein step e) further comprises the step of contacting said fundal hGOs with an activator of BMP4 signalling.

Example 8

The method of any preceding example, wherein said functional fundic cell type is a parietal cell that expresses proton pump proteins and secretes acid.

Example 9

The method of any preceding example, wherein said functional fundic cell type is a chief cell that secretes pepsinogen.

Example 10

The method of any preceding example, wherein said step e is carried out for a period of time sufficient to develop SOX2+GATA+PDX1− epithelium.

Example 11

The method of any preceding example, wherein said step d and step e are carried out for a period of time sufficient to confer stable expression of lineage markers MUC5AC, MUC6, PGC, and GHRL.

Example 12

The method of any preceding example, wherein said definitive endoderm is derived from a precursor cell selected from an embryonic stem cell, an embryonic germ cell, an induced pluripotent stem cell, a mesoderm cell, a definitive endoderm cell, a posterior endoderm cell, a posterior endoderm cell, and a hindgut cell, a definitive endoderm derived from a pluripotent stem cell, a definitive endoderm derived from a pluripotent stem cell selected from an embryonic stem cell, an adult stem cell, or an induced pluripotent stem cell.

Example 13

The method of any preceding example, wherein said definitive endoderm is derived from contacting a pluripotent stem cell with one or more molecules selected from Activin, the BMP subgroups of the TGF-beta superfamily of growth factors; Nodal, Activin A, Activin B, BMP4, Wnt3a, and combinations thereof.

Example 14

The method of any preceding example, wherein said WNT pathway activator is one or more molecules selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16, for example, Wnt3a, or for example, Wnt3a at a concentration between about 50 to about 1500 ng/ml.

Example 15

The method of any preceding example, wherein said BMP signalling pathway inhibitor is selected from Noggin, Dorsomorphin, LDN189, DMH-1, and combinations thereof, for example, wherein said precursor cell is contacted with a BMP inhibitor at a concentration between about 50 to about 1500 ng/ml. The BMP inhibitor may be a protein and/or chemical capable of inhibiting the BMP signalling pathway.

Example 16

The method of any preceding example, wherein said steps are conducted in vitro.

Example 17

A composition comprising gastric tissue is produced according to any preceding Example. The gastric tissue is characterized by being free of innervation and/or blood vessels.

Example 18

A gastric fundus tissue is formed via the following steps: contacting a fundal hGO (hFGO) with a wnt pathway activating agent and an EGF signalling pathway activating agent for a first period, and a MEK inhibitor for a second period, (wherein said MEK inhibitor may be, for example, PD0325901), wherein the first and second periods are carried out for a period of time sufficient to form a functional fundic cell type;

wherein said hFGO are obtained by contacting a three-dimensional posterior foregut spheroid in a basement membrane matrix with a growth factor, a wnt pathway activating agent, an EGF signalling pathway activator, a BMP signalling pathway inhibitor, and retinoic acid for a period of time sufficient to convert said three-dimensional posterior foregut spheroid to said hFGO;

wherein said three-dimensional posterior foregut spheroids are obtained by contacting a mammalian definitive endoderm (DE) cells with a wnt pathway activating agent, an FGF signaling pathway activating agent, a BMP signalling pathway inhibitor, and retinoic acid.

REFERENCES

1. Lancaster, M. A. & Knoblich, J. A. Organogenesis in a dish: modeling development and disease using organoid technologies. Science 345, 1247125-1247125 (2014).

2. Huch, M. & Koo, B.-K. Modeling mouse and human development using organoid cultures. Development 142, 3113-3125 (2015).
3. Zhu, Z. & Huangfu, D. Human pluripotent stem cells: an emerging model in developmental biology. Development 140, 705-717 (2013).
4. Kim, T.-H. & Shivdasani, R. A. Stomach development, stem cells and disease. Development 143, 554-565 (2016).
5. Mills, J. C. & Shivdasani, R. A. Gastric epithelial stem cells. Gastroenterology 140, 412-424 (2011).
6. Hoffmann, W. Current Status on Stem Cells and Cancers of the Gastric Epithelium. IJMS 16, 19153-19169 (2015).
7. McCracken, K. W. et al. Modelling human development and disease in pluripotent stem-cell-derived gastric organoids. Nature 516, 400-404 (2014).
8. Noguchi, T.-A. K. et al. Generation of stomach tissue from mouse embryonic stem cells. Nature Cell Biology 17, 984-993 (2015).
9. Peek, R. M. *Helicobacter pylori* infection and disease: from humans to animal models. Disease Models & Mechanisms 1, 50-55 (2008).
10. Zorn, A. M. & Wells, J. M. Vertebrate Endoderm Development and Organ Formation. Annu. Rev. Cell Dev. Biol. 25, 221-251 (2009).
11. Kraus, M. R.-C. & Grapin-Botton, A. Patterning and shaping the endoderm in vivo and in culture. Curr. Opin. Genet. Dev. 22, 347-353 (2012).
12. Sherwood, R. I., Chen, T.-Y. A. & Melton, D. A. Transcriptional dynamics of endodermal organ formation. 238, 29-42 (2009).
13. Roth, R. B. et al. Gene expression analyses reveal molecular relationships among 20 regions of the human CNS. Neurogenetics 7, 67-80 (2006).
14. Kim, B.-M., Buchner, G., Miletich, I., Sharpe, P. T. & Shivdasani, R. A. The stomach mesenchymal transcription factor Barx1 specifies gastric epithelial identity through inhibition of transient Wnt signaling. Developmental Cell 8, 611-622 (2005).
15. Kim, B.-M., Woo, J., Kanellopoulou, C. & Shivdasani, R. A. Regulation of mouse stomach development and Barx1 expression by specific microRNAs. Development 138, 1081-1086 (2011).
16. Rodriguez, P. et al. BMP signaling in the development of the mouse esophagus and forestomach. Development 137, 4171-4176 (2010).
17. Lameris, A. L. et al. Expression profiling of claudins in the human gastrointestinal tract in health and during inflammatory bowel disease. Scand. J. Gastroenterol. 48, 58-69 (2013).
18. Keeley, T. M. & Samuelson, L. C. Cytodifferentiation of the postnatal mouse stomach in normal and Huntingtin-interacting protein 1-related-deficient mice. Am. J. Physiol. Gastrointest. Liver Physiol. 299, G1241-51 (2010).
19. Choi, E. et al. Cell lineage distribution atlas of the human stomach reveals heterogeneous gland populations in the gastric antrum. Gut 63, 1711-1720 (2014).
20. Stange, D. E. et al. Differentiated Troy+ chief cells act as reserve stem cells to generate all lineages of the stomach epithelium. Cell 155, 357-368 (2013).
21. Lennerz, J. K. M. et al. The transcription factor MIST1 is a novel human gastric chief cell marker whose expression is lost in metaplasia, dysplasia, and carcinoma. Am. J. Pathol. 177, 1514-1533 (2010).
22. Ramsey, V. G. et al. The maturation of mucus-secreting gastric epithelial progenitors into digestive-enzyme secreting zymogenic cells requires Mist1. Development 134, 211-222 (2007).
23. Lambrecht, N. W. G., Yakubov, I., Scott, D. & Sachs, G. Identification of the K efflux channel coupled to the gastric H-K-ATPase during acid secretion. Physiological Genomics 21, 81-91 (2005).
24. Schumacher, M. A. et al. The use of murine-derived fundic organoids in studies of gastric physiology. J. Physiol. (Lond.) 593, 1809-1827 (2015).
25. Barker, N. et al. Lgr5(+ve) stem cells drive self-renewal in the stomach and build long-lived gastric units in vitro. Cell Stem Cell 6, 25-36 (2010).
26. Bartfeld, S. et al. In vitro expansion of human gastric epithelial stem cells and their responses to bacterial infection. Gastroenterology 148, 126-136.e6 (2015).
27. Nielsen, C., Murtaugh, L. C., Chyung, J. C., Lassar, A. & Roberts, D. J. Gizzard Formation and the Role of Bapxl. Developmental Biology 231, 164-174 (2001).
28. Goldenring, J. R. et al. Overexpression of transforming growth factor-alpha alters differentiation of gastric cell lineages. Dig. Dis. Sci. 41, 773-784 (1996).
29. Speer, A. L. et al. Fibroblast growth factor 10-fibroblast growth factor receptor 2b mediated signaling is not required for adult glandular stomach homeostasis. PLoS ONE 7, e49127 (2012).
30. Goldenring, J. R. & Nomura, S. Differentiation of the gastric mucosa III. Animal models of oxyntic atrophy and metaplasia. AJP: Gastrointestinal and Liver Physiology 291, G999-1004 (2006).
31. Huh, W. J., Coffey, R. J. & Washington, M. K. Ménétrier's Disease: Its Mimickers and Pathogenesis. J Pathol Transl Med 50, 10-16 (2016).
32. Park, Y. H. & Kim, N. Review of atrophic gastritis and intestinal metaplasia as a premalignant lesion of gastric cancer. J Cancer Prev 20, 25-40 (2015).
33. Weis, V. G. & Goldenring, J. R. Current understanding of SPEM and its standing in the preneoplastic process. Gastric Cancer 12, 189-197 (2009).
34. Nomura, S. et al. Evidence for Repatterning of the Gastric Fundic Epithelium Associated With Ménétrier's Disease and TGFα Overexpression. Gastroenterology 128, 1292-1305 (2005).
35. Choi, E., Hendley, A. M., Bailey, J. M., Leach, S. D. & Goldenring, J. R. Expression of Activated Ras in Gastric Chief Cells of Mice Leads to the Full Spectrum of Metaplastic Lineage Transitions. Gastroenterology 0, (2015).
36. McCracken, K W, Howell J C, Wells, J M & Spence, J R, Generating human intestinal tissue from pluripotent stem cells in vitro. Nat. Protocols 6, 1920-1928 (2011).
37. Ahnfelt-Ronne, J et al., An improved method for three-dimensional reconstruction of protein expression patterns in intact mouse and chicken embryos and organs. J. Histochem. Cytochem. 55, 925-930 (2007).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An in vitro method of inducing formation of a gastric fundus tissue comprising a functional fundic cell type, comprising the steps of:
   a) contacting a mammalian definitive endoderm (DE) cell with a wnt activator, an FGF activator, a BMP inhibitor, and retinoic acid, for a first period, wherein said first period is for a length of time sufficient to form a three-dimensional posterior foregut spheroid from said definitive endoderm;
   b) contacting said three-dimensional posterior foregut spheroid with a growth factor, said Wnt activator, an EGF signalling pathway activator, said BMP inhibitor, and retinoic acid for a second period, wherein said second period is for a length of time sufficient to induce a fundic lineage comprising human fundic-type gastric organoids (hFGOs);
   c) culturing said hFGOs of step b) with said wnt activator and said EGF activator for a third period;
   d) culturing said hFGOs of step c) with said wnt activator, said EGF activator, and FGF10 for a fourth period;
   e) contacting said hFGOs of step d) with a MEK inhibitor for a fifth period, wherein said fifth period is for a period of time sufficient to form said gastric fundus tissue comprising a functional fundic cell type.

2. The method of claim 1, wherein said first period is three days±24 hours and wherein said retinoic acid is added for the third day of said period±24 hours.

3. The method of claim 1, wherein said second period is three days±24 hours.

4. The method of claim 1, wherein said third period is 11 days±24 hours.

5. The method of claim 1, wherein said fourth period is 10 days±24 hours.

6. The method of claim 1, wherein said fifth period is a two day period±24 hours.

7. The method of claim 1, wherein step e) further comprises the step of contacting said hFGOs with an activator of BMP4 signalling.

8. The method of claim 1, wherein said functional fundic cell type is a parietal cell that expresses proton pump proteins and secretes acid.

9. The method of claim 1, wherein said functional fundic cell type is a chief cell that secretes pepsinogen.

10. The method of claim 1, wherein said step e) is carried out for a period of time sufficient to develop SOX2+GATA+ PDX1− epithelium.

11. The method of claim 1, wherein said step d) and step e) are carried out for a period of time sufficient to confer stable expression of lineage markers MUC5AC, MUC6, PGC, and GHRL.

12. The method of claim 1, wherein said definitive endoderm is derived from a precursor cell selected from an embryonic stem cell, an embryonic germ cell, and an induced pluripotent stem cell.

13. The method of claim 1, wherein said definitive endoderm is derived from contacting a pluripotent stem cell with one or more molecules selected from Nodal, Activin A, Activin B, BMP4, Wnt3a, and combinations thereof.

14. The method of claim 1, wherein said WNT is one or more molecules selected from Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16.

15. The method of claim 1, wherein said BMP inhibitor is selected from Noggin, Dorsomorphin, LDN189, DMH-1, and combinations thereof.

16. An in vitro method of forming a functional fundic cell type comprising the steps of:
   a) contacting an hFGO with a wnt activator and an EGF activator for a first period, and
   b) contacting the hFGO of step a) with a MEK inhibitor for a second period, wherein said first and second periods are carried out for a period of time sufficient to form a functional fundic cell type;
   wherein said hFGO is obtained by contacting a three-dimensional posterior foregut spheroid with a growth factor, a wnt activator, an EGF activator, a BMP inhibitor, and retinoic acid for a period of time sufficient to convert said three-dimensional posterior foregut spheroid to said hFGO;
   wherein said three-dimensional posterior foregut spheroids are obtained by contacting a mammalian DE cells with a wnt activator, an FGF activator, a BMP inhibitor, and retinoic acid.

\* \* \* \* \*

```
                         SEQUENCE LISTING

<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: hATP4A forward

<400> SEQUENCE: 1
tggtagtagc caaagcagcc                                                     20

<210> SEQ ID NO 2
<211> LENGTH: 19
<212> TYPE: DNA
<213> ORGANISM: Artificial Sequence
<220> FEATURE:
<223> OTHER INFORMATION: hATP4A reverse

<400> SEQUENCE: 2
tgccatccag gctagtgag                                                      19

<210> SEQ ID NO 3
<211> LENGTH: 20
<212> TYPE: DNA
<213> ORGANISM: Artificial Sequence
<220> FEATURE:
<223> OTHER INFORMATION: hATP4B forward

<400> SEQUENCE: 3
accacgtaga aggccacgta                                                     20

<210> SEQ ID NO 4
<211> LENGTH: 20
<212> TYPE: DNA
<213> ORGANISM: Artificial Sequence
<220> FEATURE:
<223> OTHER INFORMATION: hATP4B reverse

<400> SEQUENCE: 4
tggaggagtt ccagcgttac                                                     20

<210> SEQ ID NO 5
<211> LENGTH: 20
<212> TYPE: DNA
<213> ORGANISM: Artificial Sequence
<220> FEATURE:
<223> OTHER INFORMATION: hAXIN2 forward
```

```
<400> SEQUENCE: 5
ctggtgcaaa gacatagcca                                                  20

<210> SEQ ID NO 6
<211> LENGTH: 20
<212> TYPE: DNA
<213> ORGANISM: Artificial Sequence
<220> FEATURE:
<223> OTHER INFORMATION: hAXIN2 reverse

<400> SEQUENCE: 6
agtgtgaggt ccacggaaac                                                  20

<210> SEQ ID NO 7
<211> LENGTH: 20
<212> TYPE: DNA
<213> ORGANISM: Artificial Sequence
<220> FEATURE:
<223> OTHER INFORMATION: hCCK forward

<400> SEQUENCE: 7
cggtcactta tcctgtggct                                                  20

<210> SEQ ID NO 8
<211> LENGTH: 20
<212> TYPE: DNA
<213> ORGANISM: Artificial Sequence
<220> FEATURE:
<223> OTHER INFORMATION: hCCK reverse

<400> SEQUENCE: 8
ctgcgaagat caatccagca                                                  20

<210> SEQ ID NO 9
<211> LENGTH: 22
<212> TYPE: DNA
<213> ORGANISM: Artificial Sequence
<220> FEATURE:
<223> OTHER INFORMATION: hCDX2 forward

<400> SEQUENCE: 9
ctggagctgg agaaggagtt tc                                               22

<210> SEQ ID NO 10
<211> LENGTH: 24
<212> TYPE: DNA
<213> ORGANISM: Artificial Sequence
<220> FEATURE:
<223> OTHER INFORMATION: hCDX2 reverse

<400> SEQUENCE: 10
attttaacct gcctctcaga gagc                                             24

<210> SEQ ID NO 11
<211> LENGTH: 20
<212> TYPE: DNA
<213> ORGANISM: Artificial Sequence
<220> FEATURE:
<223> OTHER INFORMATION: hCHGA forward

<400> SEQUENCE: 11
tgacctcaac gatgcatttc                                                  20

<210> SEQ ID NO 12
<211> LENGTH: 20
```

```
<212> TYPE: DNA
<213> ORGANISM: Artificial Sequence
<220> FEATURE:
<223> OTHER INFORMATION: hCHGA reverse

<400> SEQUENCE: 12
ctgtcctggc tcttctgctc                                               20

<210> SEQ ID NO 13
<211> LENGTH: 21
<212> TYPE: DNA
<213> ORGANISM: Artificial Sequence
<220> FEATURE:
<223> OTHER INFORMATION: hGAPDH forward

<400> SEQUENCE: 13
cccatcacca tcttccagga g                                             21

<210> SEQ ID NO 14
<211> LENGTH: 22
<212> TYPE: DNA
<213> ORGANISM: Artificial Sequence
<220> FEATURE:
<223> OTHER INFORMATION: hGAPDH reverse

<400> SEQUENCE: 14
cttctccatg gtggtgaaga cg                                            22

<210> SEQ ID NO 15
<211> LENGTH: 20
<212> TYPE: DNA
<213> ORGANISM: Artificial Sequence
<220> FEATURE:
<223> OTHER INFORMATION: hGAST reverse

<400> SEQUENCE: 15
cagagccagt gcaaagatca                                               20

<210> SEQ ID NO 16
<211> LENGTH: 20
<212> TYPE: DNA
<213> ORGANISM: Artificial Sequence
<220> FEATURE:
<223> OTHER INFORMATION: hGAST reverse

<400> SEQUENCE: 16
agagacctga gaggcaccag                                               20

<210> SEQ ID NO 17
<211> LENGTH: 21
<212> TYPE: DNA
<213> ORGANISM: Artificial Sequence
<220> FEATURE:
<223> OTHER INFORMATION: hGATA4 forward

<400> SEQUENCE: 17
tccaaaccag aaaacggaag c                                             21

<210> SEQ ID NO 18
<211> LENGTH: 20
<212> TYPE: DNA
<213> ORGANISM: Artificial Sequence
<220> FEATURE:
<223> OTHER INFORMATION: hGATA4 reverse

<400> SEQUENCE: 18
```

```
gcccgtagtg agatgacagg                                          20

<210> SEQ ID NO 19
<211> LENGTH: 20
<212> TYPE: DNA
<213> ORGANISM: Artificial Sequence
<220> FEATURE:
<223> OTHER INFORMATION: hGHRL forward

<400> SEQUENCE: 19
gctggtactg aaccccctgac                                         20

<210> SEQ ID NO 20
<211> LENGTH: 20
<212> TYPE: DNA
<213> ORGANISM: Artificial Sequence
<220> FEATURE:
<223> OTHER INFORMATION: hGHRL reverse

<400> SEQUENCE: 20
gatggaggtc aagcagaagg                                          20

<210> SEQ ID NO 21
<211> LENGTH: 20
<212> TYPE: DNA
<213> ORGANISM: Artificial Sequence
<220> FEATURE:
<223> OTHER INFORMATION: hGIF forward

<400> SEQUENCE: 21
cattttccgc gatattgttg                                          20

<210> SEQ ID NO 22
<211> LENGTH: 20
<212> TYPE: DNA
<213> ORGANISM: Artificial Sequence
<220> FEATURE:
<223> OTHER INFORMATION: hGIF reverse

<400> SEQUENCE: 22
gcacagcgca aaaatcctat                                          20

<210> SEQ ID NO 23
<211> LENGTH: 17
<212> TYPE: DNA
<213> ORGANISM: Artificial Sequence
<220> FEATURE:
<223> OTHER INFORMATION: hIRX2 forward

<400> SEQUENCE: 23
gtggtgtgcg cgtcgta                                             17

<210> SEQ ID NO 24
<211> LENGTH: 17
<212> TYPE: DNA
<213> ORGANISM: Artificial Sequence
<220> FEATURE:
<223> OTHER INFORMATION: hIRX2 reverse

<400> SEQUENCE: 24
ggcgttcagc ccctacc                                             17

<210> SEQ ID NO 25
<211> LENGTH: 20
<212> TYPE: DNA
<213> ORGANISM: Artificial Sequence
```

```
<220> FEATURE:
<223> OTHER INFORMATION: hIRX3 forward

<400> SEQUENCE: 25
ggagagagcc gataagacca                                              20

<210> SEQ ID NO 26
<211> LENGTH: 20
<212> TYPE: DNA
<213> ORGANISM: Artificial Sequence
<220> FEATURE:
<223> OTHER INFORMATION: hIRX3 reverse

<400> SEQUENCE: 26
agtgccttgg aagtggagaa                                              20

<210> SEQ ID NO 27
<211> LENGTH: 20
<212> TYPE: DNA
<213> ORGANISM: Artificial Sequence
<220> FEATURE:
<223> OTHER INFORMATION: hIRX5 forward

<400> SEQUENCE: 27
ggtgtgtggt cgtagggaga                                              20

<210> SEQ ID NO 28
<211> LENGTH: 19
<212> TYPE: DNA
<213> ORGANISM: Artificial Sequence
<220> FEATURE:
<223> OTHER INFORMATION: hIRX5 reverse

<400> SEQUENCE: 28
gctacaactc gcacctcca                                               19

<210> SEQ ID NO 29
<211> LENGTH: 19
<212> TYPE: DNA
<213> ORGANISM: Artificial Sequence
<220> FEATURE:
<223> OTHER INFORMATION: hMIST1 forward

<400> SEQUENCE: 29
tgctggacat ggtcaggat                                               19

<210> SEQ ID NO 30
<211> LENGTH: 20
<212> TYPE: DNA
<213> ORGANISM: Artificial Sequence
<220> FEATURE:
<223> OTHER INFORMATION: hMIST1 reverse

<400> SEQUENCE: 30
cggacaagaa gctctccaag                                              20

<210> SEQ ID NO 31
<211> LENGTH: 20
<212> TYPE: DNA
<213> ORGANISM: Artificial Sequence
<220> FEATURE:
<223> OTHER INFORMATION: hMUC2 forward

<400> SEQUENCE: 31
tgtaggcatc gctcttctca                                              20
```

```
<210> SEQ ID NO 32
<211> LENGTH: 20
<212> TYPE: DNA
<213> ORGANISM: Artificial Sequence
<220> FEATURE:
<223> OTHER INFORMATION: hMUC2 reverse

<400> SEQUENCE: 32
gacaccatct acctcacccg                                               20

<210> SEQ ID NO 33
<211> LENGTH: 20
<212> TYPE: DNA
<213> ORGANISM: Artificial Sequence
<220> FEATURE:
<223> OTHER INFORMATION: hMUC5AC forward

<400> SEQUENCE: 33
ccaaggagaa cctcccatat                                               20

<210> SEQ ID NO 34
<211> LENGTH: 18
<212> TYPE: DNA
<213> ORGANISM: Artificial Sequence
<220> FEATURE:
<223> OTHER INFORMATION: hMUC5AC reverse

<400> SEQUENCE: 34
ccaagcgtca ttcctgag                                                 18

<210> SEQ ID NO 35
<211> LENGTH: 24
<212> TYPE: DNA
<213> ORGANISM: Artificial Sequence
<220> FEATURE:
<223> OTHER INFORMATION: hMUC6 forward

<400> SEQUENCE: 35
cagcaggagg agatcacgtt caag                                          24

<210> SEQ ID NO 36
<211> LENGTH: 24
<212> TYPE: DNA
<213> ORGANISM: Artificial Sequence
<220> FEATURE:
<223> OTHER INFORMATION: hMUC6 reverse

<400> SEQUENCE: 36
gtgggtgttt tcctgtctgt catc                                          24

<210> SEQ ID NO 37
<211> LENGTH: 18
<212> TYPE: DNA
<213> ORGANISM: Artificial Sequence
<220> FEATURE:
<223> OTHER INFORMATION: hPDX1 forward

<400> SEQUENCE: 37
cgtccgcttg ttctcctc                                                 18

<210> SEQ ID NO 38
<211> LENGTH: 20
<212> TYPE: DNA
<213> ORGANISM: Artificial Sequence
<220> FEATURE:
<223> OTHER INFORMATION: hPDX1 reverse
```

-continued

<210> SEQ ID NO 38

<400> SEQUENCE: 38
cctttcccat ggatgaagtc                                            20

<210> SEQ ID NO 39
<211> LENGTH: 20
<212> TYPE: DNA
<213> ORGANISM: Artificial Sequence
<220> FEATURE:
<223> OTHER INFORMATION: hSCT forward

<400> SEQUENCE: 39
ggttctgaaa ccataggccc                                            20

<210> SEQ ID NO 40
<211> LENGTH: 18
<212> TYPE: DNA
<213> ORGANISM: Artificial Sequence
<220> FEATURE:
<223> OTHER INFORMATION: hSCT reverse

<400> SEQUENCE: 40
gtcagggtcc aacatgcc                                              18

<210> SEQ ID NO 41
<211> LENGTH: 20
<212> TYPE: DNA
<213> ORGANISM: Artificial Sequence
<220> FEATURE:
<223> OTHER INFORMATION: hSOX2 forward

<400> SEQUENCE: 41
gcttagcctc gtcgatgaac                                            20

<210> SEQ ID NO 42
<211> LENGTH: 20
<212> TYPE: DNA
<213> ORGANISM: Artificial Sequence
<220> FEATURE:
<223> OTHER INFORMATION: hSOX2 reverse

<400> SEQUENCE: 42
aaccccaaga tgcacaactc                                            20

<210> SEQ ID NO 43
<211> LENGTH: 20
<212> TYPE: DNA
<213> ORGANISM: Artificial Sequence
<220> FEATURE:
<223> OTHER INFORMATION: mCdx2 forward

<400> SEQUENCE: 43
tctgtgtaca ccacccggta                                            20

<210> SEQ ID NO 44
<211> LENGTH: 20
<212> TYPE: DNA
<213> ORGANISM: Artificial Sequence
<220> FEATURE:
<223> OTHER INFORMATION: mCdx2 reverse

<400> SEQUENCE: 44
gaaacctgtg cgagtggatg                                            20

<210> SEQ ID NO 45

```
<211> LENGTH: 18
<212> TYPE: DNA
<213> ORGANISM: Artificial Sequence
<220> FEATURE:
<223> OTHER INFORMATION: mGata4 forward

<400> SEQUENCE: 45
ccatctcgcc tccagagt                                              18

<210> SEQ ID NO 46
<211> LENGTH: 20
<212> TYPE: DNA
<213> ORGANISM: Artificial Sequence
<220> FEATURE:
<223> OTHER INFORMATION: mGata4 reverse

<400> SEQUENCE: 46
ctggaagaca ccccaatctc                                            20

<210> SEQ ID NO 47
<211> LENGTH: 20
<212> TYPE: DNA
<213> ORGANISM: Artificial Sequence
<220> FEATURE:
<223> OTHER INFORMATION: mGapdh forward

<400> SEQUENCE: 47
ttgatggcaa caatctccac                                            20

<210> SEQ ID NO 48
<211> LENGTH: 20
<212> TYPE: DNA
<213> ORGANISM: Artificial Sequence
<220> FEATURE:
<223> OTHER INFORMATION: mGapdh reverse

<400> SEQUENCE: 48
cgtcccgtag acaaaatggt                                            20

<210> SEQ ID NO 49
<211> LENGTH: 20
<212> TYPE: DNA
<213> ORGANISM: Artificial Sequence
<220> FEATURE:
<223> OTHER INFORMATION: mIrx1 forward

<400> SEQUENCE: 49
aataagcagg cgttgtgtgg                                            20

<210> SEQ ID NO 50
<211> LENGTH: 20
<212> TYPE: DNA
<213> ORGANISM: Artificial Sequence
<220> FEATURE:
<223> OTHER INFORMATION: mIrx1 reverse

<400> SEQUENCE: 50
ctcagcctct tctcgcagat                                            20

<210> SEQ ID NO 51
<211> LENGTH: 19
<212> TYPE: DNA
<213> ORGANISM: Artificial Sequence
<220> FEATURE:
<223> OTHER INFORMATION: mIrx2 forward

<400> SEQUENCE: 51
```
agctggtatg gataggccg                                    19

<210> SEQ ID NO 52
<211> LENGTH: 18
<212> TYPE: DNA
<213> ORGANISM: Artificial Sequence
<220> FEATURE:
<223> OTHER INFORMATION: mIrx2 reverse

<400> SEQUENCE: 52
ggcttcccgt cctacgtg                                     18

<210> SEQ ID NO 53
<211> LENGTH: 20
<212> TYPE: DNA
<213> ORGANISM: Artificial Sequence
<220> FEATURE:
<223> OTHER INFORMATION: mIrx3 reverse

<400> SEQUENCE: 53
ataagaccag agcagcgtcc                                   20

<210> SEQ ID NO 54
<211> LENGTH: 20
<212> TYPE: DNA
<213> ORGANISM: Artificial Sequence
<220> FEATURE:
<223> OTHER INFORMATION: mIrx3 reverse

<400> SEQUENCE: 54
gtgccttgga agtggagaaa                                   20

<210> SEQ ID NO 55
<211> LENGTH: 20
<212> TYPE: DNA
<213> ORGANISM: Artificial Sequence
<220> FEATURE:
<223> OTHER INFORMATION: mIrx5 forward

<400> SEQUENCE: 55
ggagtgtggt cgtagggaga                                   20

<210> SEQ ID NO 56
<211> LENGTH: 19
<212> TYPE: DNA
<213> ORGANISM: Artificial Sequence
<220> FEATURE:
<223> OTHER INFORMATION: mIrx5 reverse

<400> SEQUENCE: 56
gctacaactc gcacctcca                                    19

<210> SEQ ID NO 57
<211> LENGTH: 20
<212> TYPE: DNA
<213> ORGANISM: Artificial Sequence
<220> FEATURE:
<223> OTHER INFORMATION: mPdx1 forward

<400> SEQUENCE: 57
acgggtcctc ttgttttcct                                   20

<210> SEQ ID NO 58
<211> LENGTH: 20
<212> TYPE: DNA

<213> ORGANISM: Artificial Sequence
<220> FEATURE:
<223> OTHER INFORMATION: mPdx1 reverse

<400> SEQUENCE: 58
tggatgaaat ccaccaaagc                                               20

<210> SEQ ID NO 59
<211> LENGTH: 18
<212> TYPE: DNA
<213> ORGANISM: Artificial Sequence
<220> FEATURE:
<223> OTHER INFORMATION: mPitx1 forward

<400> SEQUENCE: 59
gtccatggag gtggggac                                                 18

<210> SEQ ID NO 60
<211> LENGTH: 19
<212> TYPE: DNA
<213> ORGANISM: Artificial Sequence
<220> FEATURE:
<223> OTHER INFORMATION: mPitx1 reverse

<400> SEQUENCE: 60
gcttaggcgc cactctctt                                                19

<210> SEQ ID NO 61
<211> LENGTH: 20
<212> TYPE: DNA
<213> ORGANISM: Artificial Sequence
<220> FEATURE:
<223> OTHER INFORMATION: mSox2 forward

<400> SEQUENCE: 61
aaagcgttaa tttggatggg                                               20

<210> SEQ ID NO 62
<211> LENGTH: 20
<212> TYPE: DNA
<213> ORGANISM: Artificial Sequence
<220> FEATURE:
<223> OTHER INFORMATION: mSox2 reverse

<400> SEQUENCE: 62
acaagagaat tgggaggggt                                               20

<210> SEQ ID NO 63
<211> LENGTH: 20
<212> TYPE: DNA
<213> ORGANISM: Artificial Sequence
<220> FEATURE:
<223> OTHER INFORMATION: mTrp63 forward

<400> SEQUENCE: 63
agcttcttca gttcggtgga                                               20

<210> SEQ ID NO 64
<211> LENGTH: 20
<212> TYPE: DNA

```
<213> ORGANISM: Artificial Sequence
<220> FEATURE:
<223> OTHER INFORMATION: mTrp63 reverse

<400> SEQUENCE: 64
cctccaacac agattacccg                                              20
```